United States Patent
Maher

(10) Patent No.: US 11,221,329 B2
(45) Date of Patent: Jan. 11, 2022

(54) TREATMENT OF NEUROLOGICAL AND NEURODEVELOPMENTAL DISEASES AND DISORDERS ASSOCIATED WITH ABERRANT ION CHANNEL EXPRESSION AND ACTIVITY

(71) Applicant: LIEBER INSTITUTE FOR BRAIN DEVELOPMENT, Baltimore, MD (US)

(72) Inventor: Brady Maher, Baltimore, MD (US)

(73) Assignee: Lieber Institute, Inc., Baltimore, MD (US)

(*) Notice: Subject to any disclaimer, the term of this patent is extended or adjusted under 35 U.S.C. 154(b) by 0 days.

(21) Appl. No.: 15/771,857

(22) PCT Filed: Oct. 27, 2016

(86) PCT No.: PCT/US2016/059128
§ 371 (c)(1),
(2) Date: Apr. 27, 2018

(87) PCT Pub. No.: WO2017/075222
PCT Pub. Date: May 4, 2017

(65) Prior Publication Data
US 2018/0328915 A1    Nov. 15, 2018

Related U.S. Application Data

(60) Provisional application No. 62/248,995, filed on Oct. 30, 2015.

(51) Int. Cl.
| | |
|---|---|
| A61K 31/44 | (2006.01) |
| A61P 25/18 | (2006.01) |
| G01N 33/50 | (2006.01) |
| A61K 45/06 | (2006.01) |
| A61K 31/4439 | (2006.01) |
| A61K 38/13 | (2006.01) |
| A61P 43/00 | (2006.01) |
| A61K 9/00 | (2006.01) |
| C12Q 1/6883 | (2018.01) |

(52) U.S. Cl.
CPC ....... *G01N 33/5058* (2013.01); *A61K 9/0019* (2013.01); *A61K 31/4439* (2013.01); *A61K 38/13* (2013.01); *A61K 45/06* (2013.01); *A61P 25/18* (2018.01); *A61P 43/00* (2018.01); *C12Q 1/6883* (2013.01); *G01N 2500/10* (2013.01)

(58) Field of Classification Search
CPC ...... A61P 25/18; A61K 31/4439; A61K 38/13
See application file for complete search history.

(56) References Cited

U.S. PATENT DOCUMENTS

| | | | |
|---|---|---|---|
| 2011/0021495 A1* | 1/2011 | Gonzalez et al. | ... C07D 239/34 |
| 2011/0312533 A1 | 12/2011 | Shekdar | |
| 2014/0309181 A1* | 10/2014 | Collard et al. | ..... A61K 31/7048 |
| 2015/0166589 A1 | 6/2015 | Anderson et al. | |

OTHER PUBLICATIONS

Rannals et al. Psychiatric Risk Gene Transcription Factor 4 Regulates Intrinsic Excitability of Prefrontal Neurons via Repression of SCN10a and KCNQ1. Neuron. (Apr. 6, 2016) vol. 90, No. 1.
Rannals et al. Neurodevelopmental models of transcription factor 4 deficiency converge on a common ion channel as a potential therapeutic target for Pitt Hopkins Syndrome. Rare Diseases. 2016. vol. 4, No. 1, e1220468 (5 pages).
Wittmann. Linking the Neuropsychiatric Disease Gene TCF4 to Neuronal Network Activity-Dependent Regulatory Networks. The Journal of Neuroscience. Mar. 14, 2018. 38(11):2653-2655.
Ekins et al. Repurposing the Dihydropyridine Calcium Channel Inhibitor Nicardipine as a Nav1.8 Inhibitor In vivo for Pitts Hopkins Syndrome. Pharm Res. (2020) 37:127.
Rannals et al. Molecular Mechanisms of Transcription Factor 4 in Pitt Hopkins Syndrome. Curr. Genet. Med. Rep. Mar. 2017. 5(1):1-7.
Abel, H. J. (2003). Relationships Between Intracellular Calcium and Afterhyperpolarizations in Neocortical Pyramidal Neurons. J Neurophysiol 91, 324-335.
Alvarez, V. A., Ridenour, D. A., and Sabatini, B. L. (2006). Retraction of synapses and dendritic spines induced by off-target effects of RNA interference. Journal of Neuroscience 26, 7820-7825.
Amiel, J., Rio, M., de Pontual, L., Redon, R., Malan, V., Boddaert, N., Plouin, P., Carter, N. P., Lyonnet, S., Munnich, A., et al. (2007). Mutations in TCF4, encoding a class I basic helix-loop-helix transcription factor, are responsible for Pitt-Hopkins syndrome, a severe epileptic encephalopathy associated with autonomic dysfunction. Am J Hum Genet 80, 988-993.
Baek, S. T., Kerjan, G., Bielas, S. L., Lee, J. E., Fenstermaker, A. G., Novarino, G., and Gleeson, J. G. (2014). Off-target effect of doublecortin family shRNA on neuronal migration associated with endogenous microRNA dysregulation. Neuron 82, 1255-1262.

(Continued)

*Primary Examiner* — Robert C Hayes
(74) *Attorney, Agent, or Firm* — Ballard Spahr LLP

(57) ABSTRACT

Provided are methods for treating and/or reducing the symptoms of a neurological or neurodevelopmental disease or disorder characterized by ectopic expression of certain ion channels, in particular, the Nav1.8 subtype SCN10a sodium channel, or the KCNQ1 potassium channel, in neuronal cells of the central nervous system (CNS) of a subject by administering to a subject in need an antagonist of one or both of these ion channels, and in particular, an antagonist of SCN10a, to block, reduce, or suppress the aberrant CNS neuronal ion channel expression and/or activity and normalize behavioral and cognitive defects associated with the neurological and neurodevelopmental disease or disorder, so as to treat and/or reduce the symptoms of the neurological or neurodevelopmental disease or disorder. Examples of such diseases or disorders that may be treated by the described methods include, for example, Pitt-Hopkins Syndrome (PTHS), autism, autism spectrum disorder, schizophrenia, 18q syndrome and the like.

20 Claims, 44 Drawing Sheets

Specification includes a Sequence Listing.

(56) References Cited

OTHER PUBLICATIONS

Baker, M. D., and Wood, J. N. (2001). Involvement of Na+ channels in pain pathways. Trends in Pharmacological Sciences 22, 27-31.

Bean, B. P. (2007). The action potential in mammalian central neurons. Nat Rev Neurosci 8, 451-465.

Blair, N. T., and Bean, B. P. (2003). Role of tetrodotoxin-resistant Na+ current slow inactivation in adaptation of action potential firing in small-diameter dorsal root ganglion neurons. Journal of Neuroscience 23, 10338-10350.

Brockschmidt, A., Filippi, A., Charbel Issa, P., Nelles, M., Urbach, H., Eter, N., Driever, W., and Weber, R. G. (2011). Neurologic and ocular phenotype in Pitt-Hopkins syndrome and a zebrafish model. Hum Genet 130, 645-655.

Callicott, J. H. (2003). An expanded role for functional neuroimaging in schizophrenia. Curr Opin Neurobiol 13, 256-260.

Chen, F., Maher, B. J., and Loturco, J. J. (2014). PiggyBac Transposon-Mediated Cellular Transgenesis in Mammalian Forebrain by In Utero Electroporation. Cold Spring Harb Protoc 2014, pdb.prot073650-pdb.prot073650.

Consortium, T. E. P. (2012). An integrated encyclopedia of DNA elements in the human genome. Nature 489, 57-74.

Soileau, B., Hasi, M., Sebold, C., Hill, A., O'Donnell, L., Hale, D. E., and Cody, J. D. (2014). Adults with Chromosome 18 Abnormalities. J Genet Couns 1-12.

Towart, R., Linders, J. T. M., Hermans, A. N., Rohrbacher, J., van der Linde, H. J., Ercken, M., Cik, M., Roevens, P., Teisman, A., and Gallacher, D. J. (2009). Blockade of the IKs potassium channel: An overlooked cardiovascular liability in drug safety screening? Journal of Pharmacological and Toxicological Methods 60, 1-10.

Tzingounis, A. V., and Nicoll, R. A. (2008). Contribution of KCNQ2 and KCNQ3 to the medium and slow afterhyperpolarization currents. Proceedings of the National Academy of Sciences 105, 19974-19979.

Tzingounis, A. V., Kobayashi, M., Takamatsu, K., and Nicoll, R. A. (2007). Hippocalcin Gates the Calcium Activation of the Slow Afterhyperpolarization in Hippocampal Pyramidal Cells. Neuron 53, 487-493.

Vijayaragavan, K., O'Leary, M. E., and Chahine, M. (2001). Gating properties of Na(v)1.7 and Na(v)1.8 peripheral nerve sodium channels. Journal of Neuroscience 21, 7909-7918.

Vogalis, F., Storm, J. F., and Lancaster, B. (2003). SK channels and the varieties of slow after-hyperpolarizations in neurons. Eur J Neurosci 18, 3155-3166.

Wang, M., Yang, Y., Wang, C.-J., Gamo, N. J., Jin, L. E., Mazer, J. A., Morrison, J. H., Wang, X.-J., and Arnsten, A. F. T. (2013). NMDA Receptors Subserve Persistent Neuronal Firing during Working Memory in Dorsolateral Prefrontal Cortex. Neuron 77, 736-749.

Whalen, S., Heron, D., Gaillon, T., Moldovan, O., Rossi, M., Devillard, F., Giuliano, F., Soares, G., Mathieu-Dramard, M., Afenjar, A., et al. (2012). Novel comprehensive diagnostic strategy in Pitt-Hopkins syndrome: clinical score and further delineation of the TCF4 mutational spectrum. Hum. Mutat. 33, 64-72.

Williams, H. J., Moskvina, V., Smith, R. L., Dwyer, S., Russo, G., Owen, M. J., and O'Donovan, M. C. (2011). Association between TCF4 and schizophrenia does not exert its effect by common nonsynonymous variation or by influencing cis-acting regulation of mRNA expression in adult human brain. Am. J. Med. Genet. 156, 781-784.

Zhang, W., and Linden, D. J. (2003). The other side of the engram: experience-driven changes in neuronal intrinsic excitability. Nat Rev Neurosci 4, 885-900.

Zweier, C., Sticht, H., Bijlsma, E. K., Clayton-Smith, J., Boonen, S. E., Fryer, A., Greally, M. T., Hoffmann, L., Hollander, den, N. S., Jongmans, M., et al. (2008). Further delineation of Pitt-Hopkins syndrome: phenotypic and genotypic description of 16 novel patients. J. Med. Genet. 45, 738-744.

Zhu, X., Gu, H., Liu, Z., Xu, Z., Chen, X., Sun, X., Zhai, J., Zhang, Q., Chen, M., Wang, K., et al. (2012). Associations between TCF4 Gene Polymorphism and Cognitive Functions in Schizophrenia Patients and Healthy Controls. Neuropsychopharmacology 38, 683-689.

Zhuang, Y., Cheng, P., and Weintraub, H. (1996). B-lymphocyte development is regulated by the combined dosage of three basic helix-loop-helix genes, E2A, E2-2, and HEB. Mol Cell Biol 16, 2898-2905.

Maher, Dr. Brady J., Molecular Psychiatry Meeting, Nov. 8, 2014, The Schizophrenia and Autism Spectrum Disorder gene TCF4 regulates cortical structure and neoronal physiology. Slides 1-21.

Maher, Dr. Brady J., Maher Molecular Psychiatry Meeting, Oct. 31, 2015, Phenotype Discovery and Therapeutic Target Identification Using a Cell Autonomous Model of Neurodevelopmental Disorders. Slides 1-26.

Maher, Dr. Brady, SOBP Talk, May 16, 2015, The Schizophrenia and Autism Spectrum Disorder Gene TCF4 Regulates the Intrinsic Excitabilit of Prefrontal Neurons. Slides 1-19.

Rannals, M.D., Rannals et al., Dec. 4, 2014 poster bjm edits, The schizophrenia and autism associated gene, transcription factor. p. 1.

Cooper, E. C., Aldape, K. D., Abosch, A., Barbaro, N. M., Berger, M. S., Peacock, W. S., Jan, Y. N., and Jan, L. Y. (2000). Colocalization and coassembly of two human brain M-type potassium channel subunits that are mutated in epilepsy. Proc Natl Acad Sci USA 97, 4914-4919.

Corneliussen, B., Thornell, A., Hallberg, B., and Grundstrom, T. (1991). Helix-loop-helix transcriptional activators bind to a sequence in glucocorticoid response elements of retrovirus enhancers. J. Virol. 65, 6084-6093.

Daoudal, G., and Debanne, D. (2003). Long-term plasticity of intrinsic excitability: learning rules and mechanisms. Learning & Memory 10, 456-465.

De Pontual, L. C., Mathieu, Y., Golzio, C., Rio, M. N., Malan, V. R., Boddaert, N., Soufflet, C., Picard, C., Durandy, A., Dobbie, A., et al. (2009). Mutational, functional, and expression studies of the TCF4 gene in Pitt-Hopkins syndrome. Hum. Mutat. 30, 669-676.

Delmas, P., and Brown, D. A. (2005). Pathways modulating neural KCNQ/M (Kv7) potassium channels. Nat Rev Neurosci 6, 850-862.

Disterhoft, J. F., and Oh, M. M. (2006). Learning, aging and intrinsic neuronal plasticity. Trends Neurosci 29, 587-599.

Duan, X., Chang, J. H., Ge, S., Faulkner, R. L., Kim, J. Y., Kitabatake, Y., Liu, X.-B., Yang, C.-H., Jordan, J. D., Ma, D. K., et al. (2007). Disrupted-In-Schizophrenia 1 regulates integration of newly generated neurons in the adult brain. Cell 130, 1146-1158.

Faber, E. S. L., and Sah, P. (2003). Calcium-Activated Potassium Channels: Multiple Contributions to Neuronal Function. Neuroscientist 9, 181-194.

Flora, A., Garcia, J. J., Thaller, C., and Zoghbi, H. Y. (2007). The E-protein Tcf4 interacts with Math1 to regulate differentiation of a specific subset of neuronal progenitors. Proc Natl Acad Sci USA 104, 15382-15387.

Forrest, M., Chapman, R. M., Doyle, M., Tinsley, C. L., Waite, A., and Blake, D. J. (2012). Functional analysis of TCF4 missense mutations that cause Pitt-Hopkins Syndrome. Hum. Mutat. n/a-n/a.

Giese, K. P., Peters, M., and Vernon, J. (2001). Modulation of excitability as a learning and memory mechanism: A molecular genetic perspective. Physiology & Behavior 73, 803-810.

Goldberg, T. E., and Weinberger, D. R. (1988). Probing prefrontal function in schizophrenia with neuropsychological paradigms. Schizophr Bull 14, 179-183.

Goldman-Rakic, P. S. (1994). Working memory dysfunction in schizophrenia. J Neuropsychiatry Clin Neurosci 6, 348-357.

Goldman-Rakic, P. S. (1995). Cellular basis of working memory. Neuron 14, 477-485.

Grubišić, V., Kennedy, A. J., Sweatt, J. D., and Parpura, V. (2015). Pitt-Hopkins Mouse Model has Altered Particular Gastrointestinal Transits In Vivo. Autism Res.

Gu, N., Vervaeke, K., Hu, H., and Storm, J. F. (2005). Kv7/KCNQ/M and HCN/h, but not KCa2/SK channels, contribute to the somatic medium after-hyperpolarization and excitability control in CA1 hippocampal pyramidal cells. The Journal of Physiology 566, 689-715.

Guillemot, F. (2007). Cell fate specification in the mammalian telencephalon. Prog. Neurobiol. 83, 37-52.

(56) References Cited

OTHER PUBLICATIONS

Hawrylycz, M. J., Lein, E. S., Guillozet-Bongaarts, A. L., Shen, E. H., Ng, L., Miller, J. A., van de Lagemaat, L. N., Smith, K. A., Ebbert, A., Riley, Z. L., et al. (2012). An anatomically comprehensive atlas of the adult human brain transcriptome. Nature 489, 391-399.
Heiman, M., Kulicke, R., Fenster, R. J., Greengard, P., and Heintz, N. (2014). Cell type-specific mRNA purification by translating ribosome affinity purification (TRAP). Nat Protoc 9, 1282-1291.
Henthorn, P., Kiledjian, M., and Kadesch, T. (1990). Two distinct transcription factors that bind the immunoglobulin enhancer microE5/kappa 2 motif. Science 247, 467-470.
Huang, J., Yang, Y., Zhao, P., Gerrits, M. M., Hoeijmakers, J. G. J., Bekelaar, K., Merkies, I. S. J., Faber, C. G., Dib-Hajj, S. D., and Waxman, S. G. (2013). Small-Fiber Neuropathy Nav1.8 Mutation Shifts Activation to Hyperpolarized Potentials and Increases Excitability of Dorsal Root Ganglion Neurons. J Neurosci 33, 14087-14097.
Jentsch, T. J. (2000). Neuronal KCNQ potassium channels:physislogy and role in disease. Nat Rev Neurosci 1, 21-30.
Ji, H., Jiang, H., Ma, W., and Wong, W. H. (2011). Using CisGenome to Analyze ChIP-chip and ChIP-seq Data (John Wiley & Sons, Inc.).
Ji, H., Jiang, H., Ma, W., Johnson, D. S., Myers, R. M., and Wong, W. H. (2008). An integrated software system for analyzing ChIP-chip and ChIP-seq data. Nat Biotechnol 26, 1293-1300.
Kemenes, I., Marra, V., Crossley, M., Samu, D., Staras, K., Kemenes, G., and Nowotny, T. (2011). Dynamic clamp with StdpC software. Nat Protoc 6, 405-417.
Langevin, L. M., Mattar, P., Scardigli, R., Roussigne, M., Logan, C., Blader, P., and Schuurmans, C. (2007). Validating in utero electroporation for the rapid analysis of gene regulatory elements in the murine telencephalon. Dev. Dyn. 236, 1273-1286.
Langmead, B., and Salzberg, S. L. (2012). Fast gapped-read alignment with Bowtie 2. Nat Methods 9, 357-359.
Lein, E. S., Hawrylycz, M. J., Ao, N., Ayres, M., Bensinger, A., Bernard, A., Boe, A. F., Boguski, M. S., Brockway, K. S., Byrnes, E. J., et al. (2007). Genome-wide atlas of gene expression in the adult mouse brain. Nature 445, 168-176.
Lorenzon, N. M., and Foehring, R. C. (1995). Alterations in intracellular calcium chelation reproduce developmental differences in repetitive firing and afterhyperpolarizations in rat neocortical neurons. Developmental Brain Research 84, 192-203.
Maher, B. J., and Loturco, J. J. (2012). Disrupted-in-Schizophrenia (DISC1) Functions Presynaptically at Glutamatergic Synapses. PLoS ONE 7, e34053.
Maher, B. J., and Westbrook, G. L. (2005). SK channel regulation of dendritic excitability and dendrodendritic inhibition in the olfactory bulb. J Neurophysiol 94, 3743-3750.
Massari, M. E., and Murre, C. (2000). Helix-Loop-Helix Proteins: Regulators of Transcription in Eucaryotic Organisms. Mol Cell Biol 20, 429-440.
McCleskey, E. W., and Gold, M. S. (2003). Ion Channels of Nociception. Http://Dx.Doi.org/10.1146/Annurev.Physiol.61.1.835 61, 835-856.
Nowotny, T., Szücs, A., Pinto, R. D., and Selverston, A. I. (2006). StdpC: A modern dynamic clamp. J Neurosci Methods 158, 287-299.
Oh, M. M., and Disterhoft, J. F. (2014). Increased Excitability of Both Principal Neurons and Interneurons during Associative Learning. Neuroscientist 1073858414537382.
Powell, L. M., and Jarman, A. P. (2008). Context dependence of proneural bHLH proteins. Curr Opin Genet Dev 18, 411-417.
Quednow, B. B., Ettinger, U., Mossner, R., Rujescu, D., Giegling, I., Collier, D. A., Schmechtig, A., Kuhn, K.-U., Moller, H.-J., Maier, W., et al. (2011). The Schizophrenia Risk Allele C of the TCF4 rs9960767 Polymorphism Disrupts Sensorimotor Gating in Schizophrenia Spectrum and Healthy Volunteers. Journal of Neuroscience 31, 6684-6691.
Ran, F. A., Hsu, P. D., Lin, C.-Y., Gootenberg, J. S., Konermann, S., Trevino, A. E., Scott, D. A., Inoue, A., Matoba, S., Zhang, Y., et al. (2013). Double Nicking by RNA-Guided CRISPR Cas9 for Enhanced Genome Editing Specificity. Cell 154, 1380-1389.
Sah, P., and Louise Faber, E. S. (2002). Channels underlying neuronal calcium-activated potassium currents. Prog. Neurobiol. 66, 345-353.
Santini, E., Quirk, G. J., and Porter, J. T. (2008). Fear conditioning and extinction differentially modify the intrinsic excitability of infralimbic neurons. Journal of Neuroscience 28, 4028-4036.
Satterthwaite, F. E. (1946). An approximate distribution of estimates of variance components. Biometrics 2, 110-114. Schizophrenia Psychiatric Genome-Wide Association Study (GWAS) Consortium (2011). Genome-wide association study identifies five new schizophrenia loci. Nat Genet 43, 969-976.
Schizophrenia Working Group of the Psychiatric Genomics Consortium (2014). Biological insights from 108 schizophrenia-associated genetic loci. Nature 511, 421-427.
Schulz, D. J. (2006). Plasticity and stability in neuronal output via changes in intrinsic excitability: it"s what" s inside that counts. J Exp Biol 209, 4821-4827.
Sepp, M., Kannike, K., Eesmaa, A., Urb, M., and Timmusk, T. (2011). Functional Diversity of Human Basic Helix-Loop-Helix Transcription Factor TCF4 Isoforms Generated by Alternative 5' Exon Usage and Splicing. PLoS ONE 6, e22138.
Sepp, M., Pruunsild, P., and Timmusk, T. (2012). Pitt-Hopkins syndrome-associated mutations in TCF4 lead to variable impairment of the transcription factor function ranging from hypomorphic to dominant-negative effects. Hum Mol Genet.
Soh, H., and Tzingounis, A. V. (2010). The specific slow afterhyperpolarization inhibitor UCL2077 is a subtype-selective blocker of the epilepsy associated KCNQ channels. Mol Pharmacol 78, 1088-1095.
Sweatt, Pitt Hopkins Syndrome: Intellectual disability due to loss of TCF4-regulated gene transcription. Exp. Mol. Med. (May 3, 2013) vol. 45, No. e21, pp. 1-55.
Yang et al., Blocking SCN10A channels in heart reduces late sodium current and is antiarrythmic. Cir. Res. (Jul. 20, 2012) vol. 111, No. 3, pp. 332-32.
Bustos et al., Beta-catenin regulates KCNQ1 potassium channel expression in colon cancer cells. The Physiological Society of Proceeding (2015), Abstract ONLY.
Glassock, Genomic biomarkers of SUPED in brain and heart. Epilepsy Behav. (Sep. 2014) vol. 38, pp. 172-179.
Maher, B. J. and Loturco, J. J. (2012). In Utero Electroporation for Cellular Transgenesis in the Developing Mammalian Forebrain. In Neuromethods, A. Morozov, ed. (Totowa, N.J. Humana Press), pp. 113-128.

* cited by examiner

FIGS. 1A-1D
A.
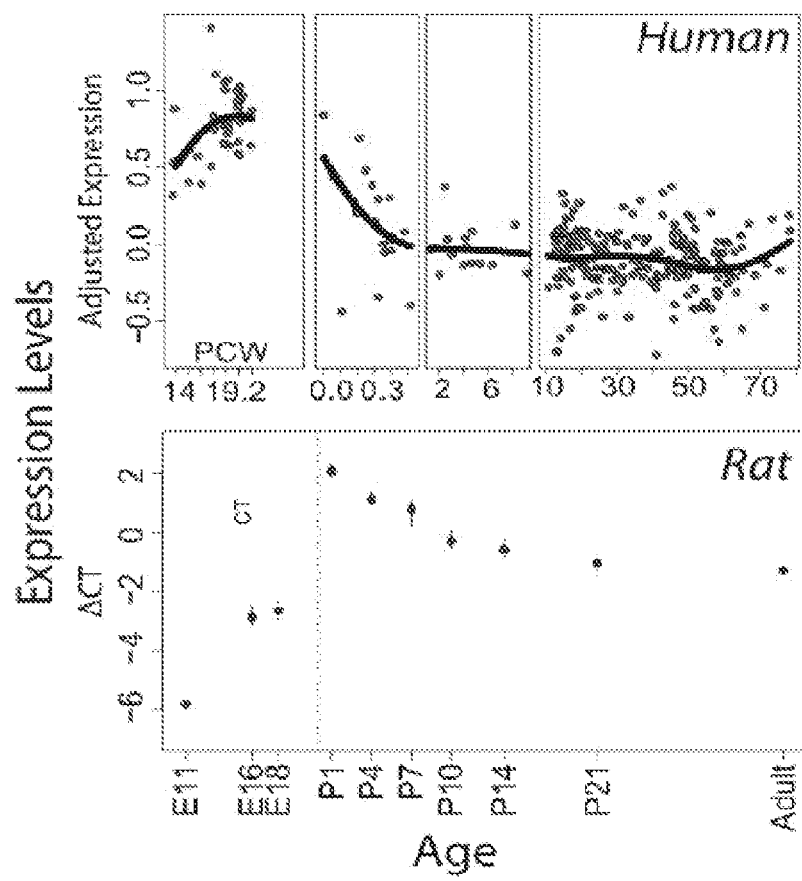
B.
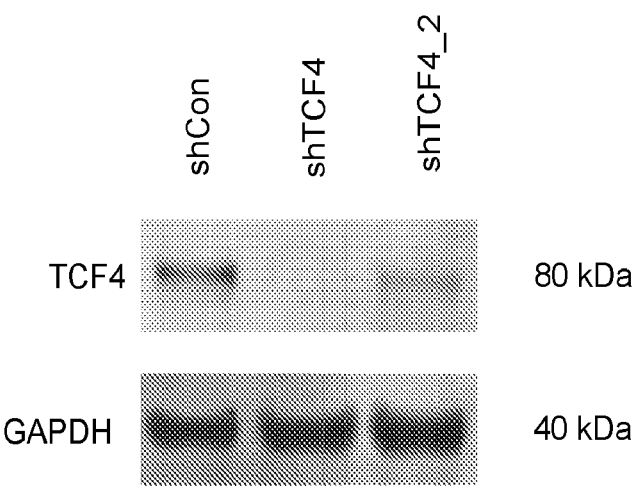

FIGS. 1A-1D (Cont'd)
C.
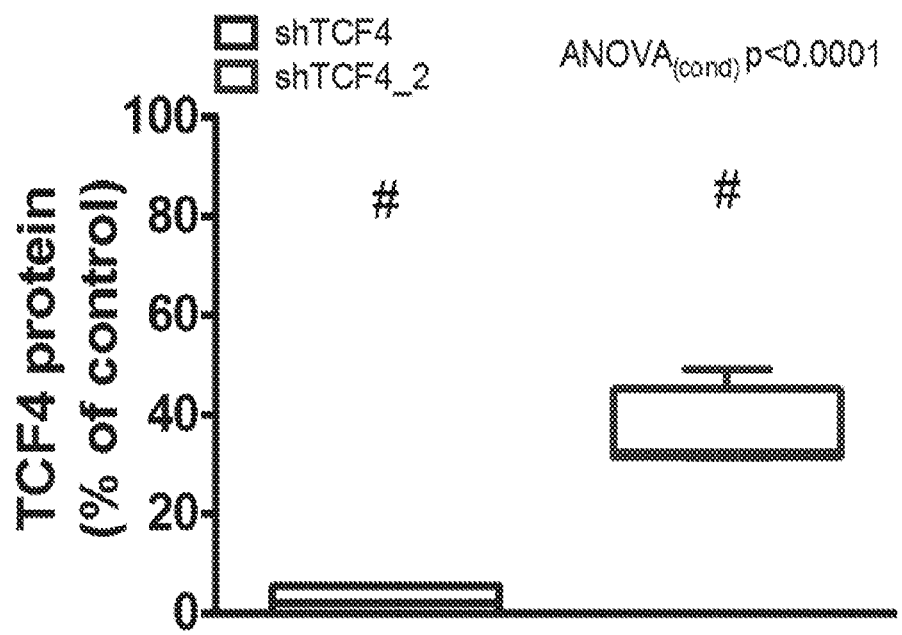
D.
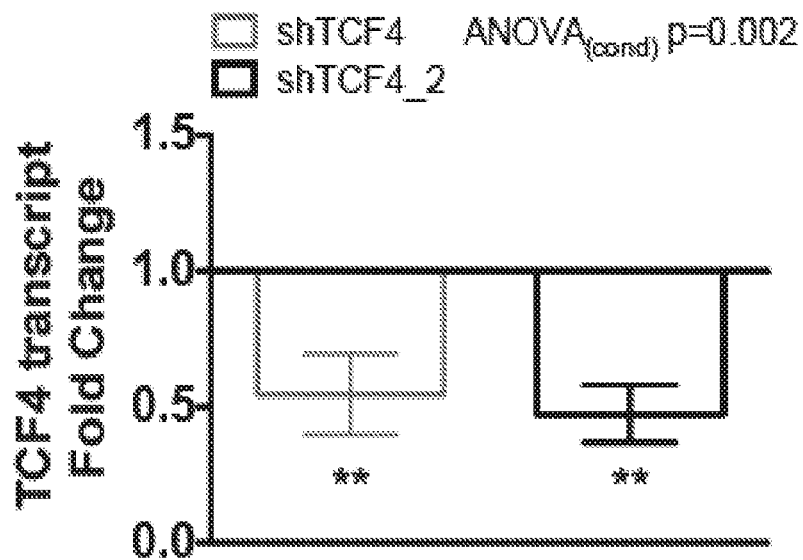

FIGS. 2A-2F
A.
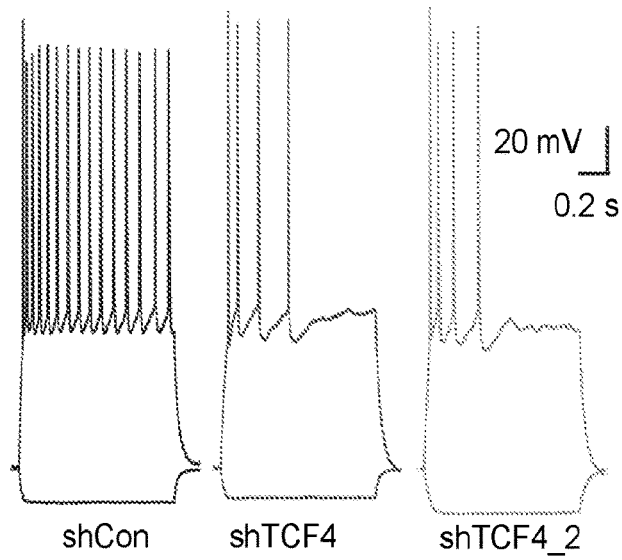
B.
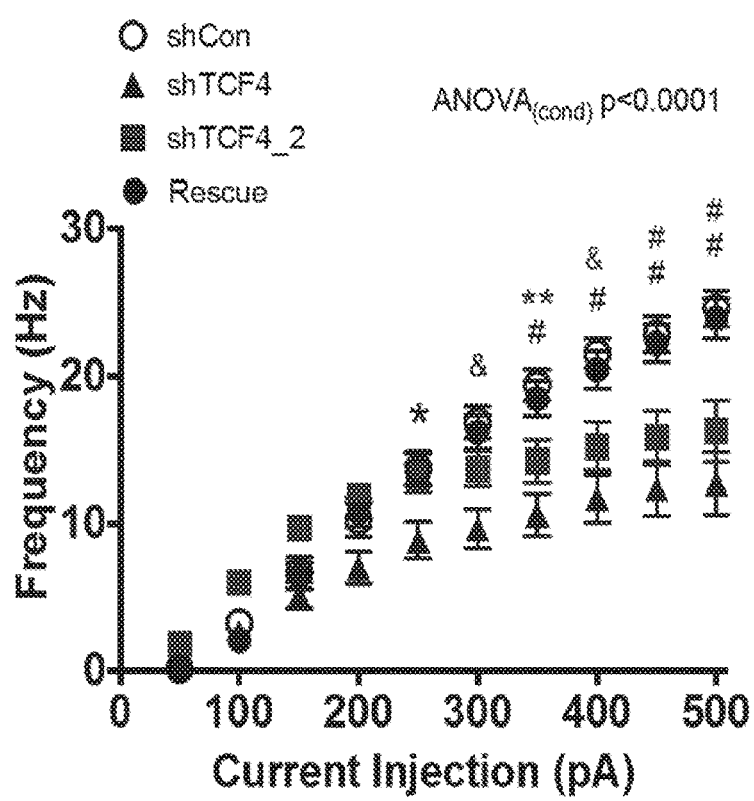

FIGS. 2A-2F (Cont'd)
C.
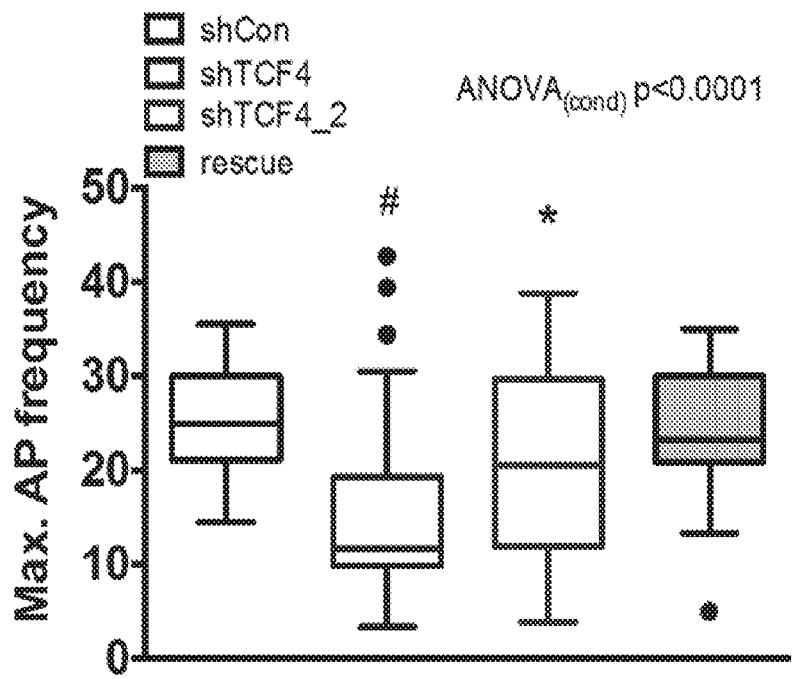
D.
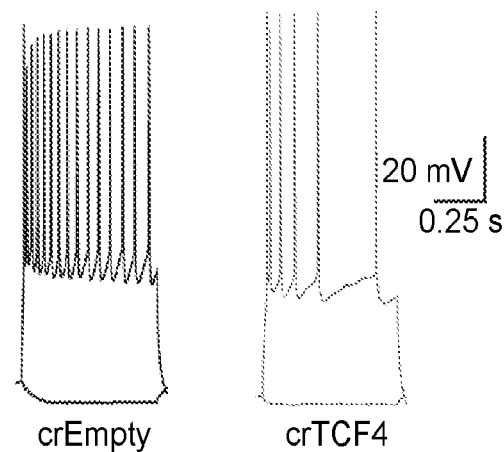

FIGS. 2A-2F (Cont'd)
E.
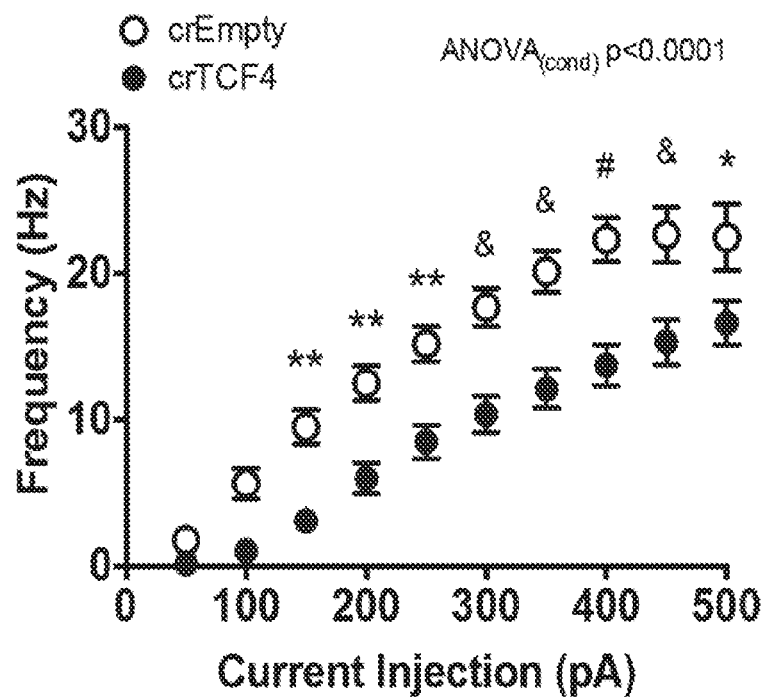
F.
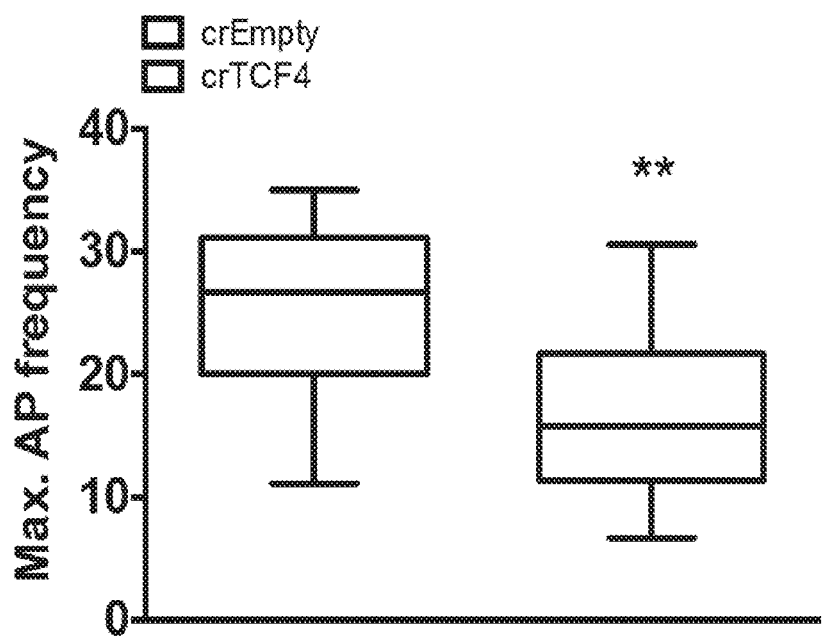

FIGS. 3A-3I
A.
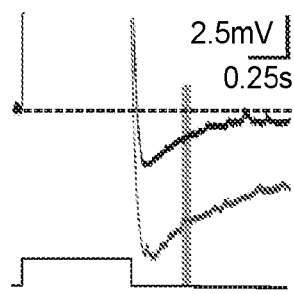
B.
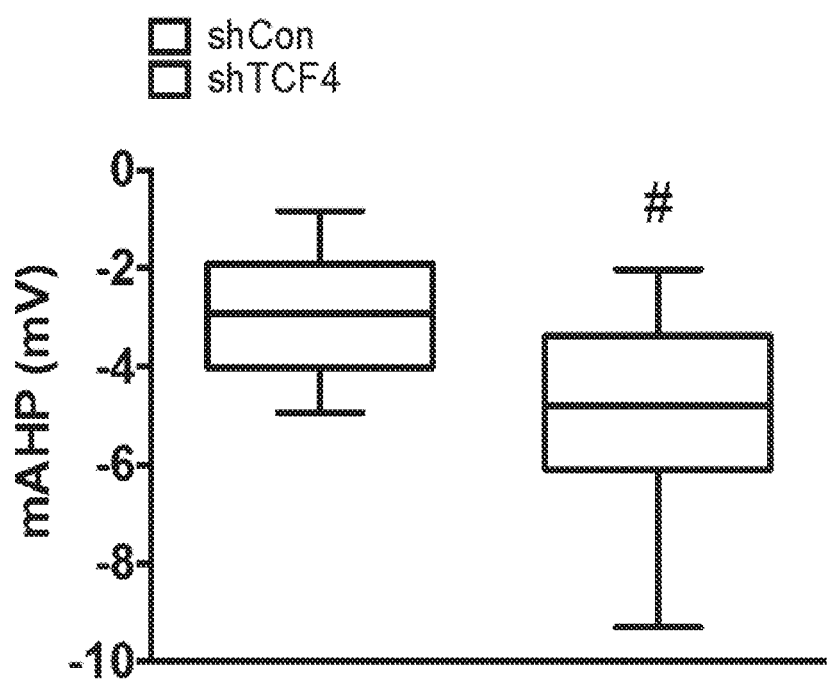

FIGS. 3A-3I (Cont'd)
C.
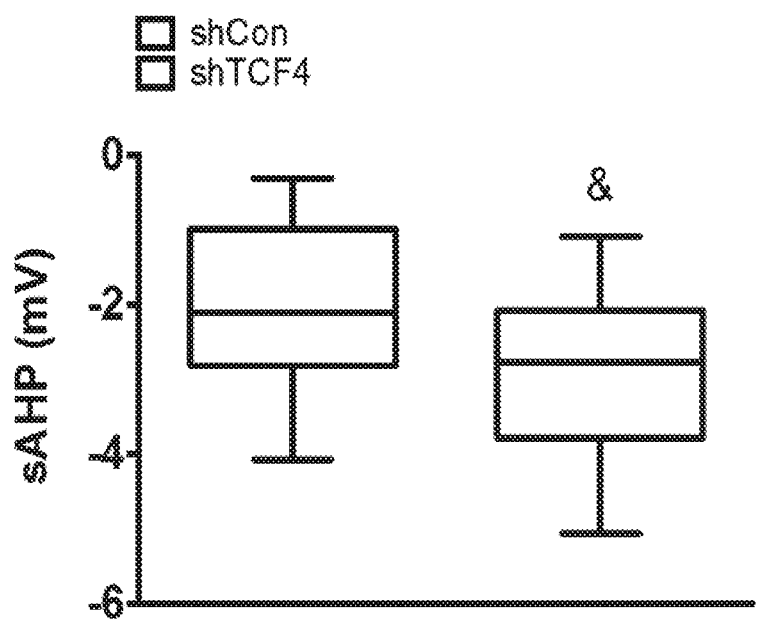
D.
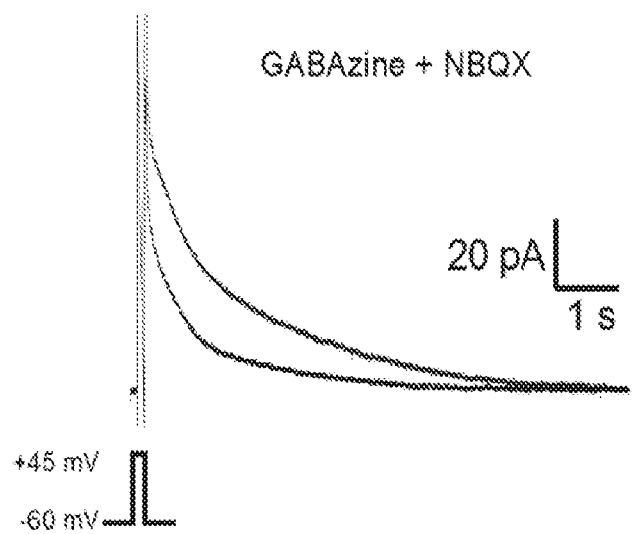

FIGS. 3A-3I (Cont'd)
E.
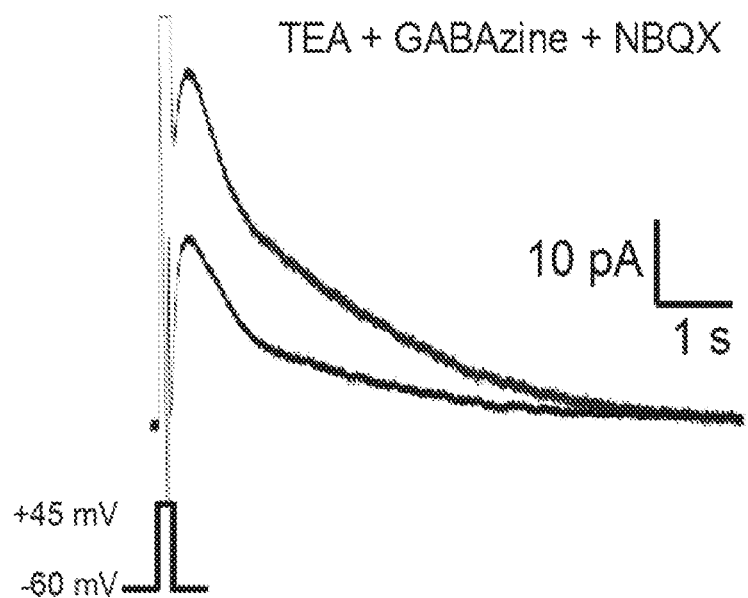
F.
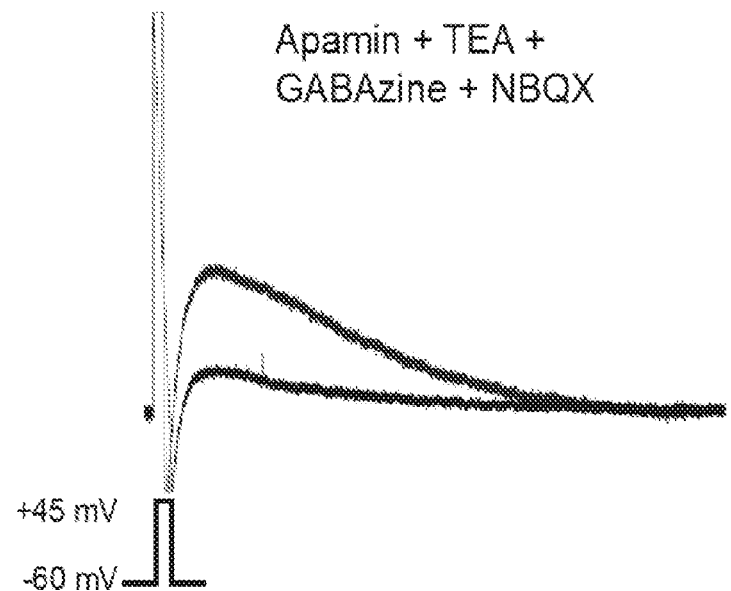

FIGS. 3A-3I (Cont'd)
G.
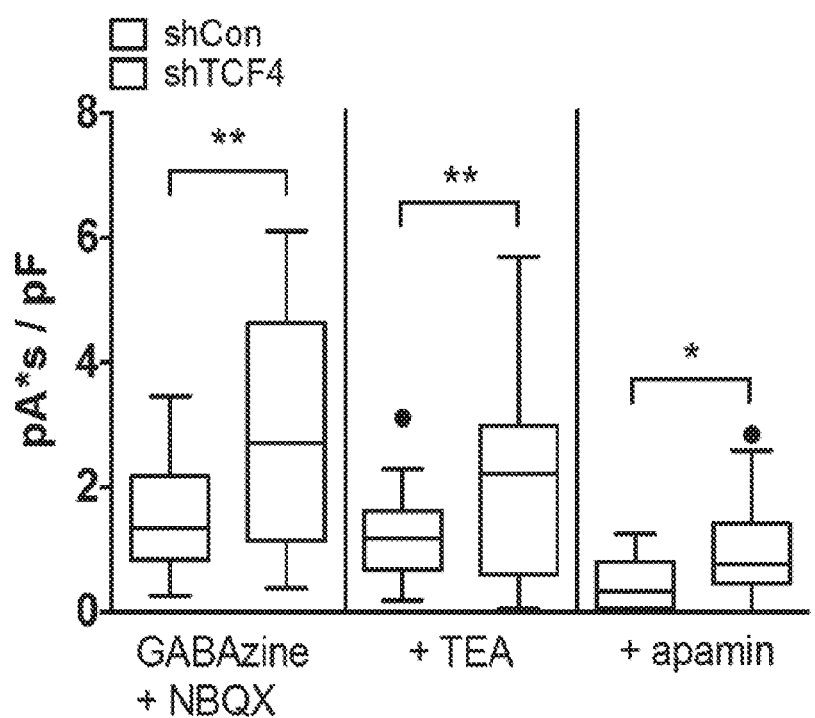
H.
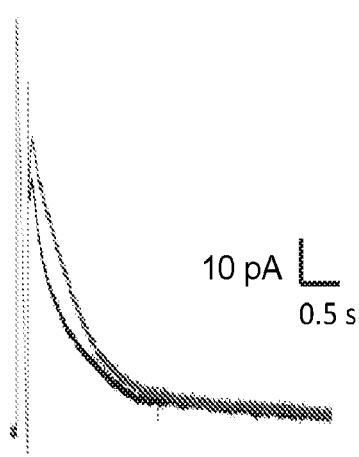

FIGS. 4A-4C
A.
B.
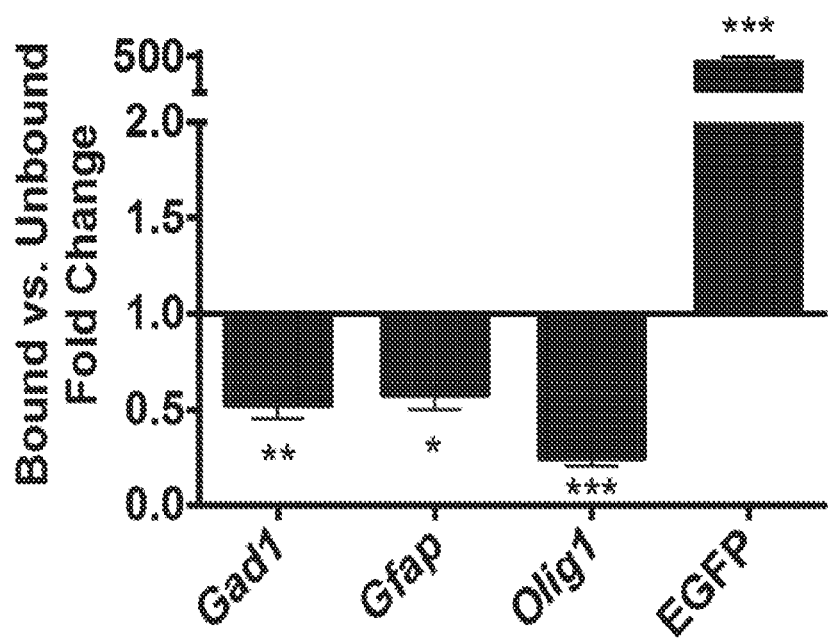

FIGS. 4A-4C (Cont'd)
C.
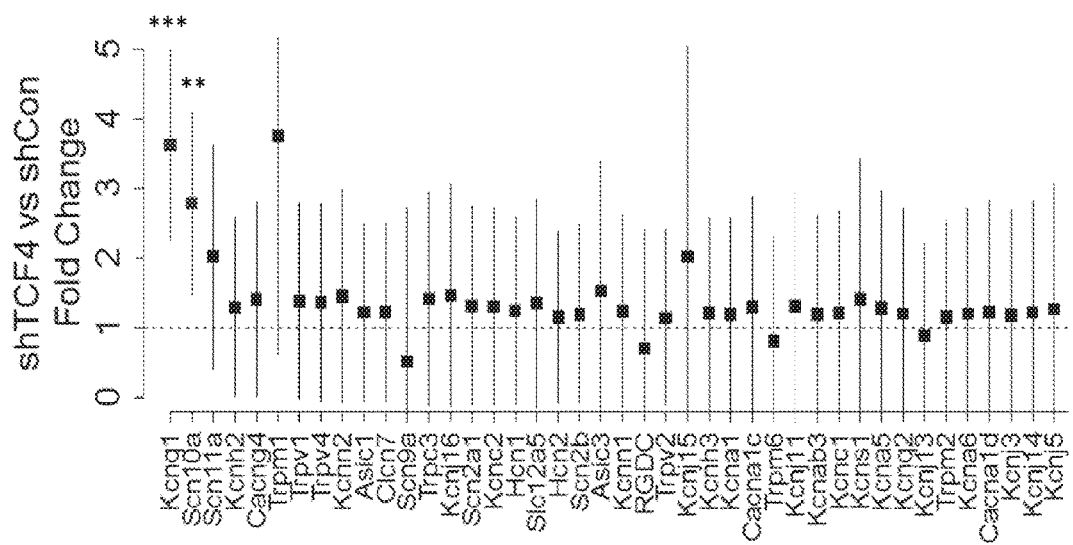
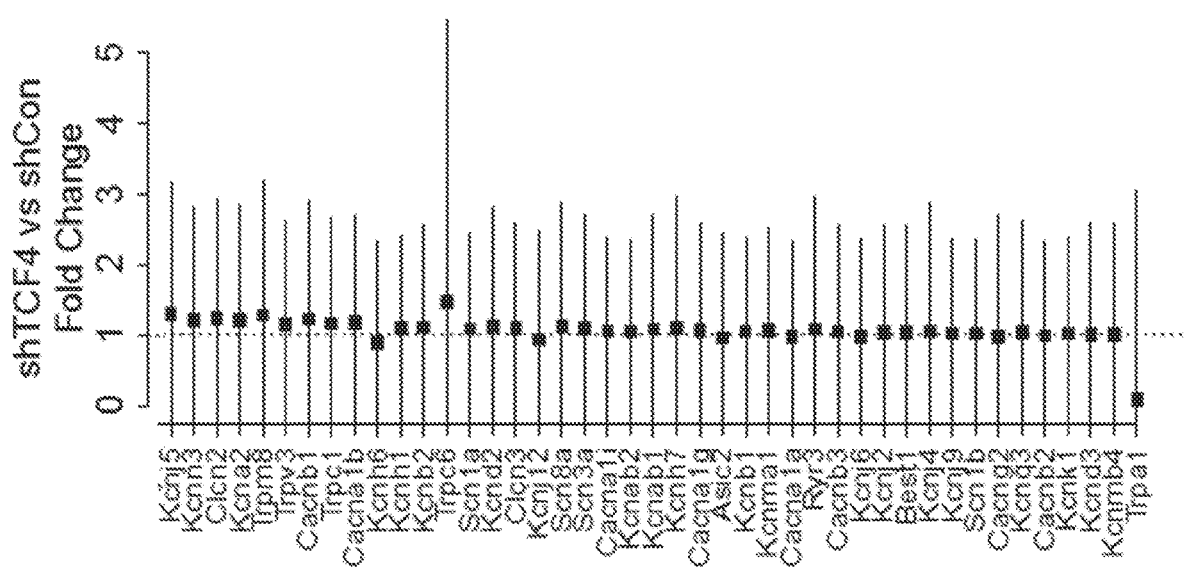

A.

B.

C.

D.

E.

F.

G.

H.

shTCF4　　　　+ JNJ 303

I.

J.

K.

L.

M.

N.

FIGS. 6A-6G
A.
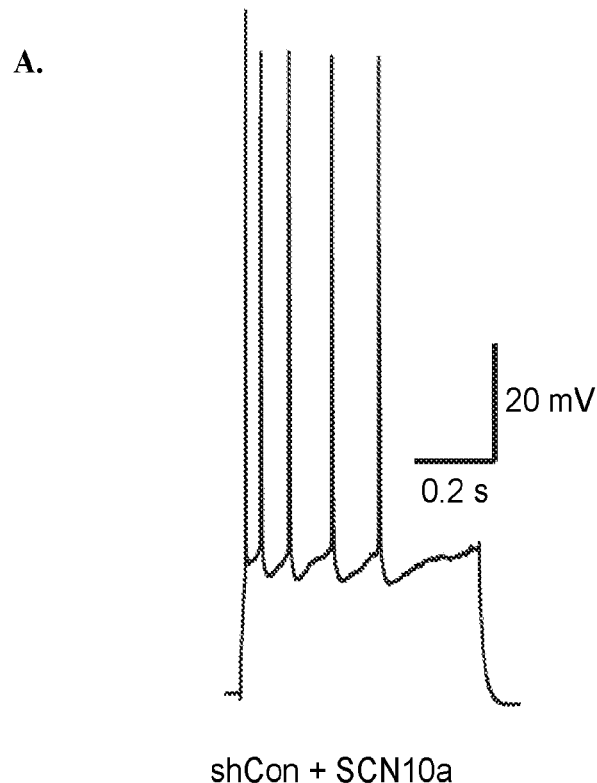
shCon + SCN10a
B.
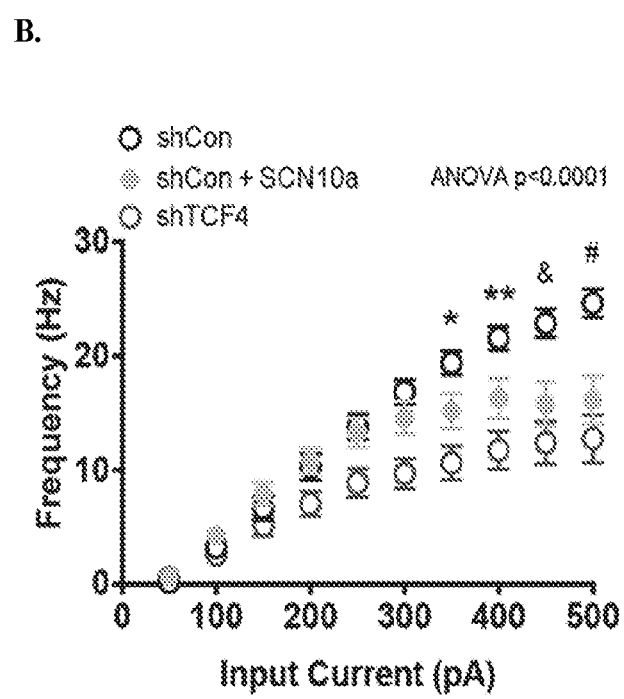

FIGS. 6A-6G (Cont'd)
C.
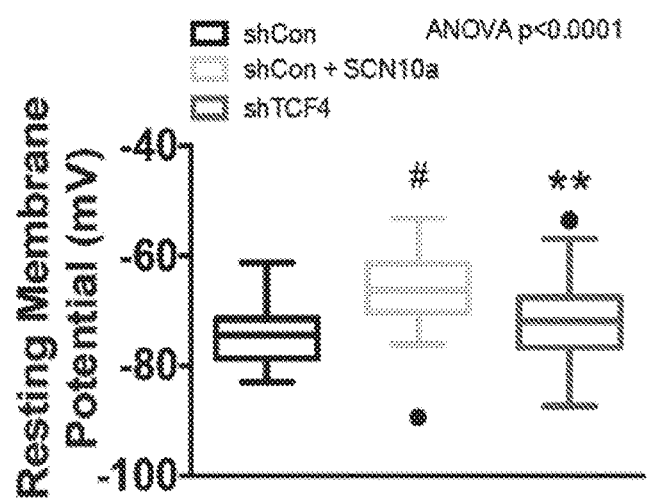
D.
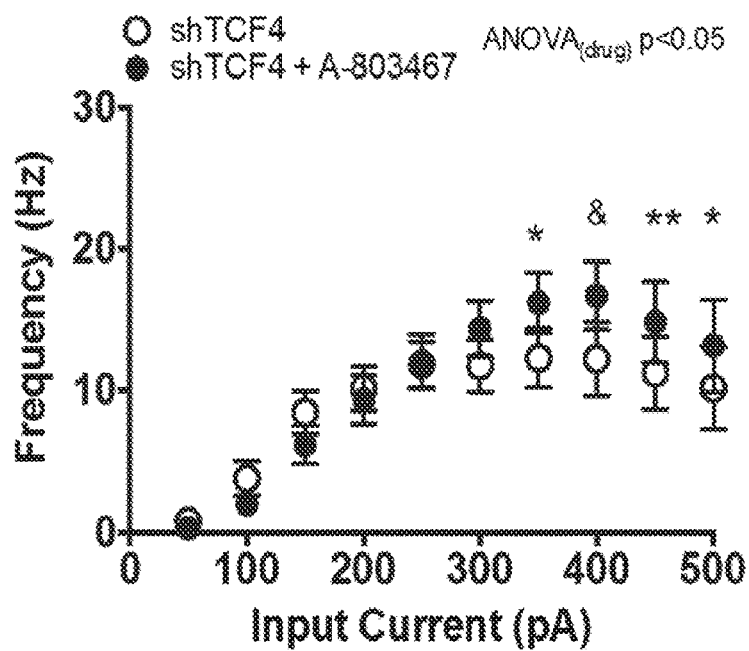

FIGS. 6A-6G (Cont'd)
E.
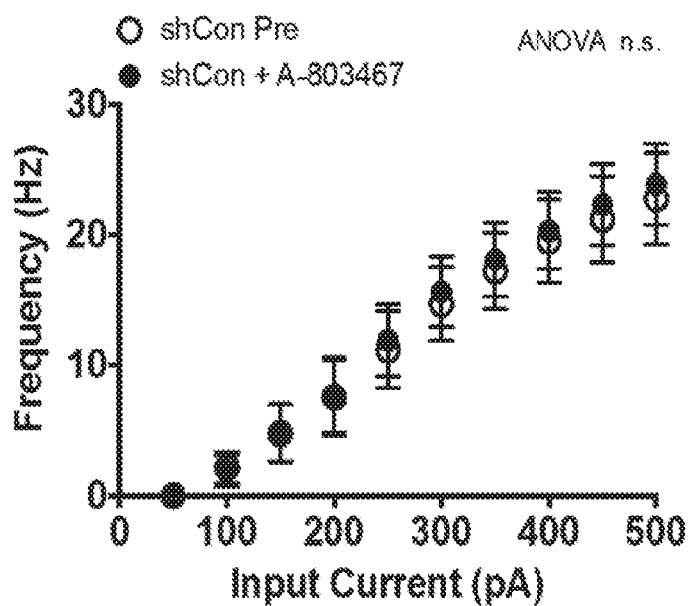
F.
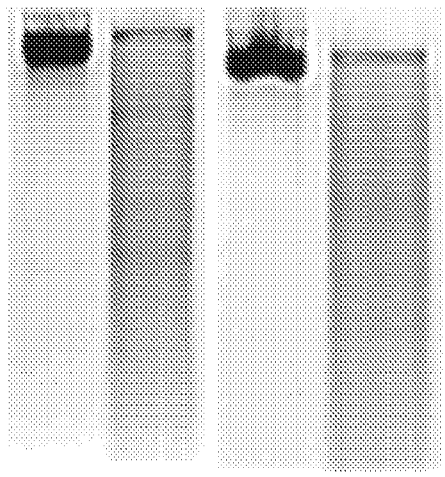

G.

FIGS. 7A-7I
A.
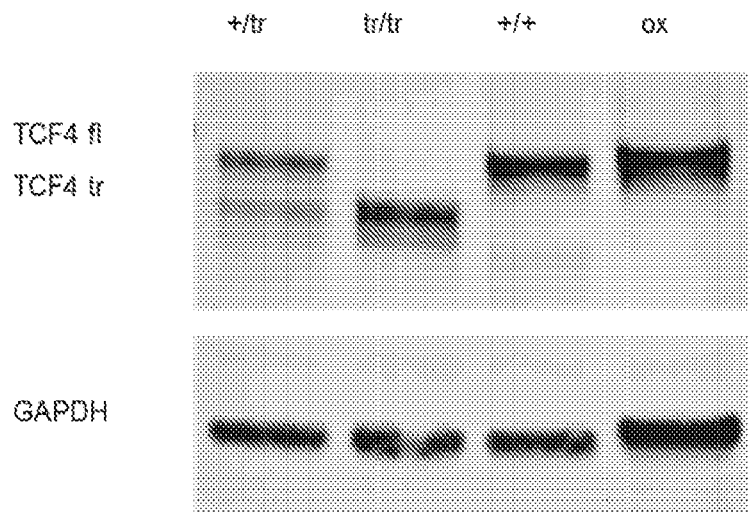
B.
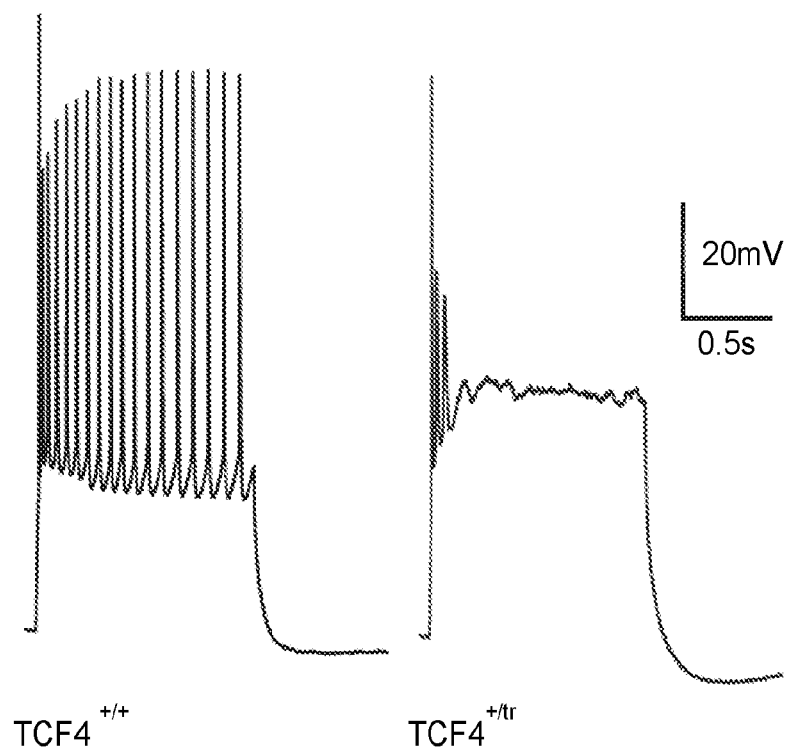

FIGS. 7A-7I (Cont'd)
C.
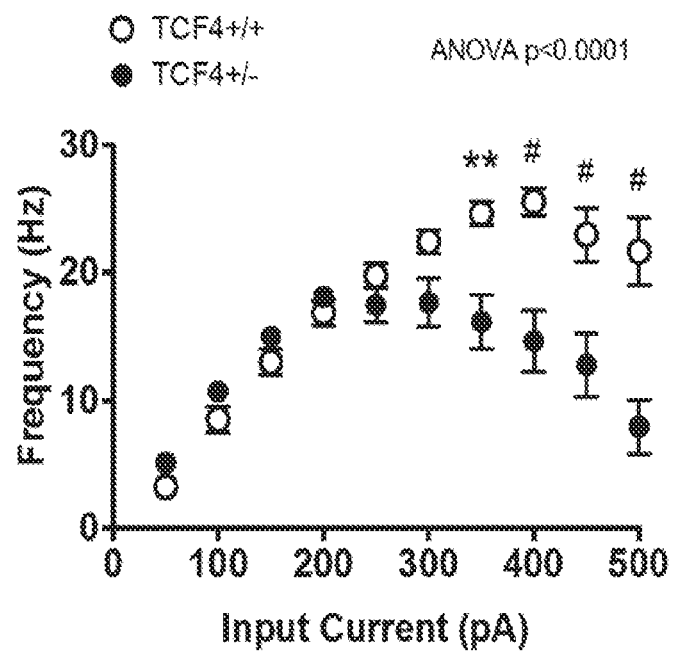
D.
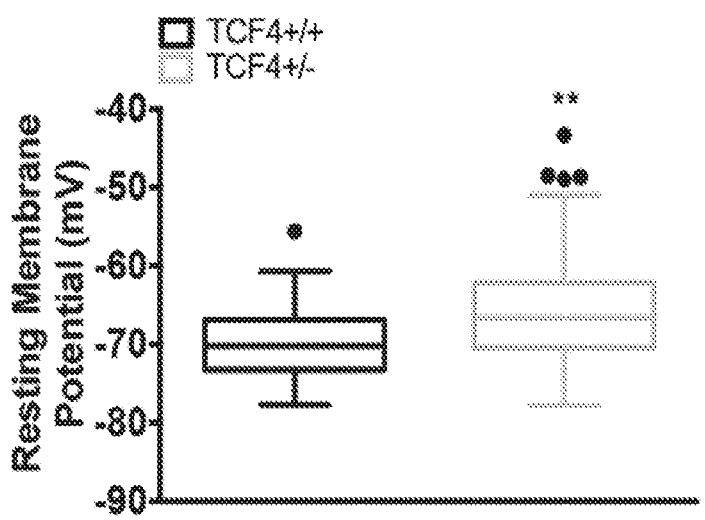

FIGS. 7A-7I (Cont'd)
E.
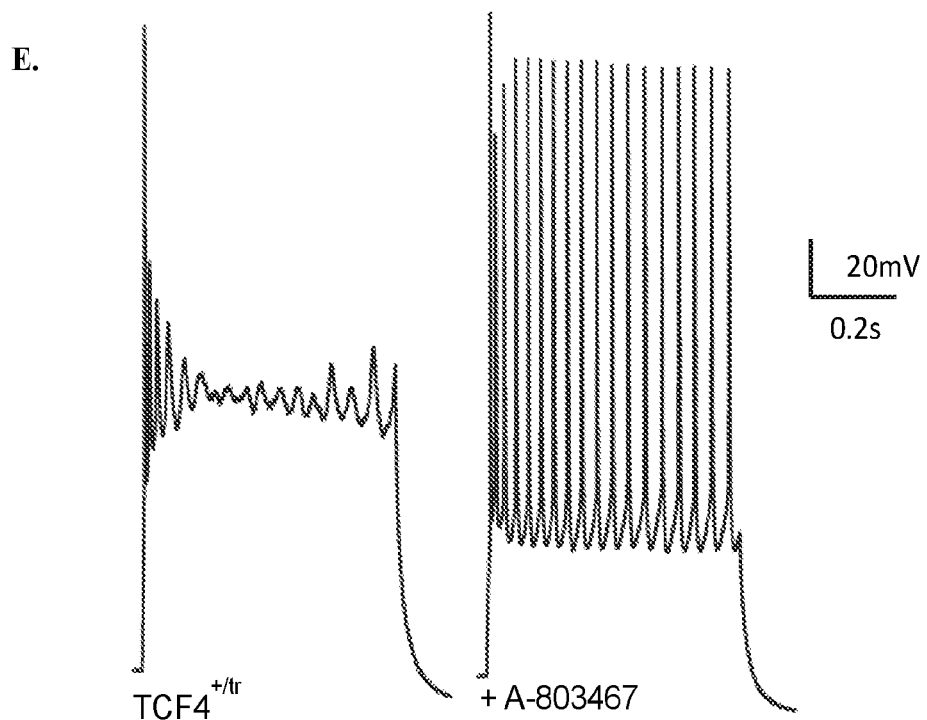
F.
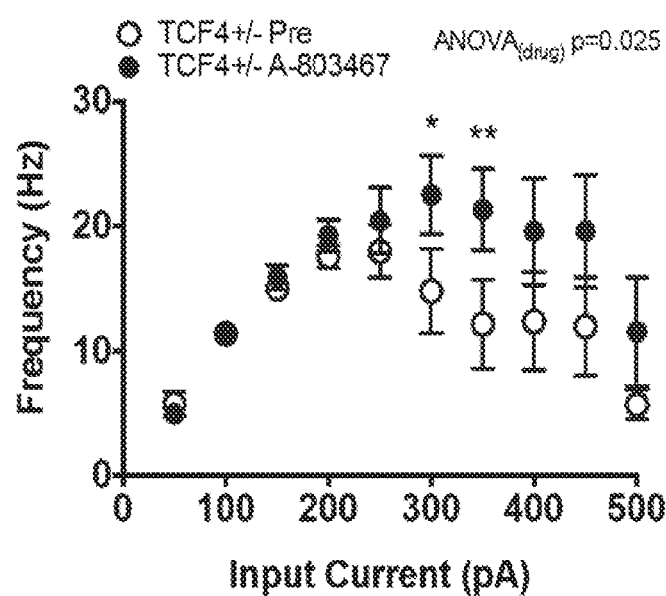

FIGS. 7A-7I (Cont'd)
G.
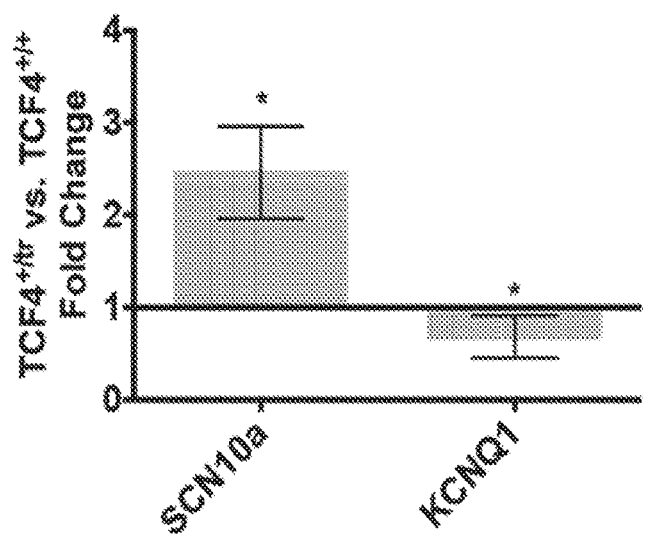
H.
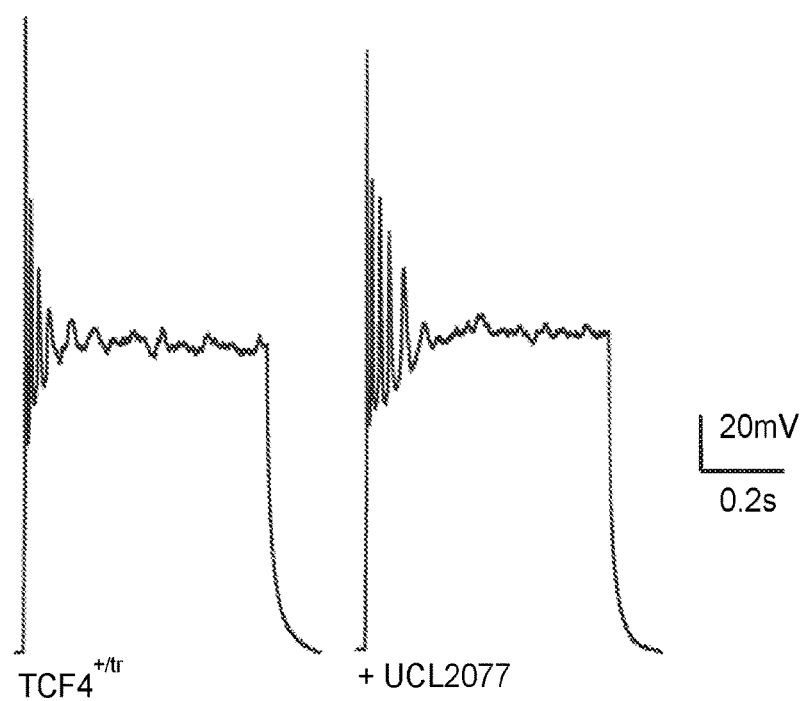

| Species Condition | Rattus norvegicus shCon | shTCF4 | shTCF4_2 | Rattus norvegicus cEmpty | chTCF4 | Mus musculus TCF4+/+ | TCF4+/- |
|---|---|---|---|---|---|---|---|
| Resting Membrane Potential (mV) | -74.6+/-0.7 ANOVA P<0.0001 | -71.9+/-0.8 P=0.0097 | -65.9+/-1.1 P<0.0001 | -72.9+/-1.2 | -70.8+/-0.8 P=0.308 | -69.8+/-0.6 | -65.1+/-1.2 P=0.004 |
| Capacitance (pF) | 35.2+/-0.8 ANOVA P<0.0001 | 37.1+/-0.7 P<0.0001 | 24.3+/-0.9 P=0.32 | 44.6+/-1.1 | 26.7+/-1.1 P=0.72 | 16.9+/-0.5 | 19.3+/-0.7 P=0.68 |
| Membrane Resistance (Mohm) | 96.9+/-4.6 ANOVA P<0.0001 | 78.3+/-2.9 P=0.46 | 132.6+/-9.3 P=0.0002 | 92.7+/-3.6 | 95.8+/-6.1 P=0.651 | 99.1+/-8.2 | 112.0+/-7.0 P=0.18 |
| Rheobase | 123.9+/-10.2 ANOVA P<0.0001 | 153.9+/-16.8 P=0.55 | 86.3+/-9.5 P=0.0006 | 85.3+/-10.3 | 100.5+/-11.8 P=0.0001 | 70.9+/-9.4 | 53.9+/-2.9 P=0.26 |
| Action Potential Width (ms) | 2.15+/-0.07 ANOVA P=0.21 | 2.33+/-0.07 P=0.19 | 2.28+/-0.07 P=0.37 | 3.28+/-0.98 | 7.46+/-0.11 P=0.0001 | 2.48+/-0.10 | 2.54+/-0.12 P=0.0076 |
| Action Potential Threshold (mV) | -39.3+/-0.8 ANOVA P=0.062 | -37.9+/-1.49 P=0.99 | -33.5+/-1.3 P=0.096 | -40.7+/-0.9 | -40.7+/-0.7 P=0.66 | -39.6+/-0.4 | -37.9+/-0.3 P=0.036 |
| Action Potential Amplitude from Rest (mV) | 99.9+/-1.8 ANOVA P<0.0001 | 44.6+/-0.9 P=0.0039 | 92.2+/-1.2 P=0.085 | 91.4+/-2.8 | 95.8+/-7.5 P=0.57 | 91.8+/-0.9 | 46.1+/-1.5 P=0.39 |
| Action Potential Amplitude Baseline (mV) | 119.9+/-1.3 ANOVA P<0.0001 | 113.6+/-1.2 P<0.0001 | 113.2+/-1.6 P=0.022 | 113.7+/-2.4 | 118.8+/-1.8 P=0.30 | 112.9+/-1.5 | 113.8+/-2.2 P=0.52 |

FIGS. 10A-10C
A.
shCon 20Hz
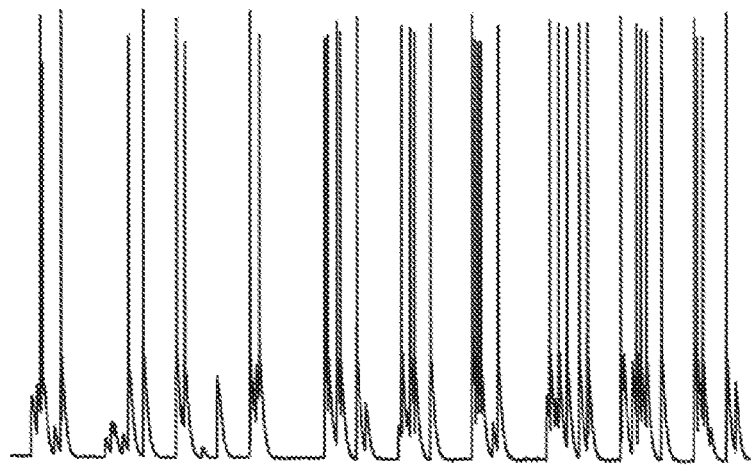
B.
shTCF4 20Hz
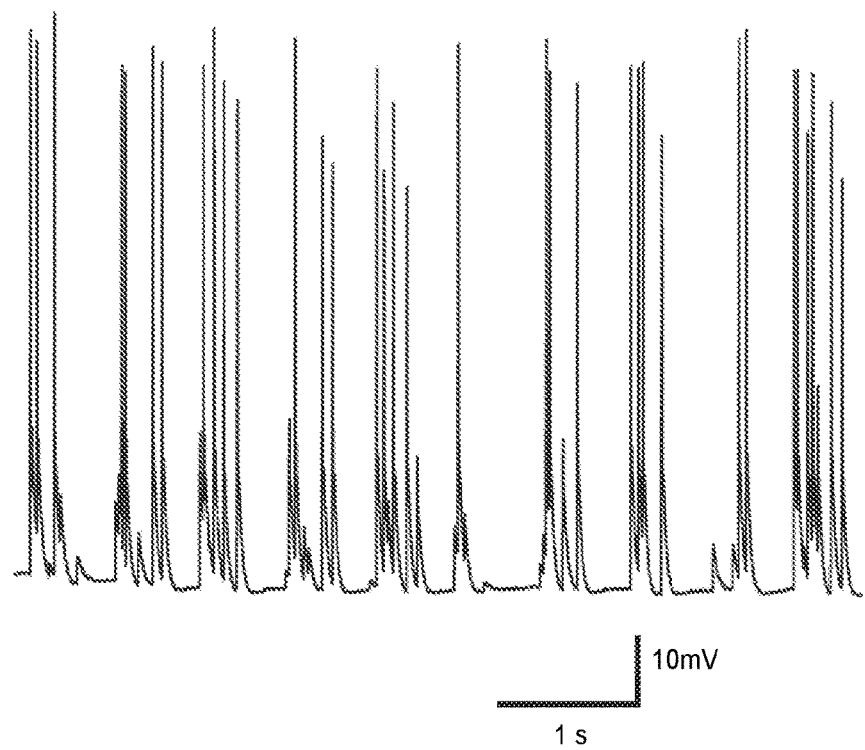

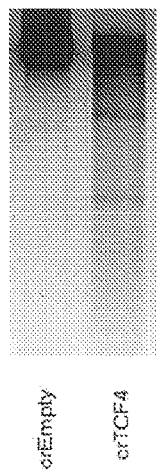

B.

```
GAGCGGAGGATGGCCAATAACGCCCGTGAGCGCCTGAGGGTCCGTGATATCAACG        WT

GAGCGGAGGATGGCCAATAACGCCCGTGAGCGC--GAGGGTCCGTGATATCAACG        Δ2
GAGCGGAGGATGGCCAATAACGCCCGTGAGCGCCTGAGGGTCCGTGATATCAA-        +2
GAGCGGAGGATGGCCAATAACGCCCGTGAGCGCCTGAGGGTCCGTGATATCAAC-       +1
GAGCGGAGGATGGCCCAATAICGCCCGTGAGCGC--GAGGGTCCGTGATATCAAC       Δ1 (Δ2, +1)
GAGCGGAGGATGGCCAATAACG------------------GTCCGTGATATCAACG      Δ17
```

(SEQ ID NOS: 5-10)

C.

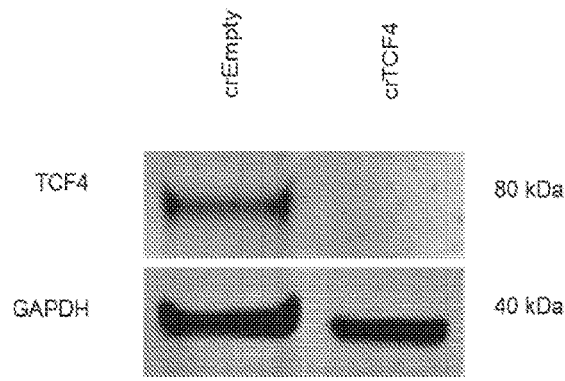

FIGS. 11A-11E (Cont'd)
D.
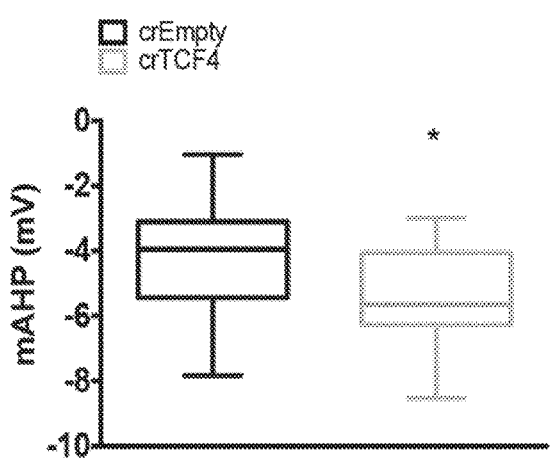
E.
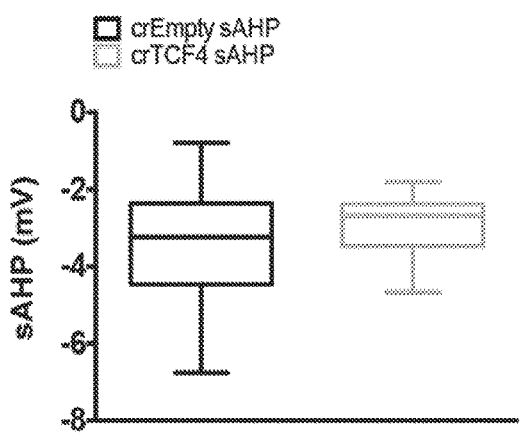

FIGS. 13A-13D
A.
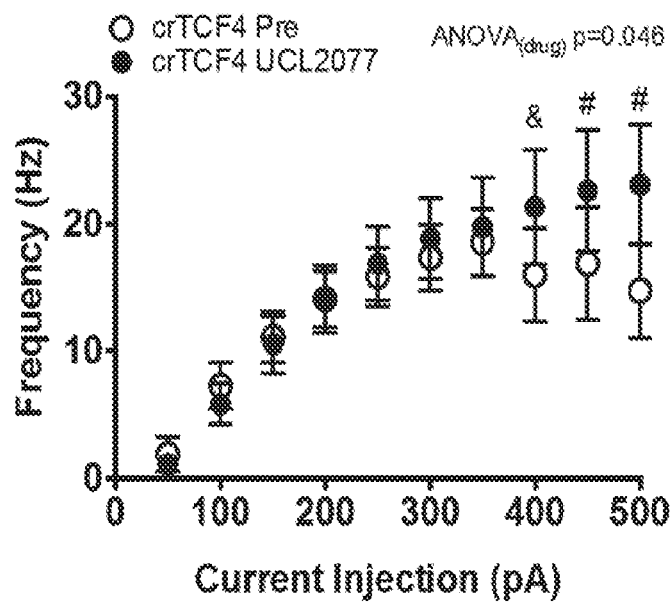
B.
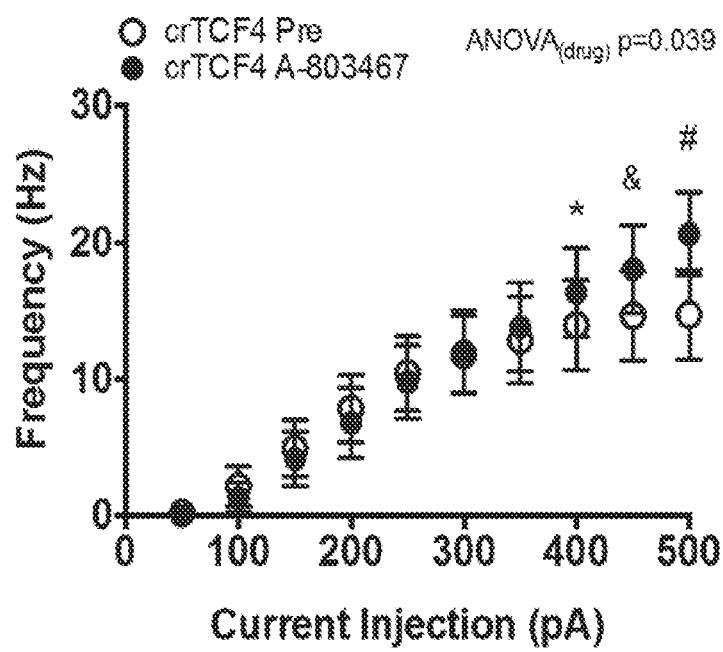

FIGS. 13A-13D (Cont'd)
C.
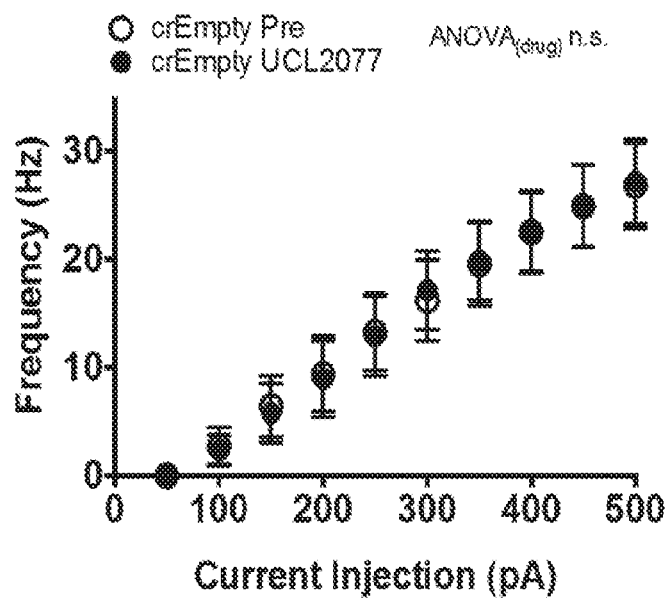
D.
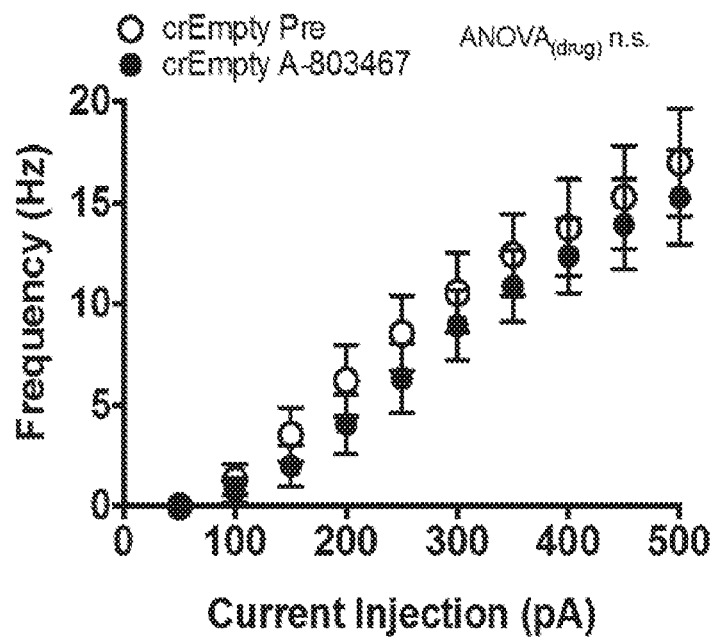

FIG. 14A-14H
A.
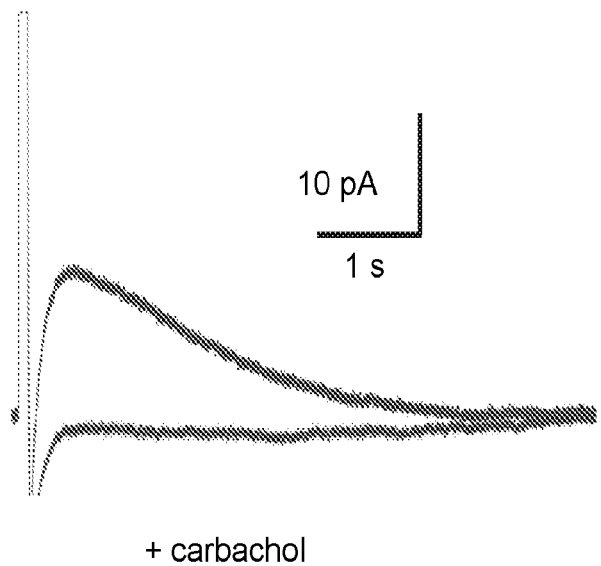
+ carbachol
B.
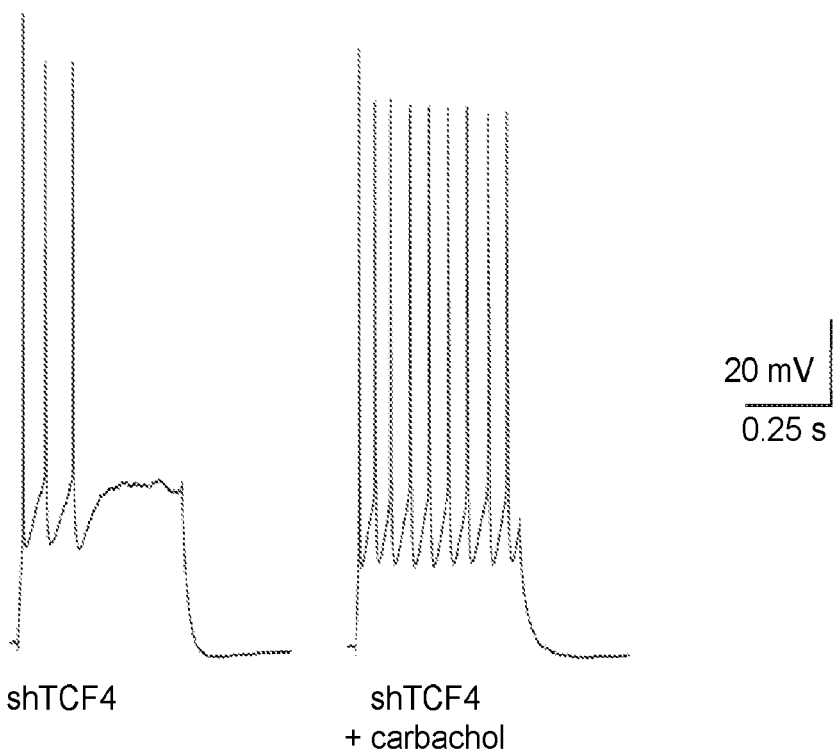
shTCF4    shTCF4
          + carbachol FIG. 14A-14H (Cont'd)
C.
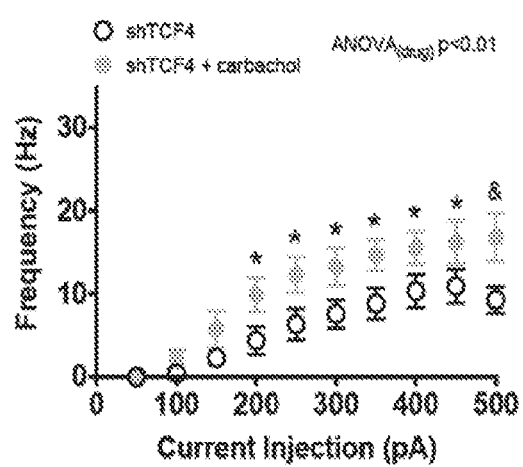
D.
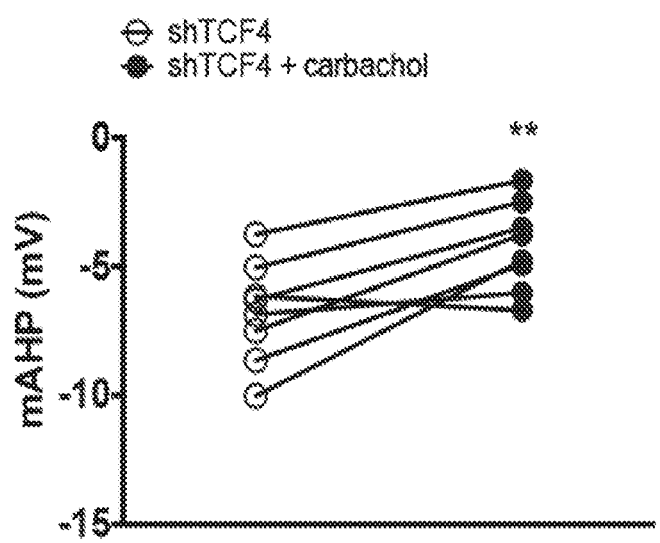

FIG. 14A-14H (Cont'd)
E.
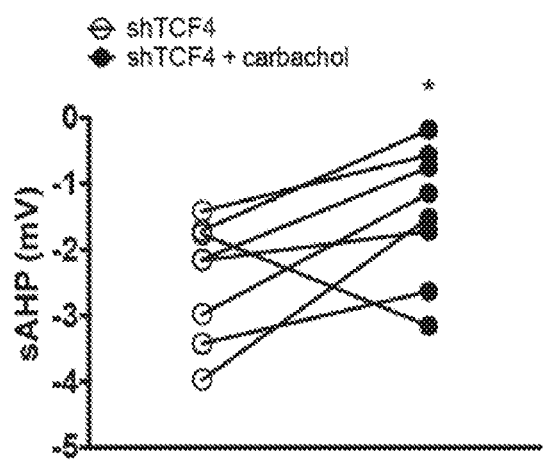
F.
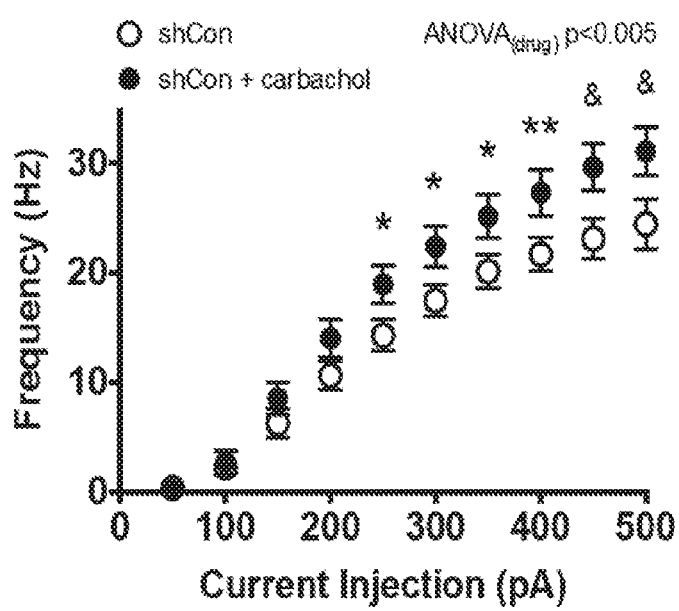

FIG. 14A-14H (Cont'd)
G.
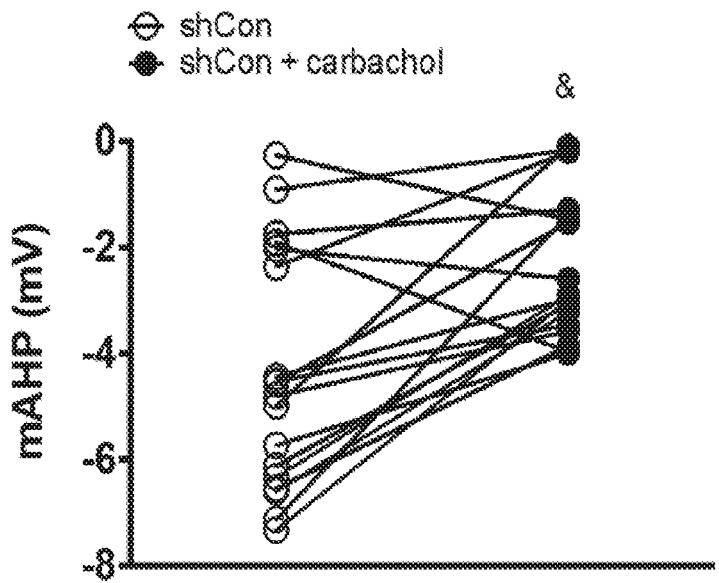
H.
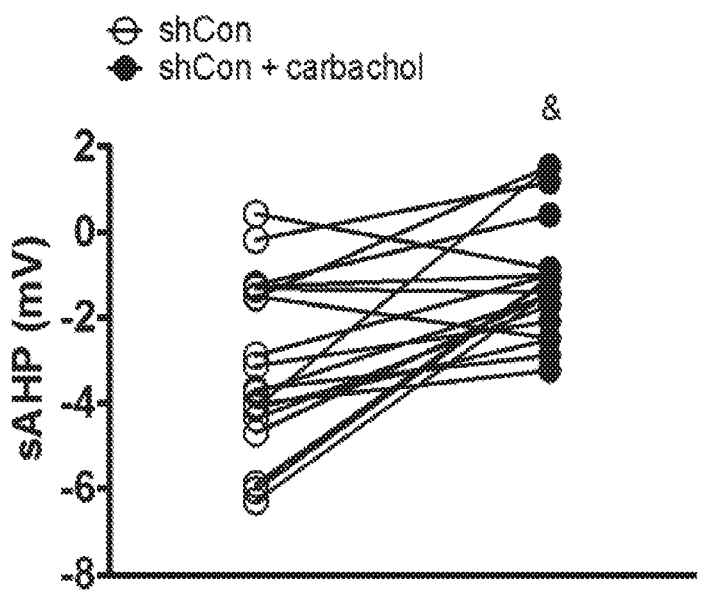

| Peak Coordinates | FDR | Gene | Location | DistFromTSS | #EboxMotif |
|---|---|---|---|---|---|
| chr8:124606700-124606899 | 0.0020 | Scn10a | overlaps exon | 83559 | 1 |
| chr8:124596000-124596099 | 0.0074 | Scn10a | inside intron | 94359 | 1 |
| chr8:124584700-124584799 | 0.0084 | Scn10a | inside intron | 105659 | 1 |
| chr8:124697200-124697299 | 0.0104 | Scn10a | upstream | 6742 | 1 |
| chr1:203431500-203431699 | 0.0013 | Kcnq1 | inside intron | 48099 | 1 |
| chr1:203750400-203750699 | 0.0013 | Kcnq1 | inside intron | 366999 | 1 |
| chr1:203436400-203436949 | 0.0013 | Kcnq1 | inside intron | 52999 | 6 |
| chr1:203766100-203766299 | 0.0013 | Kcnq1 | inside intron | 382699 | 4 |
| chr1:203751250-203751499 | 0.0014 | Kcnq1 | inside intron | 367849 | 2 |
| chr1:203815350-203815599 | 0.0015 | Kcnq1 | downstream | 431949 | 49 |
| chr1:203813900-203814149 | 0.0016 | Kcnq1 | downstream | 430499 | 2 |
| chr1:203822450-203822699 | 0.0031 | Kcnq1 | downstream | 439049 | 1 |
| chr1:203430750-203431049 | 0.0038 | Kcnq1 | inside intron | 47349 | 1 |
| chr1:203765050-203765549 | 0.0041 | Kcnq1 | inside intron | 381649 | 2 |
| chr1:203431200-203431399 | 0.0041 | Kcnq1 | inside intron | 47799 | 3 |
| chr1:203823050-203823149 | 0.0067 | Kcnq1 | downstream | 439649 | 2 |

(SEQ ID NO: 11)

```
                             SEQUENCE LISTING

<160> NUMBER OF SEQ ID NOS: 12

<210> SEQ ID NO 1
<211> LENGTH: 19
<212> TYPE: DNA
<213> ORGANISM: homo sapiens

<400> SEQUENCE: 1
gtttcagcat tcccaatta                                                      19

<210> SEQ ID NO 2
<211> LENGTH: 19
<212> TYPE: DNA
<213> ORGANISM: Homo sapiens

<400> SEQUENCE: 2
agaaactaga cgacgacaa                                                      19

<210> SEQ ID NO 3
<211> LENGTH: 19
<212> TYPE: DNA
<213> ORGANISM: Homo sapiens

<400> SEQUENCE: 3
agttccagta cggctccaa                                                      19

<210> SEQ ID NO 4
<211> LENGTH: 20
<212> TYPE: DNA
<213> ORGANISM: Homo sapiens

<400> SEQUENCE: 4
ataacgcccg tgagcgcctg                                                     20

<210> SEQ ID NO 5
<211> LENGTH: 55
<212> TYPE: DNA
<213> ORGANISM: Homo sapiens

<400> SEQUENCE: 5
gagcggagga tggccaataa cgcccgtgag cgcctgaggg tccgtgatat caacg              55

<210> SEQ ID NO 6
<211> LENGTH: 53
<212> TYPE: DNA
```

```
<213> ORGANISM: Homo sapiens

<400> SEQUENCE: 6
gagcggagga tggccaataa cgcccgtgag cgcgagggtc cgtgatatca acg      53

<210> SEQ ID NO 7
<211> LENGTH: 55
<212> TYPE: DNA
<213> ORGANISM: Homo sapiens

<400> SEQUENCE: 7
gagcggagga tggcccaata acgcccgtga gcgccctgag ggtccgtgat atcaa    55

<210> SEQ ID NO 8
<211> LENGTH: 55
<212> TYPE: DNA
<213> ORGANISM: Homo sapiens

<400> SEQUENCE: 8
gagcggagga tggccaataa cgcccgtgag cgccctgagg gtccgtgata tcaac    55

<210> SEQ ID NO 9
<211> LENGTH: 53
<212> TYPE: DNA
<213> ORGANISM: Homo sapiens

<400> SEQUENCE: 9
gagcggagga tggcccaata tcgcccgtga gcgcgagggt ccgtgatatc aac      53

<210> SEQ ID NO 10
<211> LENGTH: 38
<212> TYPE: DNA
<213> ORGANISM: Homo sapiens

<400> SEQUENCE: 10
gagcggagga tggccaataa cggtccgtga tatcaacg                        38

<210> SEQ ID NO 11
<211> LENGTH: 59
<212> TYPE: PRT
<213> ORGANISM: Homo sapiens

<400> SEQUENCE: 11

Lys Glu Arg Arg Met Ala Asn Asn Ala Arg Glu Arg Leu Arg Val Arg
 1               5                  10                  15

Asp Ile Asn Glu Ala Phe Lys Glu Leu Gly Arg Met Val Gln Leu His
                20                  25                  30

Leu Lys Ser Asp Lys Pro Gln Thr Lys Leu Leu Ile Leu His Gln Ala
            35                  40                  45

Val Ala Val Ile Leu Ser Leu Glu Gln Gln Val
        50                  55

<210> SEQ ID NO 12
<211> LENGTH: 42
<212> TYPE: PRT
<213> ORGANISM: Homo sapiens
```

```
<400> SEQUENCE: 12

Gly Thr Ala Cys Ser Cys Gly Asn Ser Lys Gly Ile Tyr Trp Phe Tyr
1               5                   10                  15

Arg Pro Ser Cys Pro Thr Asp Arg Gly Tyr Thr Gly Ser Cys Arg Tyr
                20                  25                  30

Phe Leu Gly Thr Cys Cys Thr Pro Ala Asp
            35              40
```

TREATMENT OF NEUROLOGICAL AND NEURODEVELOPMENTAL DISEASES AND DISORDERS ASSOCIATED WITH ABERRANT ION CHANNEL EXPRESSION AND ACTIVITY

GOVERNMENT LICENSE RIGHTS

This invention was made with government support under grant numbers K01MH086050 and R56MH104593-02 awarded by The National Institutes of Health. The government has certain rights in the invention.

FIELD OF THE INVENTION

The invention relates to the treatment of subjects having a neurological or neurodevelopmental disease or disorder associated with the pathophysiological expression of sodium and/or potassium ion channels in neuronal cells of the central nervous system (CNS) by administering one or more therapeutic antagonists of the ion channels to block or suppress the expression and/or activity of these ion channels in CNS neuronal cells. Such pathophysiological ion channel expression in CNS neurons relates to defective or abnormal TCF4 transcription factor gene expression and/or protein function, as the expression of at least the sodium ion channel SCN10a in CNS neurons, rather than peripheral nervous system neurons, has been newly found to be regulated by TCF4. In particular, the SCN10a sodium channel and/or the KCNQ1 potassium channel is targeted by selective therapeutic antagonists in the treatment methods.

BACKGROUND OF THE INVENTION

Neurological and neurodevelopmental diseases and disorders including schizophrenia, autism, autism spectrum disorders are chronic and debilitating, with relatively unknown etiology and pathophysiology. Recent progress toward understanding the genetic architecture of these disorders at the population level has led to the identification of many genetic risk factors. However, in most cases the molecular mechanism of risk and the relevant functions of the identified genes are not known and therefore identifying therapeutic targets remains difficult.

Pitt-Hopkins syndrome (PTHS) and 18q syndrome are rare neurodevelopmental disorders characterized by symptoms including intellectual disability, failure to acquire language, deficits in motor learning, hyperventilation, epilepsy, autistic behavior, and gastrointestinal abnormalities (Forrest, M. et al., 2012, *Hum. Mutation*, 33: 1676-1686; Soileau, B. et al., 2014, J. Genet. Couns., 24, 663-674; Sweatt, J. D., 2013, *Exp. Mol. Med.*, 45, e21; Whalen, S. et al., 2012, *Hum. Mutation*, 33, 64-72). PTHS is caused by a variety of mutations in the TCF4 gene (ITF2, SEF2, E2-2), each of which results in TCF4 protein deficiency (Amiel, H. J. et al., 2007, *Am. J Hum. Genet.*, 80, 988-993; Brockschmidt, A. et al., 2011, *Hum. Genet.*, 130, 645-655; Sepp, M. et al., 2012, *Hum. Mol. Genet.*, 21(13):2873-2888; Zweier, C. et al., 2008, *J. Med. Genet.*, 45, 738-744). In addition, single nucleotide polymorphisms (SNPs) in a genomic locus containing TCF4 were among the first to reach genome-wide significance in clinical genome-wide association studies (GWAS) for schizophrenia (Schizophrenia Psychiatric Genome-Wide Association Study (GWAS) Consortium, 2011) and are strongly significant in the most recent GWAS ($p=9.09 \times 10^{-13}$), (Schizophrenia Working Group of the Psychiatric Genomics Consortium, 2014). These neuropsychiatric disorders are each characterized by prominent cognitive deficits, which suggest not only genetic overlap between these disorders but also a potentially overlapping pathophysiology.

TCF4 is a basic helix-loop-helix (bHLH) transcription factor (TF) that forms homo- or heterodimers with itself or other bHLH TFs (Comeliusssen, B., 1991, *J. Virol.*, 65, 6084-6093; Henthorn, P. et al., 1990, *Science*, 247, 467-470). Dimerization of TCF4 allows for recognition of E-box binding sites (motif: CANNTG), and direct DNA binding can result in either repression or activation of transcription depending on the protein complex bound to TCF4 (Massari, M. E. and Murre, C., 2000, *Mol. Cell. Biol.*, 20, 429-440). The TCF4 gene is highly expressed throughout the CNS during human development (de Pontual, L. C. et al., 2009, *Hum. Mutat.*, 669-676), but regulation of its expression and splicing is complex, as multiple alternative transcripts containing different 5' exons and internal splicing have been identified (Sepp, M. et al., 2011, *PloS One*, 6, e22138). The genes regulated downstream of TCF4 are not well understood; this is complicated by the limited specificity of the E-box sequence, as well as context-dependent regulation of TCF4 due to heterodimerization, developmental expression and cell-type specificity (Guillemot, 2007, *Prog. Neurobiol.*, 83, 37-52; Powell, L. M. and Jarman, A. P., 2008, *Curr. Opin. Genet. Dev.*, 18, 411-417).

To develop more targeted approaches to treating neurological and neurodevelopmental diseases and disorders, further details regarding the pathophysiology that results from TCF4 biology, including genetic defects involving TCF4, such as haploinsufficiency, are needed. The present invention provides insights into the problem of pathophysiology stemming from TCF4 haploinsufficiency and TCF4 mutation and offers directed treatments involving the targeting of molecules whose function is altered by a lack of normal TCF4 gene expression and/or TCF4 function in neuronal cells. Accordingly, the present invention provides new and specific targets for treating neurological and neurodevelopmental diseases and disorders, such as Pitt-Hopkins Syndrome, schizophrenia, autism and the like, with fewer chances of nonspecific, off-target and adverse effects.

SUMMARY OF THE INVENTION

The present invention relates to methods of treating and/or reducing the symptoms of a neurological or neurodevelopmental disease and disorder that is associated with the aberrant expression of an ion channel in neuronal cells of the central nervous system (CNS), rather than in neuronal cells of the peripheral nervous system (PNS) where such an ion channel is normally expressed, by administering an effective amount of a therapeutic antagonist of the ion channel to block or suppress its unwanted or aberrant expression and/or activity in neuronal cells of the CNS. The neurological or neurodevelopmental disease or disorder may also be associated with defective or abnormal TCF4 transcription factor gene expression and/or protein function in the neuronal cells, e.g., through mutation or haploinsufficiency, which results in ectopic expression of an ion channel whose activity has been newly found to be regulated by TCF4. Such neurological or neurodevelopmental diseases and disorders encompass, for example, Pitt-Hopkins Syndrome (PTHS), schizophrenia, autism, autism spectrum disorder, etc. As used herein, ectopic expression refers to the expression and/or activity of an ion channel gene or protein in cells and/or tissues in which it is not normally expressed. In the instant case, aberrant, abnormal, or atypical expression or activity of a sodium channel, particularly, of the Nav1.8 subtype and more particularly, SCN10a, and/or a potassium ion channel, particularly, KCNQ1, occurs in CNS neuronal cells, particularly prefrontal cortex cells, rather than in PNS neuronal cells where at least one of the ion channels, e.g., SCN10a, is normally expressed and active. In particular embodiments, the ion channels targeted by the therapeutic antagonists according to the methods are the SCN10a sodium ion channel and/or the KCNQ1 potassium ion channel. The terms "sodium or potassium channel" and "sodium or potassium ion channel" are used interchangeably herein. As will be appreciated by those in the art, the SCN10a sodium channel (sodium channel protein type 10 subunit alpha) is also known in the art by other terms, namely, voltage gated sodium channel; Nav1.8; peripheral nerve sodium channel 3 (PN3); mPN3; SNS; alpha protein channel (APC); type X sodium channel; or alpha subunit sodium channel.

In an aspect, the invention provides a method of treating and/or reducing the symptoms of a neurological or neurodevelopmental disease or disorder that is associated with ectopic expression and/or activity of one or more ion channels in neuronal cells of the CNS rather than in neuronal cells of the PNS where the one or more channels is normally expressed and/or active, in a subject in need, by administering to the subject an effective amount of an antagonist of a sodium channel, or an antagonist of a potassium channel, or a combination of an antagonist of a sodium channel and an antagonist of a potassium channel to treat and/or reduce the symptoms of the neurological or neurodevelopmental disease or disorder. In an embodiment, the neurological or neurodevelopmental disease or disorder is associated with defective or abnormal TCF4 transcription factor gene expression and/or protein function in the neuronal cells, which results in the ectopic expression of one or both of the ion channels in CNS neuronal cells through de-repression of their expression in the CNS cells. In an embodiment, the sodium channel is SCN10a and the potassium channel is KCNQ1. In an embodiment, the antagonist blocks or inhibits the expression and/or activity of the SCN10a sodium ion channel in neuronal cells of the CNS. In an embodiment, the antagonist blocks or inhibits the expression and/or activity of the KCNQ1 potassium ion channel in neuronal cells of the CNS. In an embodiment, the antagonist is ion channel type- or subtype-specific and specifically blocks or inhibits the expression and/or activity of the SCN10a sodium ion channel in neuronal cells of the CNS. In an embodiment, the antagonist is ion channel type- or subtype-specific and specifically blocks or inhibits the expression and/or activity of the KCNQ1 potassium ion channel in neuronal cells of the CNS. In an embodiment, the subject in need has, is suspected of having, or is at risk of (for example, has been identified as having a mutation in TCF4) having such a neurological or neurodevelopmental disease or disorder. In embodiments, the neurological or neurodevelopmental disease or disorder is Pitt-Hopkins Syndrome, schizophrenia, autism, autism spectrum disorder, or 18q syndrome, etc. In an embodiment, an antagonist of a sodium channel, preferably an SCN10a antagonist, is administered to the subject in an effective amount to treat and/or reduce symptoms of the disease or disorder in the subject. In an embodiment, an antagonist of a potassium channel, preferably a KCNQ1 antagonist, is administered to the subject in an effective amount to treat and/or reduce symptoms of the disease or disorder in the subject. In an embodiment, both an antagonist of a sodium channel, preferably an SCN10a antagonist, and an antagonist of a potassium channel, preferably a KCNQ1 antagonist, are administered to the subject. In an embodiment, the one or more ion channel antagonists is administered to enhance its delivery to neuronal cells of the CNS and, optimally, to cross the blood-brain barrier. In an embodiment, the methods involve intrathecal administration. In an embodiment, the methods involve the use of an implantable device or pump that locally delivers drugs, such as an ion channel antagonist, to cells of the CNS. In particular, the invention provides for administration of the one or more ion channel antagonists selectively to the CNS while avoiding or minimizing delivery to the PNS.

In embodiments of methods of the invention, the sodium channel antagonist, preferably a SCN10a antagonist, may be one or more of A-803467 (5-(4-Chlorophenyl)-N-(3,5-dimethoxyphenyl)-2-furancarboxamide), aryl-substituted nicotinamide derivatives of A-803467, PF-01247324 (6-amino-N-methyl-5-(2,3,5-trichlorophenyl)pyridine-2-carboxamide), PF-04531083 (N-[6-amino-5-(2-chloro-5-methoxy-phenyl)-2-pyridyl]-2-methyl-pyrazole-3-carboxamide), PF-6305591 ((2R,3S)-3-amino-3-(5-tert-butyl-1H-benzimidazol-2-yl)-2-methyl-propanamide), PF-04885614 (1-methyl-1-[4-(4-trifluoromethoxy-phenyl)-1H-imidazol-2-yl]-ethylamine), PF-5157147 (3-[[4-[4-(trifluoromethoxy)phenyl]-1H-imidazol-2-yl]methyl]oxetan-3-amine), A-887826 (5-(4-butoxy-3-chlorophenyl)-N-[[2-(4-morpholinyl)-3-pyridinyl]methyl]-3-pyridinecarboxamide), Ambroxol hydrochloride (2-Amino-3,5-dibromo-N-(trans-4-hydroxycyclohexyl)benzylamine), DSP-2230 (2S)-2-[[3-cyclobutyl-5-(3,4,5-trifluorophenoxy)imidazo[4,5-b]pyridin-2-yl]methylamino]propanamide or derivative thereof), vinpocetine, VX-150 (4-(2-(4-fluoro-2-methylphenoxy)-4-(trifluoromethyl)benzamido)-2-oxopyridin-1(2H)-yl)methyl dihydrogen phosphate or a non-pro-drug form thereof or derivative thereof), and APETx2 (SEQ: GTACSCGNSKGIYWFYRPSCPTDR-GYTGSCRYFLGTCC TPAD), (SEQ ID NO: 12). See, e.g., Table 1 for the structures of these compounds. In certain embodiments, the sodium channel antagonists include aryl-substituted nicotinamide derivatives of the above-listed compounds, in particular, A-803467, PF-01247324, PF-04531083, PF-6305591, and VX-150. The methods also include administration of pharmaceutically acceptable salts or hydrates of the foregoing. In other embodiments, the SCN10a channel antagonist is an SCN10a-specific interfering RNA, or a biologic, such as an antagonistic anti-SCN10a antibody, which blocks SCN10a activity as described further herein. In another embodiment, the SCN10a channel antagonist is a Crispr/Cas9 construct to mutate the SCN10a gene. In other embodiments of the method, if an antagonist of KCNQ1 is also administered to the subject, the KCNQ1 antagonist may be one or more of Chromanol 293B (trans-6-cyano-4-(N-ethylsulfonyl-N-methylamino)-3-hydroxy-2,2-dimethyl-chroman), HMR-1556 (N-[(3R,4S)-3,4-Dihydro-3-hydroxy-2,2-dimethyl-6-(4,4,4-trifluorobutoxy)-2H-1-benzopyran-4-yl]-N-methylmethanesulfonamide), UCL2077 (N-Trityl-3-pyridinemethanamine), JNJ303 (2-(4-Chlorophenoxy)-2-methyl-N-[5-[(methylsulfonyl)amino]tricyclo[3.3.1.13,7]dec-2-yl]-propanamide), L-735821(L-7) ((E)-(+)-N-[(3R)-2,3-dihydro-1-methyl-2-oxo-5-phenyl-1H-1,4-benzodiazepin-3-yl]-3-(2,4-dichlorophenyl)-2-propenamide), or fenofibrate (propan-2-yl 2-{4-[(4-chlorophenyl)carbonyl]phenoxy}-2-methylpropanoate) (and pharmaceutically acceptable salts and hydrates of the foregoing); (See, Table 2 for compound structures); a KCNQ1-specific interfering RNA; or a biologic, such as an antagonistic anti-KCNQ1 antibody, which blocks KCNQ1 activity.

In general terms, as used herein, an antagonist or a therapeutic antagonist refers to a molecule, agent, compound, drug, or substance that blocks, inhibits, prevents, suppresses, abrogates, eliminates, or substantially reduces the expression and/or the activity of an ion channel gene and/or its encoded protein in a cell, particularly, a neuronal cell, more particularly, a neuronal cell of the CNS. Preferably, the antagonist is specific for a particular ion channel type or subtype and has minimal or no effects on ion channels of other types or subtypes, thereby resulting in fewer off-target or adverse effects in a subject undergoing treatment. In an embodiment, the antagonist is specific for SCN10a. In an embodiment, the antagonist is specific for KCNQ1.

In another aspect, the invention provides a method of treating and/or reducing the symptoms of a neurological or neurodevelopmental disease or disorder that is associated with abnormal or defective neuronal TCF4 expression and/or function, which, in turn, causes de-repression of expression leading to ectopic expression and/or activity of a sodium channel, or a potassium channel, or both, in neuronal cells of the CNS rather than in neuronal cells of the PNS where the ion channel is typically expressed, in a subject in need, by administering to the subject a therapeutically effective amount of a sodium channel antagonist, a potassium channel antagonist, or a combination of a sodium channel antagonist and a potassium channel antagonist to treat and/or reduce the symptoms of the disease or disorder. In an embodiment, a subject to be treated, e.g., a human patient having a neurological disorder such as PTHS, is tested, prescreened, or diagnosed to determine whether TCF4 expression in the subject is abnormal or defective due to (i) haploinsufficiency of TCF4, in which only one chromosomal copy of the TCF4 gene is mutated, or (ii) mutation(s) in the TCF4 gene which cause(s) truncation of TCF4 resulting in a dominant-negative effect that knocks out TCF4 activity in the subject's CNS neurons. In an embodiment, the subject has TCF4 haploinsufficiency, which is associated with the overexpression of SCN10a that adversely affects AP output in the CNS neurons, and underexpression of KCNQ1; accordingly, the subject is administered an effective amount of an antagonist of SCN10a to treat the neurological disorder. In another embodiment, the subject has a TCF4 mutation resulting from a truncation in which the TCF4 protein functions as a dominant negative, resulting in no TCF4 activity in the subject's CNS cells and overexpression of both the SCN10a and the KCNQ1 channels, with a corresponding reduced AP frequency and amplitude, and increased AHP; accordingly, the subject is administered an antagonist of SCN10a, an antagonist of KCNQ1, or, preferably, a combination of an antagonist of SCN10a and an antagonist of KCNQ1 to treat the neurological disorder.

In embodiments, the subject suffers from, is suspected of having, or is at risk for, the neurological or neurodevelopmental disease or disorder. In an embodiment, the subject suffers from, is suspected of having, or is at risk for, PTHS and its symptoms, which include, for example, intellectual disability, failure to acquire language, deficits in motor learning, hyperventilation, epilepsy, autistic behavior, and gastrointestinal abnormalities. In other embodiments, the subject suffers from, is suspected of having, or is at risk for, autism and its symptoms; autism spectrum disorder and its symptoms; or schizophrenia and its symptoms. In an embodiment, the sodium ion channel is SCN10a, and the antagonist is an SCN10a antagonist or an antagonist of an Nav1.8 sodium channel. In an embodiment, the potassium ion channel is KCNQ1, and the antagonist is a KCNQ1 antagonist. In an embodiment, a therapeutically effective amount of a sodium channel antagonist, preferably an SCN10a antagonist, is administered to the subject. In an embodiment, a therapeutically effective amount of a potassium channel antagonist, preferably a KCNQ1 antagonist, is administered to the subject. In an embodiment, a therapeutically effective amount of a sodium channel antagonist, preferably an SCN10a antagonist, and a therapeutically effective amount of a potassium channel antagonist, preferably a KCNQ1 antagonist, is administered to the subject. In an embodiment, the one or more antagonists are administered in a manner or by a means for optimal delivery to neuronal cells of the CNS, for example, without limitation, by an intrathecal mode of administration or other mode of local administration to the CNS, preferably avoiding or minimizing delivery to the PNS. In embodiments, the SCN10a antagonist is administered or delivered concurrently with, or at a different time from, the KCNQ1 antagonist. In embodiments of the method, the SCN10a channel antagonist may be one or more of A-803467, aryl-substituted nicotinamide derivatives of A-803467, PF-01247324, PF-04531083, PF-6305591, PF-04885614, PF-5157147, A-887826, Ambroxol hydrochloride, DSP-2230, vinpocetine, VX-150, and APETx2 (SEQ ID NO:12). (See, Table 1). In preferred embodiments, the SCN10a channel antagonist is PF-04531083. In other embodiments, the SCN10a channel antagonist is an SCN10a-specific interfering RNA, a biologic that blocks SCN10a activity, or a Crispr/Cas9 construct which mutates the SCN10a gene, as described further herein. In others embodiment of the method, if an antagonist of KCNQ1 is also administered to the subject, the KCNQ1 antagonist may be one or more of Chromanol 293B, HMR-1556, UCL2077, JNJ303, L-735821 (L-7), or fenofibrate (see, Table 2); a KCNQ1-specific interfering RNA; or a biologic that blocks KCNQ1 activity, such as an anti-KCNQ1 antibody.

According to an embodiment of the present methods, the ion channel antagonist is especially useful for treating PTHS, as well as other neurological disorders, e.g., schizophrenia, autism, autism spectrum disorders, 18q syndrome, etc., to prevent intrinsic excitability defects, e.g., aberrant or abnormal action potential (AP) spiking and/or AHP current levels, in neuronal cells of the CNS through ion channels that are normally expressed and active in the PNS, particularly in CNS neuronal cells having defective TCF4 expression or function, resulting from, for example, TCF4 gene haploinsufficiency or TCF4 mutation. In an embodiment, the ion channel is a sodium channel, preferably SCN10a, and the ion channel antagonist specifically blocks the sodium channel, preferably SCN10a. In an embodiment, the ion channel is a potassium channel, preferably KCNQ1, and the ion channel antagonist specifically blocks the potassium channel, preferably KCNQ1.

The invention further relates to and newly provides the identification of sodium and/or potassium ion channels that are ectopically expressed and active in excitatory neuronal cells of the CNS, rather than in neuronal cells of the PNS, thus causing the pathophysiology underlying certain neurological and neurodevelopmental diseases, for example, Pitt-Hopkins Syndrome (PTHS), schizophrenia, autism and autism spectrum disorders. According to the invention, defective TCF4 expression or function, e.g., through mutation(s) in TCF4 and/or haploinsufficiency, results in de-repression of the ion channel gene expression and function in CNS neuronal cells where these ion channels are not normally expressed. In accordance with the invention, methods of treating and/or reducing the symptoms of these neurological or neurodevelopmental diseases or disorders involve administering to a subject in need one or more ion channel antagonists, particularly, selective or specific ion channel antagonists, that therapeutically target the sodium or potassium ion channel and block its expression and/or activity so as to treat and/or reduce the symptoms of the disease or disorder in the subject. In an embodiment, the targeted neuronal cell sodium ion channel is preferably SCN10a, and a selective SCN10a antagonist is administered to the subject. In an embodiment, the targeted neuronal cell potassium ion channel is KCNQ1 (Kv7.1), and a selective KCNQ1 (Kv7.1) antagonist is administered to the subject. In an embodiment, both the SCN10a and KCNQ1 ion channels are therapeutically targeted in the methods employing antagonists which block the expression and/or activity of these ion channels. In an embodiment, administration is by a means or route that allows the antagonist to be substantially delivered to cells of the CNS, i.e., to cross the blood-brain barrier, for example and without limitation, intrathecal administration.

In a further aspect, the present invention provides the use of a therapeutically effective amount of an antagonist of sodium channel SCN10a, an antagonist of potassium channel KCNQ1, or a combination thereof, in the manufacture of a medicament for treating and/or reducing the symptoms of a neurological or neurodevelopmental disease or disorder that is associated with ectopic expression and/or activity, e.g., excitability, of the SCN10a channel, the KCNQ1 channel, or both, in neuronal cells of the CNS rather than in neuronal cells of the PNS in a subject in need by administering to the subject an effective amount of the SCN10a antagonist, or the KCNQ1 antagonist, or a combination thereof, to treat and/or reduce the symptoms of the neurological or neurodevelopmental disease or disorder. In an embodiment, the neurological or neurodevelopmental disease or disorder is associated with defective or abnormal TCF4 transcription factor gene expression and/or protein function in the neuronal cells, which results in the ectopic expression of these ion channels in CNS neuronal cells through de-repression of their expression in the CNS cells. In an embodiment, the subject has, is suspected of having, or is at risk of having, such a neurological or neurodevelopmental disease or disorder. In embodiments, the disease or disorder is PTHS, autism, autism spectrum disorder, schizophrenia, or 18q syndrome. In embodiments of the use, the SCN10a channel antagonist may be one or more of A-803467, aryl-substituted nicotinamide derivatives of A-803467, PF-01247324, PF-04531083, PF-6305591, PF-04885614, PF-5157147, A-887826, Ambroxol hydrochloride, DSP-2230, vinpocetine, VX-150, and APETx2 (SEQ ID NO:12). (See, Table 1). In other embodiments, the SCN10a channel antagonist is an SCN10a-specific interfering RNA, a biologic which blocks SCN10a activity, or a Crispr/Cas9 construct which mutates the SCN10a gene, as described further herein. In others embodiments of the use, if an antagonist of KCNQ1 is also administered to the subject, the KCNQ1 antagonist may be one or more of Chromanol 293B, HMR-1556, UCL2077, JNJ303, L-735821 (L-7), or fenofibrate (Table 2); a KCNQ1-specific interfering RNA; or a biologic which blocks KCNQ1 activity.

In another aspect, the present invention provides a method of correcting (i.e., altering the excitability profile of the CNS neuronal cell so that it is more like that of a CNS neuronal cell that does not ectopically express SCN10a and KCNQ1) the abnormal phenotype of a CNS neuronal cell in which ectopic expression of SCN10a and/or KCNQ1 causes a reduction in frequency of action potential (AP) spiking and increased afterhyperpolarization (AHP) current in a subject having, suspected of having, or at risk for, a neurological or neurodevelopmental disease or disorder associated with said abnormal AP output and/or AHP current, the method comprising: administering to the subject a therapeutically effective amount of an SCN10a antagonist to increase AP output in the CNS neuronal cells of the subject. Such an increase in AP output by the SCN10a antagonist may also indirectly decrease the AHP in the cells. In embodiments, the antagonist is an interfering RNA directed against the Nav1.8 sodium channel, a Crispr/Cas9 construct which mutates the SCN10a gene, or a biologic which blocks Nav1.8 sodium channel activity. In embodiments of the method, the SCN10a channel antagonist may be one or more of A-803467, aryl-substituted nicotinamide derivatives of A-803467, PF-01247324, PF-04531083, PF-6305591, PF-04885614, PF-5157147, A-887826, Ambroxol hydrochloride, DSP-2230, vinpocetine, VX-150, and APETx2 (SEQ ID NO:12). In other embodiments, the SCN10a channel antagonist is an SCN10a-specific interfering RNA, or a biologic, such as an antibody, that blocks SCN10a activity, or a Crispr/Cas9 construct which mutates the SCN10a gene, as described further herein.

In yet another aspect, the present invention provides a method of correcting an aberrant intrinsic excitability phenotype of CNS neuronal cells aberrantly expressing sodium channel SCN10a in a subject having, suspected of having, or at risk for, a neurological or neurodevelopmental disorder associated with abnormal TCF4 expression and/or function, the method comprising administering to the subject a therapeutically effective amount of an antagonist of SCN10a to correct the phenotype of the CNS neuronal cells and reduce the symptoms of the neurological or neurodevelopmental disorder in the subject. In embodiments of the method, the SCN10a channel antagonist may be one or more of A-803467, aryl-substituted nicotinamide derivatives of A-803467, PF-01247324, PF-04531083, PF-6305591, PF-04885614, PF-5157147, A-887826, Ambroxol hydrochloride, DSP-2230, vinpocetine, VX-150, and APETx2 (SEQ ID NO:12). In other embodiments, the SCN10a channel antagonist is an SCN10a-specific interfering RNA, a Crispr/Cas9 construct which mutates the SCN10a gene, or a biologic that blocks SCN10a activity as described further herein.

In another of its aspects, the invention provides a method of correcting an aberrant intrinsic excitability phenotype in central nervous system (CNS) neurons ectopically expressing sodium ion channel SCN10a in a subject in need, wherein said phenotype is associated with symptoms of behavioral and cognitive defects in a subject having Pitt-Hopkins Syndrome (PTHS), the method comprising administering to the subject a therapeutically effective amount of an antagonist of SCN10a to correct the aberrant intrinsic excitability phenotype of the CNS neuronal cells and to reduce the symptoms of behavioral and cognitive defects in the subject. In an embodiment, the CNS neuronal cells are prefrontal cortex neuronal cells, in particular, prefrontal cortex pyramidal cells. In an embodiment, the SCN10a channel antagonist is administered to the subject intrathecally or intracranially.

In another aspect, the invention provides a method for treating a subject afflicted with PTHS, comprising administering to the subject an effective amount of a pharmaceutically acceptable antagonist of the SCN10a ion channel to confer normal intrinsic excitability and/or to increase AP output and/or to decrease the AHP current in the treated subject's CNS neuronal cells, particularly, in prefrontal cortical neurons of the CNS. In an embodiment, the SCN10a channel antagonist may be one or more of A-803467, aryl-substituted nicotinamide derivatives of A-803467, PF-01247324, PF-04531083, PF-6305591, PF-04885614, PF-5157147, A-887826, Ambroxol hydrochloride, DSP-2230, vinpocetine, VX-150, and APETx2 (SEQ ID NO:12) (See, Table 1); an SCN10a-specific interfering RNA; or a biologic which blocks SCN10a activity. In another embodiment, the SCN10a antagonist is a Crispr/Cas9 construct which mutates the SCN10a gene. In another embodiment, an antagonist of KCNQ1 is also administered to the subject. In an embodiment, the KCNQ1 antagonist may be one or more of Chromanol 293B, HMR-1556, UCL2077, JNJ303, L-735821 (L-7), or fenofibrate (See, Table 2); or a KCNQ1-specific interfering RNA; or a biologic which blocks KCNQ1 activity.

In other embodiments of any of the above treatment methods, the subject undergoing treatment has, is suspected of having, or is at risk for, a neurological or neurodevelopmental disease or disorder selected from the group consisting of Pitt-Hopkins Syndrome (PTHS), autism, autism spectrum disorders, 18q syndrome, or schizophrenia. In another embodiment of the above methods, the SCN10a and/or the KCNQ1 channel antagonist is administered to the subject intrathecally, intracranially, or by other modes that preferably target neuronal cells of the CNS, particularly, CNS prefrontal cortical neurons, and also preferably do not reach the PNS.

In another of its aspects, the present invention provides in vitro and in vivo assays and techniques, as described in the Examples herein, for identifying antagonist compounds, agents, or substances, in particular, pharmaceutically acceptable SCN10a antagonists, as drugs for treating and/or reducing the symptoms of the neurological or neurodevelopmental diseases or disorders, including, for example, normalizing behavioral and cognitive deficits in subjects afflicted with PTHS, in which an Nav1.8 subtype sodium channel, preferably, SCN10a, is ectopically expressed and active in neurons of the CNS. In an embodiment, the CNS neurons that ectopically express the SCN10a channel and may harbor a TCF4 transcription factor whose expression and/or activity is defective due, for example, to mutation and/or haploinsufficiency. In some embodiments, the assays and techniques may identify antagonist compounds, agents, or substances, in particular, pharmaceutically acceptable SCN10a antagonists, that block, reduce, or suppress SCN10a activity in neuronal cells of the CNS, in particular, prefrontal cortical neurons.

BRIEF DESCRIPTION OF THE FIGURES

FIGS. 1A-1D show the developmental expression pattern and shRNA knockdown of TCF4. (A) Comparison of the lifespan expression patterns of TCF4 between humans and rats. Human dorso-lateral prefrontal cortex (DLPFC) expression data for TCF4 on 269 individuals across the lifespan was obtained from: http://braincloud.jhmi.edu/plots/Red: smoothing spline (upper panel). qRT-PCR analysis of TCF4 transcripts obtained from rat cortical samples (lower panel). (B-D) In vitro validation of TCF4 shRNAs to effectively knockdown TCF4 expression. (B, C) Rat neuroblastoma cells were transfected with shRNA constructs and an equal amount of cell lysate sample from each condition was subjected to Western blot analysis for endogenous TCF4 protein (shTCF4=1.9±2.0% of control, N=4, Bonferroni p<0.0001; shTCF4_2=36.4±4.3% of control, N=4, Bonferroni p<0.0001). (D) Rat neuroblastoma cells were transfected with shRNA constructs and subjected to qRT-PCR for TCF4 transcript (shTCF4=0.55±0.15 fold change from control, N=4, Bonferroni p=0.0065; shTCF4_2 0.47±0.11 fold change from control, N=4, Bonferroni p=0.0017). Values are presented as Tukey boxplots and statistical significance via Bonferoni post hoc analysis (** p<0.01, # p<0.0001).

FIGS. 2A-2F show that TCF4 regulates intrinsic excitability of L2/3 pyramidal cells of the mPFC. (A, B) In utero shRNA knockdown of TCF4 prevents neurons from displaying repetitive spiking. Shown in (A) are sample whole-cell current-clamp traces recorded from EGFP+ neurons expressing shCon, shTCF4, or shTCF4_2 in response to 600 ms current injections (+300 and −50 pA). (B) Summary data of the frequency of APs generated in response to current injections. Post hoc analysis indicated that shTCF4 cells (N=30) between 250 and 500 pA and shTCF4_2 cells N=41 between 350 and 500 pA produced significantly fewer spikes than shCon cells (N=35). Co-expression of human TCF4B+ shTCF4 (B, C) resulted in a complete rescue of AP output and post hoc analysis revealed no statistical difference between rescue cells (N=25) and shCon cells (N=35) at any current injection. (C) Group data depicting the maximum AP frequency obtained from each neuron from all conditions. Post hoc comparisons of the maximum AP frequency indicated that shTCF4 (15.79±1.8 Hz, N=30; Bonferroni p<0.0001) and shTCF4_2 (20.77±1.5 Hz, N=41; Bonferroni p=0.032) were significantly reduced compared to shCon (25.51±1.04 Hz, N=35). (D, E) In utero knockout of TCF4 by CRISPR-Cas9-mediated mutation prevents neurons from displaying repetitive spiking. Shown in (D) are sample whole-cell current-clamp traces recorded from EGFP+ neurons expressing crEmpty or crTCF4 in response to 600 ms current injections (+300 and −50 pA). (E) Summary data of the frequency of APs generated in response to current injections. crTCF4 produced a significant reduction in the frequency neuronal spiking compared to crEmpty cells. Post hoc analysis indicated that crTCF4 cells (N=20) between 150 and 500 pA produced significantly fewer spikes than crEmpty cells (N=17). (F) Group data depicting the maximum AP frequency obtained from each neuron in each condition. The maximum spiking frequency analysis showed that crTCF4 cells (16.89±1.54 Hz, N=20; unpaired t-test p=0.0016) were significantly reduced compared to crEmpty cells (24.90±1.78 Hz, N=17). Values are presented as mean±s.e.m. (B, E) or Tukey boxplots (C, F) and statistical significance via Bonferroni post hoc analysis (B, C, E) or unpaired t-test (F) (* p<0.05, ** p<0.01, & p<0.001 # p<0.0001).

FIGS. 4A-4C show that iTRAP Molecular profiling of the translatome identifies KCNQ1 and SCN10a. (A) Sample image of mPFC L2/3 neurons IUE-transfected with the ribosomal subunit L10a-EGFP. (B) iTRAP protocol enriches RNA from IUE transfected excitatory neurons. qRT-PCR comparison of the affinity purified RNA (bound) vs. the unbound fraction of RNA for cellular markers of interneurons (GAD1 fold-change 0.52±0.07, N=4; paired t-test p=0.007), astrocytes (GFAP fold-change 0.58±0.08, N=4; paired t-test p=0.01), oligodendrocytes (OLIG1 fold-change 0.25±0.04, N=4; paired t-test p=0.0003) and transfection marker (EGFP fold-change 408.9±95.9, N=4; paired t-test p=0.0006). (C) Comparison of the ion channel translatome between shTCF4 and shCon cells. Shown is the fold-change difference in expression between knockdown and control mPFC brain tissue ordered by p-values. Values are presented mean±SEM statistical significance via Bonferoni post hoc analysis (* $p<0.05$,  $p<0.01$, * $p<0.001$).

FIG. 9 shows a table that compares intrinsic excitability measures for all TCF4 models. Yellow highlighted boxes indicate a measurement that was significantly different from its control. Green highlighted boxes indicate a measurement that was not significantly different from its control.

FIGS. 11A-11E show the results of validation of CRISPR-Cas9 targeting of TCF4. (A) Surveyor assay performed in transfected rat neuroblastoma cells showing base pair mismatch dependent nuclease activity. (B) Wildtype (WT) sequence of the TCF4 genomic region that was targeted for CRISPR-Cas9 mutation (SEQ ID NO:5). Bold letters indicate the PAM sequence in SEQ ID NO:5. Below are five examples of indels that were sequenced from TA clones following crTCF4 transfection (Δ2: SEQ ID NO:6; +2: SEQ ID NO:7; +1: SEQ ID NO:8; Δ1 (Δ2+1): SEQ ID NO:9; and Δ17: SEQ ID NO:10). (C) TCF4 Western blot showing knockdown of endogenous TCF4 protein in rat neuroblastoma cells transfected with crTCF4 or crEmpty. (D, E) Summary data showing the mAHP amplitude, but not the sAHP amplitude, is significantly larger in crTCF4 neurons compared to crEmpty neurons.

FIGS. 13A-13D show that pharmacological block of KCNQ1 and SCN10a rescues phenotypes associated with CRISPR-Cas9-mediated suppression of TCF4. (A) Summary data of the effect of UCL2077 application on the frequency of APs in crTCF4 cells generated in response to current injections (N=7). Post hoc analysis indicates UCL2077 significantly increased firing frequency for current pulses between 400 and 500 pA. (B) Summary data of the effect of A-803467 application on the frequency of APs in crTCF4 cells generated in response to current injections (N=8). Post hoc analysis indicates A-803467 significantly increased firing frequency for current pulses between 400 and 500 pA. (C, D) No effect on AP frequency was observed in crEmpty cells after application of either UCL2077 or A-803467.

FIGS. 14A-14H depict results showing a lack of conditional selectivity by the M-current blocker carbachol. (A) Average whole-cell voltage clamp traces showing the efficacy of carbachol to block the sAHP in shTCF4 cells. (B) Sample current-clamp traces showing the before (shTCF4) and after (shTCF4+carbachol) effects of bath application of carbachol on neuronal spiking induced by a 600 ms current injection (300 pA, N=8). (C) Summary data depicting the effect of carbachol on neuronal firing frequency across a series of current pulses (600 ms, 50 to 500 pA) for shTCF4 cells (p=0.0075, N=8). (D, E) Summary data of peak amplitude of the AHP before and after application of carbachol in shTCF4 cells, both the mAHP (−6.78±0.70 vs. −4.23±0.60 mV, N=8; paired t-test p=0.0051) and sAHP (−3.91±0.52 vs. 2.33±0.58 mV, N=8; paired t-test p=0.046) amplitudes were significantly reduced by carbachol. (F) Summary data depicting the effect of carbachol on neuronal firing frequency for shTCF4 cells (p=0.0038, N=12). (G, H) Summary data of peak amplitude of the AHP before and after application of carbachol in shCon cells, both the mAHP (−4.21±0.52 vs. −2.32±0.31 mV, N=19; paired t-test p=0.0008) and sAHP amplitudes (−3.13±0.45 vs. −1.10±0.32 mV, N=19; paired t-test p=0.0004) were significantly reduced by carbachol. Values are presented as Tukey boxplots and statistical significance via Bonferoni post hoc analysis (* p<0.05, ** p<0.01, & p<0.001).

As expected from the carbachol effect on sAHP current, bath application of carbachol was effective at rescuing action potential frequency in shTCF4 neurons (N=8; ANOVA$_{(cond)}$). A similar effect of carbachol was observed in shCon cells. Bath application of carbachol increased spiking (N=12; ANOVA$_{(cond)}$) and post hoc comparisons indicated carbachol was effective at increasing spiking for current injections between 200 and 500 pA (FIG. 14F; p-values in figure; and FIGS. 14G, H).

FIG. 16 shows in tabular form that Chip-Seq identifies multiple TCF4 binding sites on KCNQ1 and SCN10a in rat neuroprogenitor cells. Information about the genomic coordinates, false discovery rate (FDR), gene name, location, distance from transcriptional start site (TSS), and number of Ebox motifs (CANNTG) observed beneath the genomic coordinates are provided. Four FDR significant peaks for SCN10a and 12 FDR significant peaks for KCNQ1 were identified.

DETAILED DESCRIPTION OF THE INVENTION

Figures 3A, 3B, 3C, 3D, 3E, 3F, 3G, 3H, 3I:
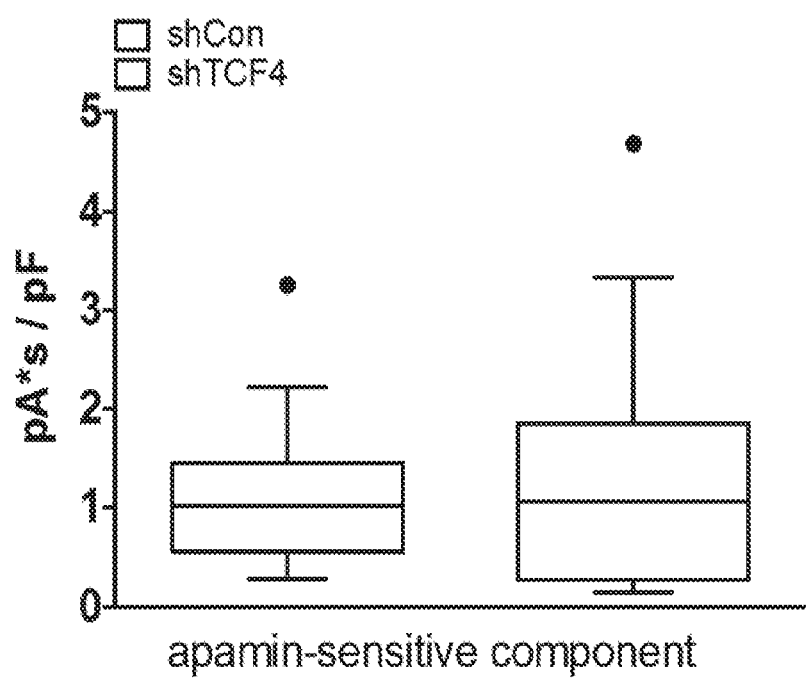
FIGS. 3A-3I show that TCF4 regulates the afterhyperpolarization potential (AHP). (A-C) Suppression of TCF4 results in an increase in the medium and slow AHP potential. Shown in (A) is a sample whole-cell current clamp traces highlighting the AHP that follows a train of APs produced by a 600 ms current pulse. (B) Summary data comparing the peak amplitude of the mAHP from EGFP+ neurons expressing either shCon or shTCF4 constructs (shTCF4= −4.76±0.35 mV, N=26 vs. shCon=−2.98±0.24 mV, N=26); unpaired t-test p<0.0001). The mAHP was measured at the peak of AHP following the current pulse. (C) Summary data comparing the amplitude of the sAHP obtained from EGFP+ neurons expressing either shCon or shTCF4 constructs (shTCF4=−2.94±0.19 mV, N=26 vs. shCon=−1.89±0.19 mV, N=26; unpaired t-test p=0.0003). The sAHP was measured 280 ms after the current pulse. (D-H) Whole-cell voltage-clamp recordings of AHP currents produced by applying 100 ms voltage steps to +45 mV. Shown are average traces from all recordings from EGFP+ cells expressing shCon (black traces) or shTCF4 (blue traces). Shown in (D) is the baseline AHP current produced in the presence of the GABA and glutamate antagonists, gabazine and NBQX, respectively. Average traces showing progressive blockade of the fAHP current (E) by bath application of TEA, followed by blockade of the mAHP current with apamin (F). (G) Summary data showing the total charge transfer obtained from all recorded neurons in each pharmacological condition. All data was normalized by the cells capacitance (pF). (H) Average subtracted traces before and after application of apamin (panel E minus panel F). (I) Summary data comparing only the apamin-sensitive component of the AHP currents between EGFP+ cells expressing either shCon or shTCF4. Values are presented as Tukey boxplots and statistical significance obtained via unpaired t-test (* $p<0.05$, ** $p<0.01$, & $p<0.001$ # $p<0.0001$).

The present invention relates to the discovery by the inventors that the ectopic expression of potassium and sodium ion channel genes, namely, the KCNQ1 and SCN10a genes, and the activity of their encoded products in neuronal cells of the CNS, rather than in neuronal cells of the PNS where they are normally expressed and active, is associated with neurological and neurodevelopmental diseases and disorders, and symptoms thereof. In addition, antagonists of the sodium and potassium channels, in particular, a KCNQ1 antagonist, and an SCN10a antagonist, may be used to correct aberrations in the intrinsic excitability caused by the inappropriate activity of one or both of these ion channels in CNS neuronal cells.

More specifically, the inventors have newly determined that the TCF4 transcription factor directly regulates the expression and activity of potassium and sodium channel target genes, namely, the KCNQ1 and SCN10a genes, respectively, by binding to genomic regions within these genes, thereby regulating their expression in neuronal cells, in particular, prefrontal cortical neurons of the CNS. TCF4 was determined to act as a repressor of KCNQ1 and SCN10a gene expression, such that defective TCF4 gene expression and/or protein function, e.g., due to TCF4 mutation or haploinsufficiency, for example, leads to ectopic expression of the KCNQ1 and SCN10a genes in prefrontal cortical neurons of the CNS, which reflects the pathophysiology behind neurological and neurodevelopmental disorders associated with a lack of normal TCF4 expression and/or function.

Haploinsufficiency of TCF4 (i.e., mutation of one of the TCF4 genes) results in ectopic expression of SCN10a while a loss of TCF4 function, for example due to a mutation resulting in a dominant negative TCF4 protein, results in ectopic expression of both SCN10a and KCNQ1. By way of example, in a rat model of TCF4 haploinsufficiency in which only one of the TCF4 genes is mutated, and in certain human patients, SCN10a overexpression and KCNQ1 underexpression is observed in CNS neuronal cells. In these cases, SCN10a overexpression affects the AP output in the CNS neurons, and a change in AHP is a byproduct of this change. In a mouse model and in certain human patients having a TCF4 mutation resulting from a truncation which causes the TCF4 protein to work as a dominant negative, TCF4 activity is absent from the CNS cells, and both the SCN10a and the KCNQ1 channels are overexpressed, with a resulting direct effect on AP frequency and amplitude, which are reduced, and on AHP, which is increased. In an embodiment of the invention, when the neurological or neurodevelopmental disease or disorder is associated with TCF4 haploinsufficiency, an antagonist of SCN10a is used to treat a subject in need. In another embodiment of the invention, when the neurological or neurodevelopmental disease or disorder is associated with a TCF4 mutation resulting in a dominant-negative TCF4, an antagonist of SCN10a, an antagonist of KCNQ1, or, preferably, a combination of an antagonist of SCN10a and an antagonist of KCNQ1 are used to treat a subject in need thereof. Neurological and neurodevelopmental disorders associated with TCF4 mutation or haploinsufficiency include, for example, Pitt-Hopkins Syndrome (PTHS), autism, autism spectrum disorders, schizophrenia and 18q syndrome, and the like.

In prefrontal cortical cells of the CNS, the translation of the KCNQ1 and SCN10a genes was newly found to be significantly upregulated by the knockdown of TCF4, thereby leading to the expression of these ion channels in the CNS neuronal cells, altering the intrinsic excitability of these cells. This effect was surprisingly found to occur in cells of the central nervous system, indicating a role of SCN10a expression in neuronal cells of the central nervous system, rather than in cells of the peripheral nervous system, where the expression of SCN10a normally occurs. In addition, pharmacological rescue by ion channel antagonists and molecular phenocopy of the pathophysiology both in vitro and in vivo, as described in the Examples herein, validated and substantiated the KCNQ1 and SCN10a genes and/or their encoded proteins as therapeutic targets for antagonists, inhibitors, or blockers of these ion channels in treating or reducing the pathophysiology leading to neurological and neurodevelopmental disorders. Accordingly, antagonists of these ion channels can be administered to an individual having a neurological or neurodevelopmental disease or disorder that results in aberrant or abnormal expression and activity of these ion channel genes and/or their encoded products in CNS neurons so as to treat the individual's pathophysiological defects and/or to reduce cognitive deficits and other symptoms related to such neurological or neurodevelopmental diseases or disorders.

To gain insight into the biology of TCF4 and the pathophysiology resulting from TCF4 haploinsufficiency, an in vivo cell-autonomous model of PTHS was developed, using in utero electroporation (IUE) to knock down the expression of TCF4 beginning just prior to neurogenesis in the developing rat prefrontal neocortex, as described in the Examples herein. This genetic manipulation produced alterations in intrinsic excitability resulting from de-repression of the expression of specific ion channel genes that regulate the frequency of action potential (AP) spiking and AHP in neuronal cells. In addition, these excitability phenotypes were replicated in a mouse model of PTHS. The results indicate that the intrinsic excitability phenotypes underlie at least some aspects of pathophysiology observed in PTHS and schizophrenia.

According to the invention, the pathophysiology associated with neurological and neurodevelopmental disorders, e.g., PTHS, schizophrenia, autism, autism spectrum disorders, results from impaired or defective TCF4 transcription factor gene regulation of the expression of specific ion channel genes, namely, KCNQ1 and SCN10a, which, in turn, regulate the intrinsic excitability, e.g., the frequency of action potential (AP) spiking, in neuronal cells. In particular, haploinsufficiency of TCF4 produces intrinsic excitability defects or deficits that result from de-repression of the expression of the ion channel genes that affects their AP output frequency in cortical neurons, thus leading to neurological disorders. In addition, ectopic expression of these ion channel genes alters the afterhyperpolarization (AHP) of neuronal cells. Neurological and neurodevelopmental diseases and disorders associated with the above pathophysiology include, for example, Pitt-Hopkins Syndrome (PTHS), autism, autism spectrum disorders, schizophrenia, etc. The intrinsic excitability defects or deficits in affected neurons include, for example, an increase in the resting membrane potential (RMP), (See, e.g., FIG. 9; $p<0.005$), reduced frequency of AP output, (See, e.g. FIGS. 2 and 7; $p<0.0001$), and increased AHP (See, e.g., FIGS. 3 and 11; $p<0.05$).

More specifically, studies by the inventors have demonstrated that aberrant or defective TCF4 expression and/or function, resulting, for example, from TCF4 haploinsufficiency, produced deficits in the intrinsic excitability in neurons of the developing prefrontal cortex. Such aberrant excitability resulted from de-repression of the expression of specific sodium and potassium ion channel genes that regulate the frequency of action potential (AP) spiking (spike frequency adaptation) in neuronal cells of the CNS. In particular, the KCNQ1 and SCN10a ion channel encoding genes represent target genes involved in pathophysiological excitability in neuronal cells of the CNS, rather than in neurons of the peripheral nervous system, in subjects afflicted with neurodevelopmental disorders, such as PTHS.

PTHS, characterized as a rare autism spectrum disorder, is an example of a neurodevelopmental disorder having variable symptomatology that likely stems from the allelic heterogeneity represented in deletions/mutations in the TCF4 gene that produce both haploinsufficiency and/or dominant negative effects. According to the present invention, TCF4 expression deficiency leads to intrinsic excitability defects that are in part due to altered expression of the SCN10a ion channel, or both the SCN10a and KCNQ1 ion channels, in CNS neuronal cells. Without wishing to be bound by theory, the pathological expression of these peripheral ion channels in neuronal cells of the central nervous system (CNS) rather than in the peripheral sensory nervous system (PNS) provides a rationale for the use of therapeutic agents that target and preferably antagonize these ion channels, advantageously without producing unwanted off-target effects on normal neuronal physiology. Moreover, targeting these ion channels and blocking their expression and/or activity in CNS neuronal cells may ameliorate cognitive deficits or other symptoms that are observed in PTHS, as well as in other neurological and neurodevelopmental disorders such as schizophrenia, autism and autism spectrum disorders, whose pathophysiology is associated with the ectopic expression of sodium channels such as SCN10a, and/or the ectopic expression of potassium channels such as KCNQ1, the expression and function of which are regulated by TCF4.

As mentioned hereinabove, the term antagonize may be considered to be synonymous with the terms block, inhibit, prevent, suppress, abrogate, eliminate, substantially reduce, suppress, quell, as well as others known and used in the art, relates to the action of molecules, agents, compounds, drugs, medicaments, or substances to antagonize the expression and/or the activity of an ion channel gene and/or protein in a cell, in particular, a neuronal cell of the CNS, e.g., a prefrontal cortical neuron. Preferably, the antagonist is specific for a particular ion channel type or subtype and has minimal or substantially no effect on the expression and/or activity of ion channels of other types or subtypes, thereby resulting in fewer off-target or adverse effects in a subject undergoing treatment. In some embodiments, the antagonist is specific for SCN10a. In some embodiments, the antagonist is specific for KCNQ1. In a particular embodiment, an antagonist of the sodium channel SCN10a is used in a method of treating and/or reducing symptoms of a neurological or neurodevelopmental disease or disorder, wherein the SCN10a antagonist blocks or inhibits the expression and/or activity of SCN10a in neuronal cells of the CNS in individuals having defective neuronal TCF4 expression and/or function, thereby resulting in the pathophysiology of the CNS neuronal cells in individuals having certain neurological or neurodevelopmental diseases or disorders. In an embodiment, the neurological or neurodevelopmental disease or disorder is selected from PTHS, autism, autism spectrum disorder, or 18q syndrome.

In an embodiment, the methods of the invention encompass the use of a sodium channel antagonist, or more than one sodium channel antagonist, that antagonizes (blocks) the expression and/or function of the sodium channel for treating and/or reducing the symptoms of a neurological or neurodevelopmental disease or disorder in which the sodium channel is ectopically expressed and active in neuronal cells of the CNS rather than in neuronal cells of the PNS. In an embodiment, the sodium channel is of the Nav1.8 subtype. In an embodiment, the sodium channel is SCN10a. In an embodiment, the antagonist is a selective Nav1.8 or SCN10a sodium channel antagonist, e.g., a molecule that selectively blocks the expression and/or activity of a tetrodotoxin-resistant sodium channel. In an embodiment, the selective SCN10a antagonist is PF-04531083. In an embodiment, the subject has haploinsufficiency of TCF4 and is administered a selective SCN10a antagonist. In an embodiment, the methods of the invention encompass the use of a potassium channel antagonist, or more than one potassium channel antagonist, that antagonizes the expression and/or function of the potassium channel for treating and/or reducing the symptoms of a neurological or neurodevelopmental disease or disorder in which the potassium channel is expressed and active in neuronal cells of the CNS rather than in neuronal cells of the PNS. In an embodiment, the potassium channel is KCNQ1. In an embodiment, the antagonist is a selective KCNQ1 antagonist, e.g., a molecule that selectively blocks the expression and/or activity of a potassium channel having properties similar to those of KCNQ1. In a specific embodiment, the selective KCNQ1 antagonist is UCL2077, JNJ303, L-735821 (L-7), or fenofibrate.

In other embodiments, one or more sodium channel antagonists may be used in the methods of the invention. In other embodiments, one or more potassium channel antagonists may be used in the method of the invention. In other embodiments, one or more sodium channel antagonists may be used in combination with one or more potassium channel antagonists. In an embodiment, if both a sodium channel antagonist and a potassium channel antagonist are to be administered to a subject in need thereof, the sodium channel antagonist may be administered at the same time as, or at a different time from, the administration of the potassium channel antagonist. In addition, the sodium channel antagonist and/or the potassium channel antagonist may be administered in any order to a subject in need, at the discretion of the medical or clinical practitioner. In specific embodiments, the sodium channel is SCN10a, and the antagonist is an SCN10a antagonist, or an antagonist of a sodium channel subtype having properties similar to SCN10a. In other specific embodiments, the potassium channel is KCNQ1, and the antagonist is a KCNQ1 antagonist, or an antagonist of a potassium channel subtype having properties similar to KCNQ1.

In an embodiment, the ion channel antagonist may be a small molecule, such as chemically synthesized and purified small molecule or chemical compound. In an embodiment, the small molecule antagonizes the expression and/or function of the voltage-gated, sodium channel SCN10a. In an embodiment, the small molecule antagonizes the expression and/or function of the potassium channel KCNQ1. In other embodiments, an antagonist of an ion channel may be a biologic molecule, such as a peptide, a polypeptide or protein, a fusion polypeptide or protein, or an antibody. By way of nonlimiting example, an antibody may be directed to the alpha subunit of the sodium channel, or to other epitopes on the protein that result in blocking the activity of the sodium channel, i.e., SCN10a, upon antibody binding to the sodium channel protein. The antibody may be any type of immunotherapeutic molecule known in the art, for example but not limited to, an IgG, a human antibody, a humanized antibody, a chimeric antibody, an scFv, a Fab or Fv fragment, or other antigen binding fragment of an immunoglobulin molecule. The biologic as antagonist may be recombinantly produced, and/or isolated and purified from an appropriate source. In other embodiments, the antagonist may be, without limitation, an antisense nucleic acid (RNA), an interfering RNA (RNAi), an siRNA, miRNA, or shRNA, and the like, which is directed against SCN10a or KCNQ1 RNA or DNA sequences and acts to block or inhibit the expression and/or activity of the targeted ion channel; or a Crispr/Cas9 construct which mutates the SCN10a gene. It is envisioned that combinations of different classes of selective antagonist molecules may be utilized to block, suppress, or inhibit the expression and/or function of the SCN10a ion channel and/or the KCNQ1 ion channel. For example, a small molecule antagonist of SCN10a expression and/or functional activity may be administered in combination with a biological antagonist of KCNQ1 functional activity. Similarly, a small molecule antagonist of KCNQ1 expression and/or functional activity may be administered in combination with a biological antagonist of SCN10a functional activity.

Sodium channel antagonists for use in the methods of the invention are not meant to be limiting. Examples of sodium channel inhibitors, blockers, or antagonists for use in the treatment methods described herein include, without limitation, molecules, compounds and agents, preferably pharmaceutically and/or physiologically acceptable molecules, compounds and agents, that are available for blocking voltage gated sodium channels, particularly those of the Nav1.8 subtype, as well as those compounds and agents that are chemical derivatives of known Nav1.8 sodium channel antagonists, that are in development, in clinical trials, or that may be developed to target and antagonize such ion channels. Preferred are sodium channel antagonists that are selective for tetrodotoxin-resistant sodium channels over tetrodotoxin-sensitive sodium channels, such as antagonists of the Nav1.8 subtype, e.g., SCN10a. Examples of blockers of voltage-gated sodium channels such as Nav1.8 may be found, for example, in Tarnawa, I. et al., 2007, Recent Patents on CNS Drug Discovery, 2:57-78; Zuliani, V. et al., 2009, Curr. Topics Med. Chem., 9:396-415; and Eijkelkamp, N. et al., 2012, Brain, 135:2585-2612. Illustrative, nonlimiting examples of sodium channel blockers generally include Antiarrhythmics (class I): Ajmaline, Aprindine, Disopyramide, Dronedarone, Encainide, Flecainide. Lidocaine Lorajmine, Lorcainide, Mexiletine, Moricizine, Pilsicainide, Prajmaline, Procainamide, Propafenone, Quinidine, Sparteine, Tocainide; Anticonvulsants: Acetylpheneturide, Carbamazepine, Cenobamate, Chlorphenacemide, Eslicarbazepine acetate, Ethotoin, Fosphenytoin, Lacosamide, Licarbazepine, Mephenytoin, Oxcarbazepine, Oxitriptyline, Phenacemide, Pheneturide, Phenytoin, Rufinamide, Sipatrigine, Topiramate, Sodium valproate, Valnoctamide, Valproate pivoxil, Valproate semisodium, Valproic acid, Valpromide, Zonisamide; Diuretics: Amiloride, Benzamil, Triamterene; Local anesthetics. pFBT, Amylocaine, Articaine, Benzocaine, Bupivacaine (Levobupivacaine, Ropivacaine), Butacaine, Butamben, Chloroprocaine, Cinchocaine, Cocaine, Cyclomethycaine, Dimethocaine, Diphenhydramine, Etidocaine, Hexylcaine, Iontocaine, Lidocaine, Mepivacaine, Meprylcaine, Metabutoxycaine, Orthocaine, Piperocaine, Prilocaine, Procaine, Propoxycaine, Proxymetacaine, Risocaine, Tetracaine, Trimecaine; Analgesics: AZD-3161, DSP-2230, Funapide, GDC-0276, NKTR-171, PF-05089771, Ralfinamide, Raxatrigine, RG7893 (GDC-0287); Toxins: Conotoxins, Neosaxitoxin, Saxitoxin, Tetrodotoxin; Others: Buprenorphine, Evenamide, Menthol, Safinamide, or Tricyclic antidepressants.

In particular embodiments, suitable sodium channel blockers for use in the methods include the selective Nav1.8 sodium channel blocker A-803467 and PF-04531083. In addition, aryl-substituted nicotinamide derivatives of A-803467 are also suitable as sodium channel blockers, e.g., as reported by Kort, M. E. et al., 2010, Bioorganic and Medicinal Chemistry Letters, 20(22):6812-6815. Also suitable for use in the methods is the compound PF-01247324, as reported by Payne, C. E. et al., 2015, British Journal of Pharmacology, 172(10):2654-2670, and the compound PF-6305591, (Pfizer), as described in WO 2013/0114250, (See, Table 1), as well as arylpyrazine derivatives, e.g., heteroaryl substituted N-[6-amino-5-aryl-pyrazin-2-yl]-carboxamide derivatives (Pfizer), and phenylfurans, as reported by Zuliani, V. et al., 2009, Current Topics in Medicinal Chemistry, 9(4):396-415. Also pyridone benzamides such as 2-(4-fluoro-2-methoxyphenoxy)-N-(2-oxo-1,2-dihydropyridin-4-yl)-4-(trifluoromethyl)benzamide (US20140213616) or its prodrug VX-150 (4-(2-(4-fluoro-2-methoxyphenoxy)-4-(triflurormethyl)benzamido)-2-oxopyridin-1 (2H)-yl) methyl dihydrogen phosphate) (WO2015089361).

Specifically, the molecules set forth in Table 1 are selective Nav1.8/SCN10a sodium channel blockers for use in the methods of the invention. Also provided are pharmaceutically acceptable salts and hydrates of the compounds listed in Table 1.

TABLE 1

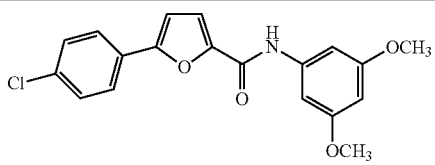

(5-(4-Chlorophenyl)-N-(3,5-dimethoxyphenyl)-2-furancarboxamide) McGaraughty et al (2008) J. Pharmacol. Exp. Ther. 324(3): 1204-11

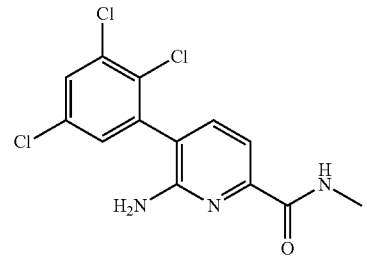

(6-amino-N-methyl-5-(2,3,5-trichlorophenyl) pyridine-2-carboxamide) See, Shields, S. D., et al. (2015). PLoS ONE, 10(3)

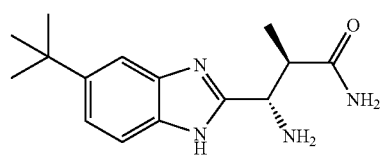

(2R,3S)-3-amino-3-(5-tert-butyl-1H-benzimidazol-2-yl)-2-methyl-propanamide) WO 2013114250

TABLE 1-continued

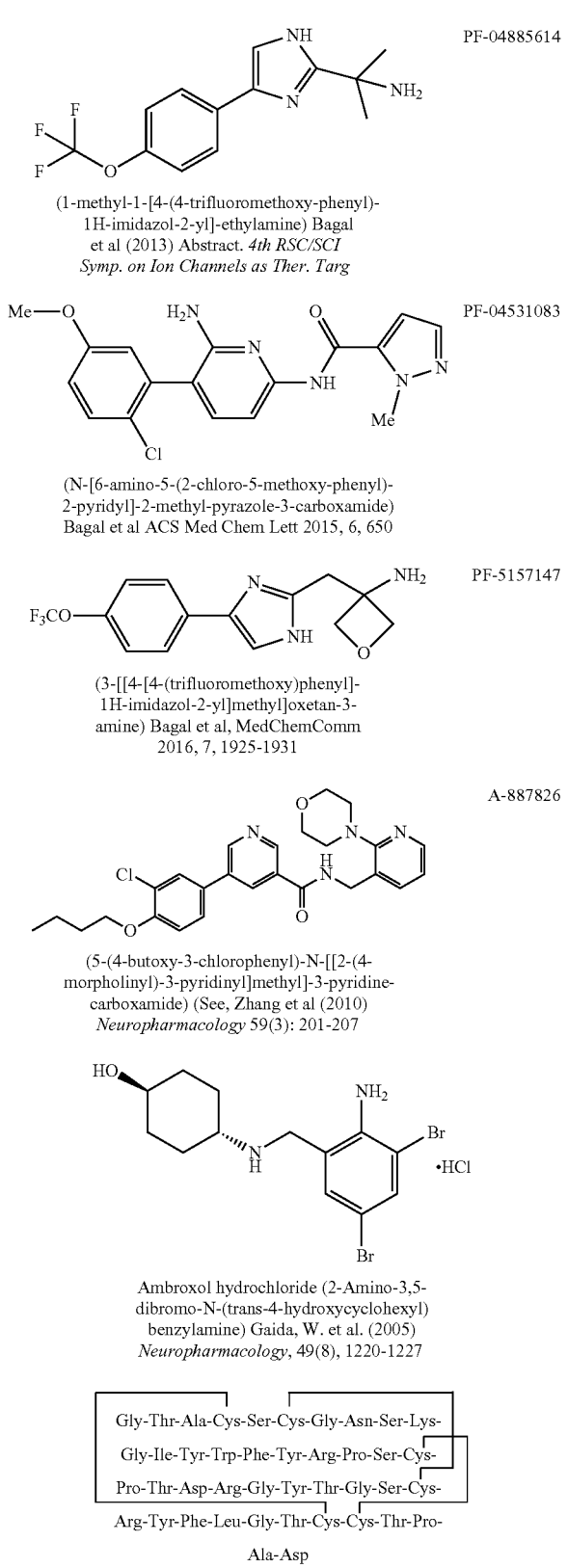

(1-methyl-1-[4-(4-trifluoromethoxy-phenyl)-
1H-imidazol-2-yl]-ethylamine) Bagal
et al (2013) Abstract. *4th RSC/SCI
Symp. on Ion Channels as Ther. Targ*  PF-04885614

(N-[6-amino-5-(2-chloro-5-methoxy-phenyl)-
2-pyridyl]-2-methyl-pyrazole-3-carboxamide)
Bagal et al ACS Med Chem Lett 2015, 6, 650  PF-04531083

(3-[[4-[4-(trifluoromethoxy)phenyl]-
1H-imidazol-2-yl]methyl]oxetan-3-
amine) Bagal et al, MedChemComm
2016, 7, 1925-1931  PF-5157147

(5-(4-butoxy-3-chlorophenyl)-N-[[2-(4-
morpholinyl)-3-pyridinyl]methyl]-3-pyridine-
carboxamide) (See, Zhang et al (2010)
*Neuropharmacology* 59(3): 201-207  A-887826

Ambroxol hydrochloride (2-Amino-3,5-
dibromo-N-(trans-4-hydroxycyclohexyl)
benzylamine) Gaida, W. et al. (2005)
*Neuropharmacology*, 49(8), 1220-1227

Gly-Thr-Ala-Cys-Ser-Cys-Gly-Asn-Ser-Lys-
Gly-Ile-Tyr-Trp-Phe-Tyr-Arg-Pro-Ser-Cys-
Pro-Thr-Asp-Arg-Gly-Tyr-Thr-Gly-Ser-Cys-
Arg-Tyr-Phe-Leu-Gly-Thr-Cys-Cys-Thr-Pro-
Ala-Asp

APETx2 (SEQ ID NO: 12)
See, Blanchard et al (2012) *Br. J. Pharmacol.*
165: 2167

TABLE 1-continued

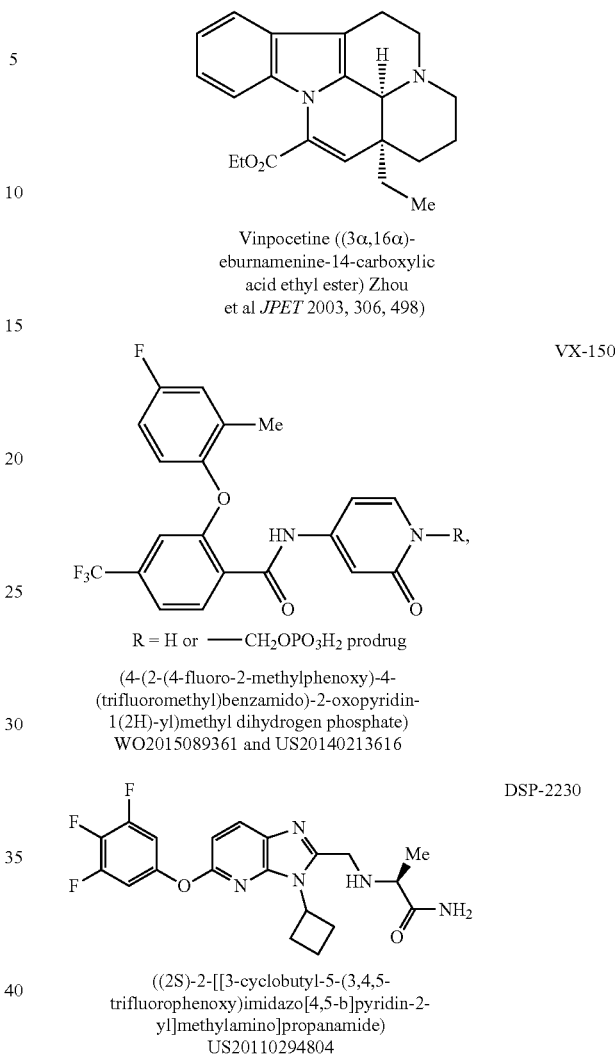

Vinpocetine ((3α,16α)-
eburnamenine-14-carboxylic
acid ethyl ester) Zhou
et al *JPET* 2003, 306, 498)

R = H or —CH$_2$OPO$_3$H$_2$ prodrug (4-(2-(4-fluoro-2-methylphenoxy)-4-
(trifluoromethyl)benzamido)-2-oxopyridin-
1(2H)-yl)methyl dihydrogen phosphate)
WO2015089361 and US20140213616  VX-150

((2S)-2-[[3-cyclobutyl-5-(3,4,5-
trifluorophenoxy)imidazo[4,5-b]pyridin-2-
yl]methylamino]propanamide)
US20110294804  DSP-2230

Other nonlimiting examples of subtype Nav1.8 sodium channel blockers, particularly small molecule compounds, are available in the art, for example, in the following patents and published patent applications, which are incorporated by reference herein: US 2010/0105651; US 2010/0240652 (pyridine derivatives); and WO 2013/061205 ((4-phenylimidazol-2-yl) ethylamine derivatives).

Similarly, potassium channel antagonists for use in the methods of the invention are not meant to be limiting. Nonlimiting examples of potassium channel inhibitors, blockers, or antagonists for use in the treatment methods described herein include molecules, compounds and agents, preferably pharmaceutically and/or physiologically acceptable molecules, compounds and agents, that are available for blocking potassium channels, as well as those compounds and agents that are chemical derivatives of known potassium channel antagonists, that are in development, in clinical trials, or that may be developed to target and antagonize such ion channels. Particularly preferred are potassium channel antagonists that block the expression and/or activity of KCNQ1 and potassium channels similar to KCNQ1. Illustrative potassium channel antagonists for use in the treatment methods described herein may include, without limitation, 3,4-Diaminopyridine (amifampridine), 4-Aminopyridine (fampridine/dalfampridine), Adekalant, Almokalant, Amiodarone, Azimilide, Bretylium, Bunaftine, Charybdotoxin, Clamikalant, Conotoxins, Dalazatide, Dendrotoxin, Dofetilide, Dronedarone, E-4031, Hanatoxin, Ibutilide, Inakalant, Kaliotoxin, Linopirdine, Maurotoxin, Nifekalant, Notoxin, Paxilline, Pinokalant, ShK-186, Sotalol, Tedisamil, Terikalant, Tetraethylammonium, Vernakalant; the G-protein-gated inwardly rectifying potassium (GIRK) channels blocker Tipepidine. Other suitable potassium channel antagonists include the KCNQ1-specific blockers Chromanol 293B, HMR-1556, UCL2077, JNJ303, L-735821 (L-7), or fenofibrate. KCNQ1-specific inhibitors that can be used in the methods of of the invention are presented below in Table 2. Also provided are pharmaceutically acceptable salts and hydrates of the compounds listed in Table 2.

TABLE 2

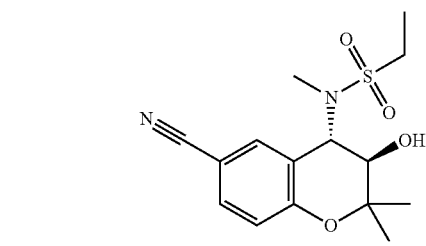

Chromanol 293B (trans-6-cyano-4-(N-ethylsulfonyl-N-methylamino)-3-hydroxy-2,2-dimethyl-chroman)
Lerche, C. et al.; (2007) *Molecular Pharmacology*, 71(6): 1503-1511

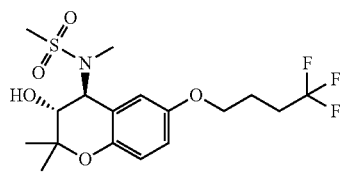

(N-[(3R,4S)-3,4-Dihydro-3-hydroxy-2,2-dimethyl-6-(4,4,4-trifluorobutoxy)-2H-1-benzopyran-4-yl]-N-methylmethanesulfonamide)
Thomas et al (2003) *J. Cardiovasc. Pharmacol.* 41(1): 140-147

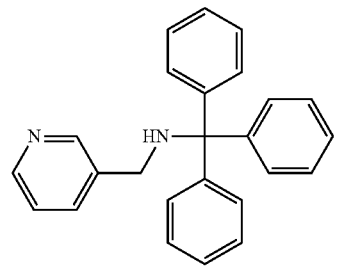

(N-Trityl-3-pyridinemethanamine)
Soh, H. et al. (2010) *Mol. Pharmacol.* 78(6): 1088-1095

TABLE 2-continued

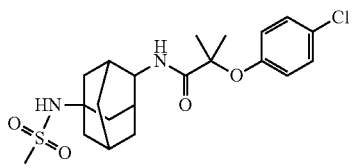

(2-(4-Chlorophenoxy)-2-methyl-N-[5-[(methylsulfonyl)amino]tricyclo [3.3.1.13,7]dec-2-yl]-propanamide)
Towart, R. et al (2009) *J. Pharm. Toxicol. Meth.* 60: 1-10

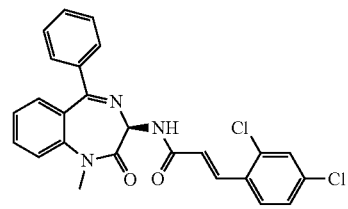

(L-7) ((E)-(+)-N-[(3R)-2,3-dihydro-1-methyl-2-oxo-5-phenyl-1H-1,4-benzodiazepin-3-yl]-3-(2,4-dichlorophenyl)-2-propenamide)
Du, L-P; et al. (2005) *Biochemical and Biophysical Research Communications*, 332(3): 677-687

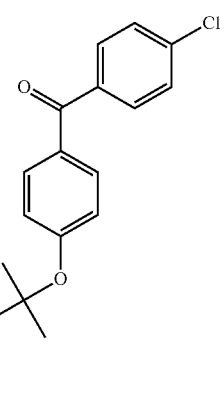

Fenofibrate (propan-2-yl 2-{4-[(4-chlorophenyl)carbonyl]phenoxy}-2-methylpropanoate) Bajwa, P J; et al. (2007) *Am. J. Physiol. Gastrointest. Liver Physiol.* 293(6): G1288-99.

For therapeutics, a subject having, suspected of having, or at risk of having, a neurological or neurodevelopmental disease or disorder that can be treated by antagonizing the expression of the sodium channel, namely, SCN10a, polynucleotide or protein is treated by administering an SCN10a antagonist in accordance with the methods of the invention. For example, in a non-limiting embodiment, the methods comprise the step of administering to a subject in need of treatment a therapeutically effective amount of a SCN10a sodium channel antagonist to block or inhibit the expression and/or the activity of SCN10a in CNS neuronal cells in the subject by about 10% or at least about 10%, e.g., as compared to a control, such as an untreated sample, or untreated subjects. Preferably, the expression and/or activity of SCN10a in CNS neuronal cells in the subject is blocked or inhibited by about 30% or at least about 30%. More preferably, the expression and/or activity of SCN10a in CNS neuronal cells in the subject is inhibited by about 50% or by at least 50%. Accordingly, the SCN10a antagonist blocks or inhibits SCN10a expression or protein by at least 10%, by at least 15%, by at least 25%, by at least 30%, by at least 35%, by at least 40%, by at least 50%, by at least 55%, by at least 60%, by at least 65%, by at least 70%, by at least 75%, by at least 80%, by at least 85%, by at least 90%, by at least 95%, by at least 98%, by at least 99%, or by 100%, as well as by values between these percentage amounts, e.g., as compared to a control such as an untreated subject or a sample from an untreated subject.

Dosage Forms and Administration

The sodium and/or potassium channel antagonists may be administered or delivered in a number of dosage forms as known and practiced in the art. The type of dosage form will, of course, depend on whether the antagonist is a small molecule chemical compound, a nucleic acid molecule, such as siRNA or miRNA, or a biologic, such as an antibody molecule or fusion protein. Dosage forms can include, without limitation, oral, injectable, transdermal, chewable products, capsules, capsules containing coated particles, nanoparticles, capsules containing delayed release particles, capsules containing extended release particles, concentrates, creams and augmented creams, suppository creams, discs, dressings, elixirs, emulsions, enemas, extended release films or fibers, gases, gels, metered gels, granules, delayed release granules, effervescent granules, implants, inhalants, injectable lipid complexes, injectable liposomes, inserts or devices, extended release inserts, intrauterine devices, jellys, liquids, extended release liquids, lotions, augmented lotions, oils, ointments, augmented ointments, pastes, pastilles, pellets, powders, reconstituted powders, extended release powders, metered powders, solutions, drops, concentrated solutions, gel forming solutions/drops, sponges, sprays, metered sprays, suppositories, suspensions, suspensions/drops, extended release suspensions, syrups, tablets/pills, chewable tablets/pills, tablets/pills containing coated particles, delayed release tablets/pills, dispersible tablets/pills, effervescent tablets/pills, extended release tablets/pills, orally disintegrating tablets/pills, tapes, or troches/lozenges. The dosages may be provided as formulations, compositions, pharmaceutically acceptable formulations and compositions, physiologically acceptable formulations and compositions, including pharmaceutically and physiologically acceptable carrier, excipients, diluents, or vehicles as known and used in the art.

The route of administration to a subject in need is not intended to be limiting. Illustratively, administration can be via any suitable, convenient or preferred route of administration including oral, buccal, intravenous, intramuscular, subcutaneous, intradermal, intracranial, intralymphatic, intraocular, intraperitoneal, intrapleural, intrathecal, intratracheal, intrauterine, intravascular, intravesical, intranasal, ophthalmic, biliary perfusion, cardiac perfusion, spinal, sublingual, topical, transdermal, inhalation, endocervical, intravaginal, rectal, ureteral, or urethral. In certain embodiments, oral administration is preferable for small molecule antagonist compounds, agents or substances.

In preferred embodiments, delivery of the ion channel antagonists is preferably to the CNS, preferably, neuronal cells of the CNS, such as cells of the prefrontal cortex. Accordingly, a mode of administration that delivers an antagonist to the CNS and/or is in a form that is capable of crossing the blood-brain barrier is preferable for use in the described methods. Without limitation, conditions for administering or optimizing the physicochemical properties of drugs, such as SCN10a or KCNQ1 channel antagonists, may be optimized to allow or improve access of therapeutic drugs to the CNS. Depending on the drug and its properties, prodrug forms and chemical delivery systems may be utilized; direct injection or infusion of a drug into the brain parenchyma, or intrathecally or intraventricularly into the CNS may be utilized; and olfactory administration may be utilized as a means for delivering certain therapeutics to the CNS. Other approaches to CNS drug delivery include endogenous transporters (solute transporters); ATP-binding cassette transporters; cell penetrating peptide vectors; liposomes; and nanoparticles for enhancing uptake of drugs into the brain. These and other aspects of CNS drug delivery may be found, for example, in Begley, D. J., 2004, *Pharmacology & Therapeutics*, 104, pp. 29-45. In an embodiment, an antagonist of SCN10a is administered intrathecally to block SCN10a expression or function in neuronal cells of the CNS. In an embodiment, an antagonist of KCNQ1 is administered intrathecally to block KCNQ1 expression or function in neuronal cells of the CNS. In an embodiment, an implantable device is used for intrathecal delivery.

According to the invention, treatment of a subject in need thereof typically involves the use or administration of an effective amount or a therapeutically effective amount of a ion channel antagonist, in particular, an antagonist of the SCN10a sodium channel and/or an antagonist of the KCNQ1 potassium channel. Effective amount refers to the quantity (amount) of the compound, agent, substance, or composition thereof, and the like, that induces a desired response in the subject upon administration or delivery to the subject over a given time period. Optimally, an effective amount produces a therapeutic effect in the absence of, or with little or virtually no, adverse effects to, or cytotoxicity in, the subject undergoing treatment. Alternatively, any adverse effects associated with an effective amount are optimally outweighed by the therapeutic benefit achieved. It is also to be appreciated that an adverse effect may be abrogated or alleviated with a countervailing drug or medication as would be known or is able to be determined by a medical practitioner or clinician. An effective amount for a particular subject may vary depending on factors such as the condition being treated, the overall health of the subject, the method, route, and dose of administration and the severity of side effects.

As will be appreciated by those having skill in the art, a specific dose or dose level for any particular patient will depend upon a variety of factors, including the activity of the specific compound employed, the age, body weight, general health, sex, diet, time of administration, route of administration, rate of excretion, drug combination, the precise disorder being treated, and the severity of the disorder being treated. The dose also depends on the particular route of administration selected by the medical practitioner. Further refinement of the calculations necessary to determine an appropriate dosage for treatment is routinely made by those of ordinary skill in the art, for example, using appropriate assays and analytical procedures, such as has been described for certain compounds (e.g., Howitz et al., 2003, Nature, 425:191-196). Exact dosages can be determined based on standard dose-response studies. Therapeutically effective doses for treatment of afflicted subjects can be determined, for example, by titrating the amount of the active product given to the subject to arrive at the desired therapeutic effect, while minimizing side effects. Therapeutically effective amounts or dosages are known to those skilled in the art and/or are described in the pertinent reference texts and literature. Generally, dosage levels of between 0.001 mg/kg to 10 mg/kg of body weight, or between 0.01 mg/kg to 10 mg/kg of body weight daily are administered to a subject. The dosage range administered to the subject will generally be about 0.1 mg to 1.0 g, or about 0.5 mg to about 1.0 g, per subject per day, which may be administered in single or multiple doses. In an embodiment, the dosage range administered to the subject will be about 0.5 mg to 500 mg per day, or about 5 mg to 50 mg per subject per day. In embodiments, a subject is treated with a dosage of antagonist/drug that is at least about 0.1, at least about 0.5, at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100 mg/kg body weight.

A dose may be administered or given once per day, but may also be given in multiple doses per day, for example, once, twice, three times, or four times a day. Alternatively, a dose may be administered or given every other day or every three days, four days, or five days, or weekly or monthly, e.g., once or more per week, or once or more per month. Discrete doses between the end points of the ranges are also contemplated. The precise amount of an antagonist administered to a subject will be the responsibility of the attendant physician and the route of administration. The skilled practitioner can readily determine optimum dosages, dosing methodologies and repetition rates. A medical practitioner in the art can easily estimate repetition rates for dosing based on measured residence times and concentrations of the drug in bodily fluids or tissues. Also, the route of administration may vary depending on the disease or disorder being treated and its severity. Following successful treatment, it may be desirable to have the subject undergo maintenance therapy to prevent the recurrence of the disease state or symptoms, such that the ion channel antagonist is administered in maintenance doses, ranging from 0.01 µg to 100 mg per kg of body weight, once or more daily.

Dosing can depend on a course of treatment and may last from several days to several months, or until a cure is effected, or a reduction or diminution of the disease state and/or one or more of its symptoms is achieved. Optimal dosing schedules can be calculated from measurements of drug accumulation in the body of the subject. Optimum dosages may vary depending on the relative potency of individual active pharmaceutical ingredients, and can generally be estimated based on $EC_{50}$s found to be effective in in vitro and in vivo animal models, and can also be determined from the prescribing information for each of the approved and marketed drugs.

The methods of the invention are useful for treating and/or reducing symptoms of certain neurological or neurodevelopmental diseases or disorders, as described herein, both therapeutically and prophylactically. Thus, the present methods may be used to treat and/or reduce symptoms in a subject who has an appropriate neurological or neurodevelopmental disease or disorder, who is suspected of having the disease or disorder, or who is at risk of having the disease or disorder. The methods of the invention embrace pediatric treatment, adult treatment, adolescent treatment, and also prenatal or in utero treatments. While human subjects, individuals and patients are preferred, the invention also embraces the treatment of other, typical, warm-blooded mammalian subjects, such as, for example, mice, rats, cats, dogs, horses, sheep, cows, rabbits, goats and non-human primates, e.g., monkeys, apes, chimps, gorillas, etc.

In general terms, "treating" a subject according to the present methods refers to achieving or obtaining a desired physiologic and/or pharmacologic effect, whether prophylactic, therapeutic, or both. As used herein "treating" or "treatment" can refer to ameliorating, preventing, inhibiting, blocking, reversing, attenuating, alleviating, abrogating, minimizing, suppressing, reducing, decreasing, diminishing, stabilizing, eradicating, curing, or eliminating the deleterious effects of a neurological or neurodevelopmental disease or condition and/or its symptoms, such as those described herein, or the progression or worsening of the disease or condition or its symptoms. For example, successful treatment may involve reducing or alleviating one or more symptoms of a neurological or neurodevelopmental disease or condition, although not necessarily all of the symptoms, of the disease or condition, or attenuating the symptoms or progression of the disease or condition. Curing or eliminating the neurological disease or condition from the subject undergoing treatment is an optimal outcome of the practice of the methods of the invention.

In some embodiments, the effect of an SCN10a antagonist on the expression or activity of SCN10a in CNS neuronal cells may be evaluated or assessed by the cell autonomous developmental assay using IUE to knockdown TCF4 expression in the rat and then assaying the antagonist on the CNS, preferably, prefrontal cortex neurons, for reduction in the aberrant excitability of these cells, as well as in the mouse models of PTHS described herein. Other in vitro and in vivo assays as known in the art may also be used to assess the therapeutic efficacy of an antagonist. In embodiments, without limitation, human neurons derived from patient fibroblasts or generated from genetically modified cultured human neuronal cells or pluripotent stem cells may be used to test the therapeutic efficacy of an SCN10a antagonist in these assays.

In other embodiments, a block or decrease of SCN10a expression, e.g., mRNA or protein, in a sample, such as cells or tissues in vivo or in vitro treated using an SCN10a antagonist, may be evaluated by comparison with SCN10a expression in a control sample. For example, expression of the protein or nucleic acid can be compared using conventionally known methods with protein or nucleic acid expression in a mock-treated or untreated sample. Alternatively, comparison with a sample treated with a control inactive molecule can be made depending on the information desired. In another embodiment, a difference in the expression of the SCN10a protein or nucleic acid in a treated versus an untreated sample can be compared with the difference in expression of a different nucleic acid, including any standard deemed appropriate by the practitioner, e.g., a housekeeping gene, in a treated sample versus an untreated sample. Methods for assaying sodium channel protein and mRNA expression, such as SCN10a protein and mRNA expression, as well as quantification of sodium channel protein, such as SCN10a herein, are known to those having skill in the art and are described, for example, in US 2014/0309181.

Observed differences can be expressed, for example, in the form of a ratio or fraction, if desired, for comparison with a control. By way of example, the level of SCN10a mRNA or protein in a sample treated with an antagonist that comprises an antisense oligonucleotide, is decreased by about 1.25-fold to about 10-fold or more relative to an untreated sample, or to a sample treated with a control nucleic acid. In other examples, the level of SCN10a mRNA or protein is decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

In addition to decreases in SCN10a protein or mRNA expression, changes in the function of the Nav1.8 channel may be quantified. For example, changes in the sodium current amplitude induced by a decrease or reduction in SCN10a expression or activity (excitability) by an SCN10a antagonist compound can be measured in the appropriate neuronal cells, such as prefrontal cortical neurons, e.g., prefrontal cortex pyramidal cells.

Such assays may also be used to screen potential therapeutics, e.g., small molecule libraries, antibody libraries, RNAi species, etc., for compounds that are effective in treating, preventing or ameliorating the symptoms of neurological or neurodevelopmental diseases and disorders, such as Pitt-Hopkins Syndrome (PTHS), autism, autism spectrum disorder, 18q syndrome and schizophrenia. For example, the invention provides screening methods comprising contacting in vitro a CNS neuronal cell that over-expresses SCN10a, such as a human neuronal cell that has a mutation in one or both copies of the TCF4 gene resulting in SCN10a ectopic expression, or that recombinantly expresses SCN10a and/or KCNQ1, with a compound to be tested and determining whether contacting the cell with the compound increases the AP output (frequency and/or amplitude) or decreases AHP, in comparison to a control cell, or reduces the expression of SCN10a and/or KCNQ1 in the cell in comparison to a control cell, thereby identifying an SCN10a antagonist or a KCNQ1 antagonist.

EXAMPLES

Example 1

Validation of shRNA Constructs to Create a Cell Autonomous Model of TCF4 Haploinsufficiency Experiments were performed to more precisely characterize the developmental expression patterns of TCF4 in both rat and human to determine critical periods of expression. Analogous expression trajectories were observed in both human and rat, thus suggesting developmental regulation of TCF4 may be similar between species. TCF4 mRNA expression peaks in late prenatal life, corresponding to the third trimester of fetal life in humans and postnatal day 1 (P1) in rat and declines during early childhood before leveling off into adulthood (FIG. 1A). The rapid rise in TCF4 transcripts during corticogenesis likely implicates a critical time period for TCF4 biology. Accordingly, the developmental expression pattern of TCF4 across the lifespan is similar between humans and rodents.

To gain insight into the function of TCF4 during this prenatal peak in expression and to create a cellular model of PTHS, two shRNA constructs were designed and validated to specifically knockdown TCF4 in utero at embryonic day 16 (E16), just prior to its rise in late prenatal life. Each shRNA construct targets a unique region of the rat TCF4 transcript; shTCF4 targets a common 3' exon found in all known TCF4 isoforms; and shTCF4_2 targets a common 3'UTR. Both shRNA constructs were validated in vitro and showed consistent knockdown of endogenous TCF4 mRNA ($p<0.002$) and TCF4 protein ($p<0.0001$) in transfected rat neuroblastoma cells compared to a control shRNA (shCon) that does not target any known rat sequence, but is processed by the cell into a functioning interfering RNA (FIGS. 1B-1D).

Figures 8A, 8B, 8C, 8D:
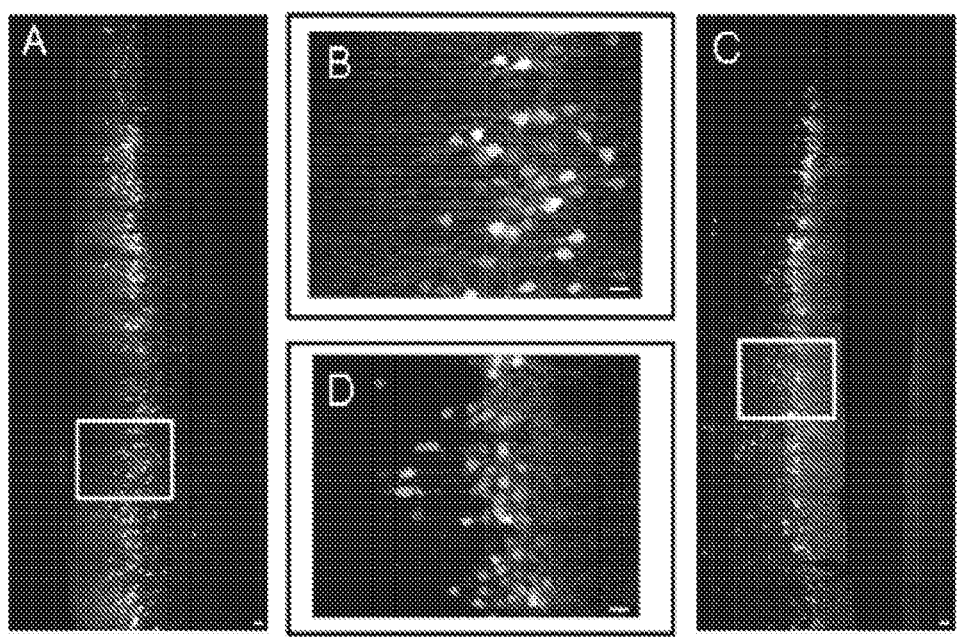
FIGS. 8A-8D show that suppression of TCF4 has no effect on gross neuronal morphology or migration. (A) 5× confocal image of rat medial prefrontal cortex transfected by IUE with shTCF4+EGFP. Neuronal migration and gross neuronal morphology (B, 20×) appear normal. (C) 5× confocal image of rat medial prefrontal cortex transfected by IUE with shCon+EGFP. Neuronal migration and gross morphology (D, 20×) appear normal. All scale bars=50 μm.

In utero electroporation targeted the medial prefrontal cortex (mPFC), which is the generally accepted rodent homologue of human prefrontal association cortex, an important brain region associated with cognitive deficits in psychiatric disorders. FIGS. 8A-8D and depict an example image of mPFC electroporation according to the Example. TCF4 knockdown by shTCF4 did not produce any gross morphological defects in neuronal migration or morphology (FIGS. 8A and 8B).

Example 2

TCF4 Regulates the Intrinsic Excitability of Prefrontal Cortical Neurons

Figures 10A, 10B, 10C:
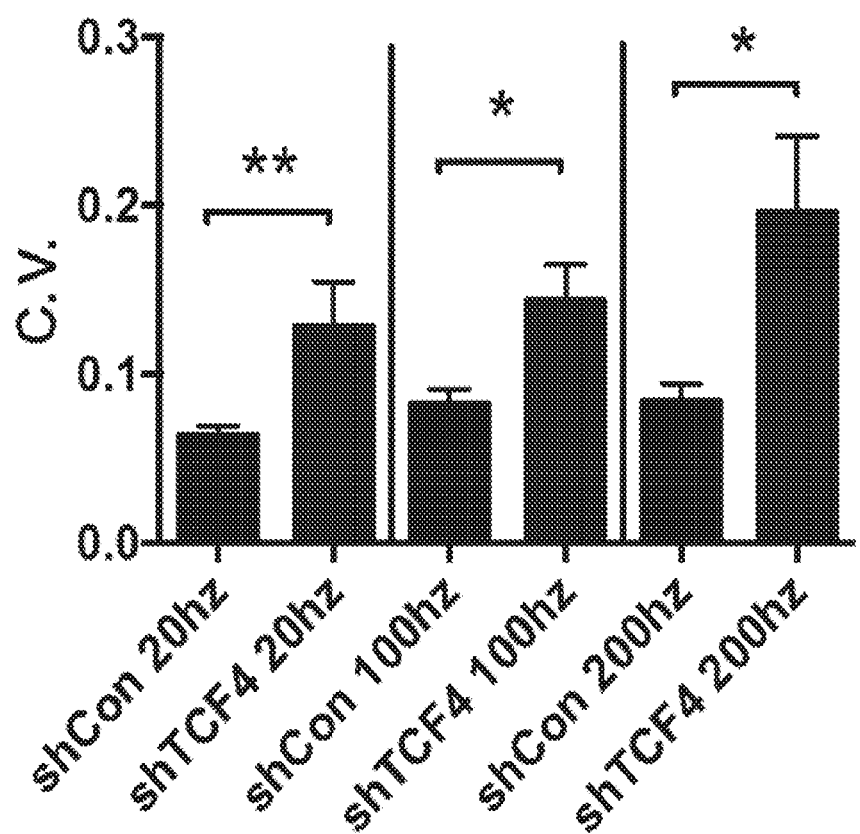
FIGS. 10A-10C show abnormal AP output in response to physiologically relevant synaptic inputs. Dynamic clamp was used to simulate synaptic input at three different frequencies. A representative current-clamp recording from an shCon (A) and shTCF4 (B) neuron showing the response to a 20 Hz burst of simulated synaptic inputs from six presynaptic neurons. shTCF4 neurons showed a significantly higher coefficient of variance in the AP amplitude across three frequencies (C).

To determine if in utero suppression of TCF4 negatively impacts the physiology of cortical neurons, the intrinsic excitability was assayed by performing whole-cell recordings from IUE transfected neurons, and the frequency of AP spiking elicited by a series of depolarizing current pulses was measured. TCF4 knockdown produced a severe and consistent reduction of AP output frequency compared to shCon cells (FIGS. 2A and 2B; $p<0.0001$). The maximum number of spikes elicited by any size current pulse for each cell was also significantly reduced by both TCF4 shRNA constructs (FIG. 2C; $p<0.0001$). Several other intrinsic excitability measurements were obtained from these recordings (FIG. 9 and FIGS. 10A-10C), and the only consistent effect observed between both shTCF4 and shTCF4_2 was an increase in the resting membrane potential (RMP), (FIG. 9; $p<0.001$) and the peak amplitude of the AP (FIG. 9; $p<0.03$). Consistent with these intrinsic excitability deficits, an increased variance of AP amplitudes was also observed in response to simulated trains of synaptic inputs (FIGS. 10A-10C).

Targeted knockdown of gene expression by RNA interference is potentially complicated by off-target knockdown due to sequence-dependent and sequence-independent effects (Alvarez et al., 2006; Baek et al., 2014). In addition to showing phenotypic overlap using two independent TCF4 shRNA constructs, sequence-dependent effects were controlled for by performing rescue experiments. Co-expression of human TCF4B+shTCF4 resulted in a complete rescue of AP output (FIGS. 2B and 2C). To control for sequence-independent off-targets effects, a CRISPR-Cas9 construct was designed to mutate/knockout Tcf4 (crTCF4). In vitro validation of crTCF4 in transfected rat neuroblastoma cells showed that it crTCF4 was effective in making targeted mutations in the Tcf4 locus as measured by the SURVEYOR nuclease assay (FIG. 11A) and was effective at knockdown of endogenous TCF4 (FIG. 11C). crTCF4 was delivered via IUE and produced a significant reduction in the frequency neuronal spiking compared to crEmpty cells (FIGS. 2D and 2E; $p<0.0001$). Maximum spiking frequency analysis showed that crTCF4 cells were significantly reduced compared to crEmpty cells ($p=0.0016$). Phenocopy by crTCF4 indicates that the altered intrinsic excitability associated with shRNA suppression of TCF4 is primarily due to disruption of TCF4 signaling and is not the result of off-target effects.

Example 3

TCF4 Regulates the Afterhyperpolarization in mPFC Neurons

To more fully characterize the molecular mechanism responsible for the reduction of AP output in shTCF4 neurons, the afterhyperpolarization current (AHP) that regulates neuronal spike frequency was measured. $Ca^{2+}$-activated potassium channels hyperpolarize the membrane, making it less likely that neurons will reach threshold and fire subsequent APs. Several K+ channel conductances are responsible for producing the AHP, and they are characterized by their kinetics such that the AHP consists of a fast (fAHP), a medium (mAHP) and a slow component (sAHP) (Sah and Louise Faber, 2002). Because the mAHP and sAHP are inversely correlated with average firing rate, and the amplitude of the sAHP depends on the number of spikes (Abel, 2003; Lorenzon and Foehring, 1995), the mAHP and sAHP were measured from traces showing spiking frequencies of 12±1.0 Hz (FIG. 2C), which corresponds to the median of the maximum spiking for shTCF4 cells. Both the mAHP ($p<0.0001$) and sAHP ($p=0.0003$) were significantly larger in shTCF4 cells compared to shCon cells (FIGS. 3B and 3C). No significant difference was found in the fAHP between shTCF4 and shCon cells ($p=0.33$). In addition, the mAHP ($p=0.029$), but not the sAHP ($p=0.28$), was observed to be larger in crTCF4 cells compared to crEmpty cells (FIG. 11). These results indicate that TCF4 regulates neuronal output spiking through its control of the AHP.

To further validate the role of TCF4 in regulating the AHP and to more precisely pinpoint the underlying conductances responsible for the increase in the AHP, voltage-clamp experiments were conducted to isolate specific $Ca^{2+}$-activated K+ channel currents. shTCF4 neurons were observed to display significantly larger capacitance-normalized charge transfer compared to shCon neurons ($p=0.008$). Progressive pharmacological blockade was then used to isolate specific components of the AHP. The fAHP is primarily produced by the large conductance calcium-activated big potassium channels (BK) and is blocked by the nonselective antagonist TEA (1 mM). The AHP current from TCF4 knockdown neurons remained significantly increased in the presence of TEA (FIGS. 3E and 3G; $p=0.0096$). The mAHP is produced by the small conductance $Ca^{2+}$-activated potassium channels (SK) and is selectively sensitive to apamin (Sah and Louise Faber, 2002). Application of apamin (100 nM) blocked the mAHP in both conditions, and the remaining sAHP current was still significantly increased in shTCF4 cells compared to shCon cells (FIGS. 3F and 3G; $p=0.013$). Because apamin is highly selective for SK channels, the AHP current traces generated before and after its application were subtracted to isolate the apamin-sensitive component (FIG. 3H). This subtraction did not reveal a significant difference ($p=0.53$) in the apamin-sensitive current between the conditions assessed (FIG. 3I), suggesting that SK channel expression does not appear to be altered by TCF4 knockdown. From these results the exact identity of the responsible conductance remains unknown, however these data replicate the current-clamp results (FIGS. 3A-3C) and strengthen the conclusion that TCF4 is regulating neuronal spiking via the AHP.

Example 3

Figure 12:
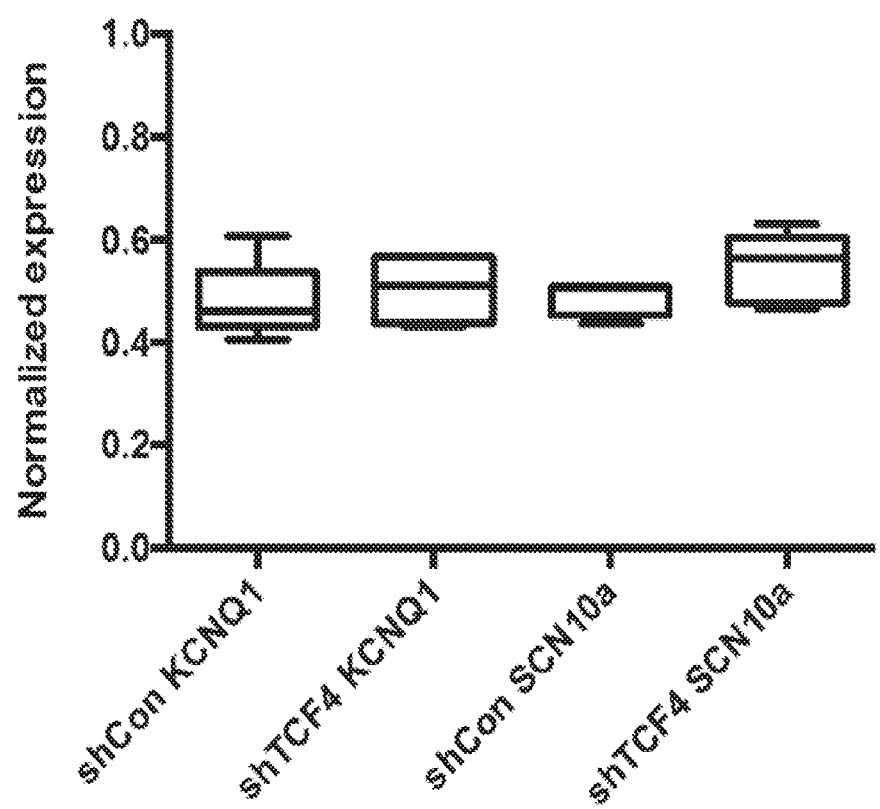
FIG. 12 demonstrates cell-type enrichment via iTRAP is necessary to detect increased expression of KCNQ1 and SCN10a. qRT-PCR of bulk RNA (input RNA) from frontal cortex homogenates. No differences in the expression of KCNQ1 or SCN10a was observed between shTCF4 and shCon transfected brains.

TCF4 Regulates the Expression of KCNQ1 and SCN10a, Two Ion Channel Genes that Regulate Spike Frequency Adaptation As described in the above Examiner, TCF4 was determined to associate significantly with the AHP; however, voltage-clamp experiments did not identify the exact conductance(s) regulated by TCF4. Therefore, molecular profiling was used to identify the particular genes responsible for the intrinsic excitability phenotype by adapting translating ribosome affinity purification (TRAP) (Heiman et al., 2014; 2008) for use with IUE, in a novel approach termed "iTRAP" herein. The EGFP-fused ribosomal protein L10a-EGFP was co-expressed with either shTCF4 or shCon, and affinity purification was carried out from IUE transfected mPFC brains on P21. A major advantage of this technique is that IUE specifically transfects a homogenous population of layer specific excitatory neurons (Langevin et al., 2007), and iTRAP was validated to enrich for excitatory neurons by comparing the expression of cell-type specific markers between the EGFP affinity-bound RNA fraction and the unbound RNA fraction. Consistent with excitatory neuronal enrichment, an approximate 2-fold decrease was found in the expression of GAD1 ($p=0.007$), GFAP ($p=0.01$), and OLIG1 ($p=0.0003$) in the EGFP-bound fraction compared to unbound fraction (FIG. 4B). In addition, a greater than 400-fold increase was observed in the expression of EGFP ($p=0.0006$). The ion channel translatome of TCF4 knockdown neurons was then compared to shCon neurons using prefabricated 384-well qPCR plates containing the majority of known ion channel genes in the rat genome. This analysis revealed only two ion channel genes, Kcnq1 (Kv7.1; $p<0.005$) and Scn10a (Nav1.8; $p<0.01$) that were significantly upregulated in shTCF4 neurons compared to shCon neurons. Enrichment via the iTRAP protocol was demonstrated to be required, because Kcnq1 and Scn10a expression was not significantly different when measured from total RNA from whole frontal cortex homogenates (FIG. 12). Both of these genes have been implicated in regulating spike frequency adaptation (Blair and Bean, 2003; Delmas and Brown, 2005) and thus were strong candidate genes underlying the excitability phenotype observed in the neurons evaluated.

To determine if TCF4 bound directly to KCNQ1 and SCN10a, the publicly available ENCODE datasets of TCF4 ChIP-seq performed in human K562 cell line (Consortium, 2012) were analyzed. After aligning the raw reads to the genome and calling peaks (Ji et al., 2008), two genome-wide significant (at FDR<5%) peaks were identified in both of these genes. In KCNQ1, both peaks (chr11:2799700-2800099, FDR=0.005 and chr11:2760400-2760749, FDR=0.013) were located in intronic sequence, and both contained multiple canonical E-box binding motifs (CANNTG, first peak: 2, second peak: 9). Similarly, in SCN10a, both peaks (chr3:38765550-38766049, FDR<1×$10^{-4}$ and chr3:38767100-38767499, FDR<1×$10^{-4}$) were located in intronic sequence and both contained multiple canonical E-box binding motifs (CANNTG, first peak: 2, second peak: 6).

ChIP-seq of endogenous TCF4 was performed in rat neuroprogenitor cell cultures to confirm these results in the rodent system. Multiple significant peaks were again found in both genes (compared to an untreated input sample, see Methods), including 12 genome-wide significant peaks in and around (within 20 kb) Kcnq1 and 4 genome-wide significant peaks in and around Scn10a (FIG. 16). These results in both human and rat indicate that TCF4 directly binds to genomic regions within KCNQ1 and SCN10a and indicates that TCF4 may directly regulate the expression of these genes.

Example 4

Figure 5A:
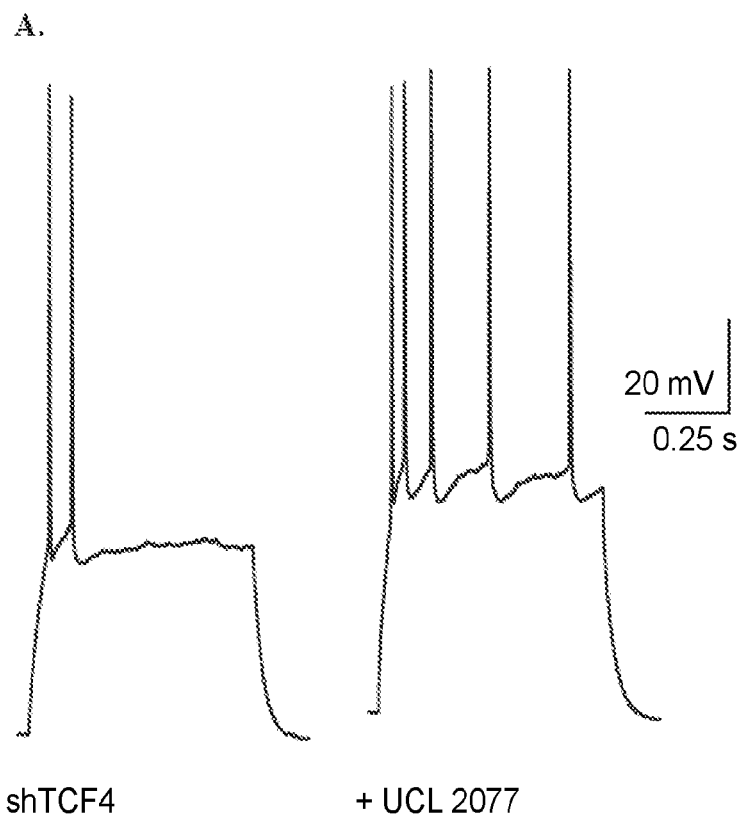
FIGS. 5A-5N shows that a pharmacological block of KCNQ1 rescues phenotypes associated with suppression of TCF4. (A) Representative current-clamp traces from an shTCF4 cell showing the effect of UCL2077 (10 µM) on the frequency of AP spiking. (B) Summary data of the effect of UCL2077 application on the frequency of APs in shTCF4 cells generated in response to current injections (N=17). Post hoc analysis indicates UCL2077 significantly increased firing frequency for current pulses between 250 and 500 pA. (C, D) Before and after plots depicting the effect of UCL2077 application on the amplitudes of the mAHP (before −4.43±0.55 mV vs. after −3.736±0.49 mV, N=19, paired t-test p=0.003) and sAHP (before −2.88±0.42 mV vs. after −2.53±0.38 mV, N=19, paired t-test $p<0.05$ on shTCF4 cells. (E) Summary data of the effect of UCL2077 application on the frequency of APs in shCon cells generated in response to increasing current injections (N=8). (F, G) Before and after plots depicting the effect of UCL2077 application on the amplitudes of the mAHP (before −3.78±0.66 mV vs. after −4.01±0.66 mV, N=9, paired t-test p=0.20) and sAHP (before −2.60±0.42 mV vs. after −2.69±0.48 mV, N=9, paired t-test p=0.68) on shCon cells. (H) Representative current-clamp traces from an shTCF4 cell showing the effect of JNJ303 (1 µM) on the frequency of AP spiking. (I) Summary data of the effect of JNJ303 application on the frequency of APs in shTCF4 cells generated in response to current injections (N=8). Post hoc analysis indicates JNJ303 significantly increased firing frequency for current pulses between 250 and 500 pA. (J, K) Before and after plots depicting the effect of JNJ303 application on the amplitudes of the mAHP (before −3.52±0.58 mV vs. after −2.77±0.36 mV, N=8, paired t-test p<0.044 and sAHP (before −2.31±0.46 mV vs. after −1.71±0.33 mV, N=8, paired t-test p=0.041) on shTCF4 cells. (L) Summary data of the effect of JNJ303 application on the frequency of APs in shCon cells generated in response to increasing current injections (N=8). (M, N) Before and after plots depicting the effect of JNJ303 application on the amplitudes of the mAHP (before −5.93±0.58 mV vs. −5.61±0.74 mV, N=9, paired t-test p=0.91) and sAHP (before −4.67±0.48 mV vs. after −4.22±0.57, N=9, paired t-test p=0.20) on shCon cells.
Figure 5N:
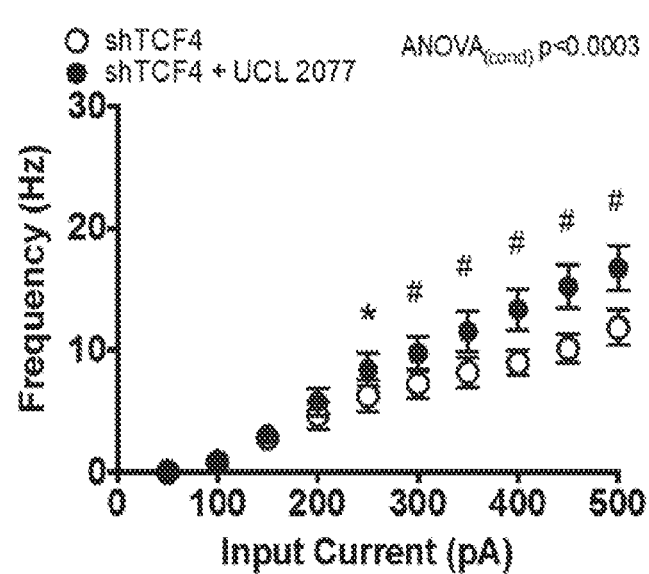
Figure 5A:
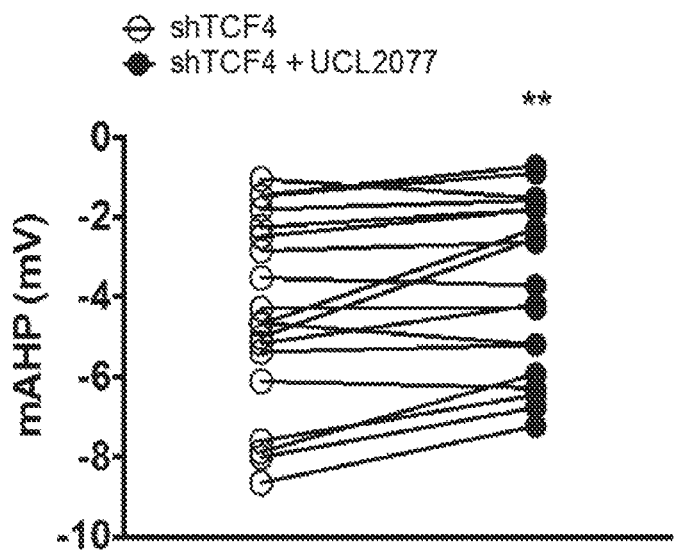
Figure 5N:
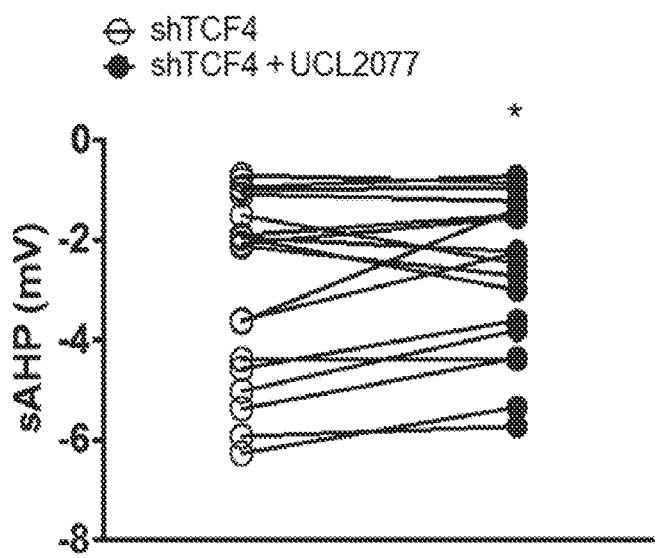
Figure 5A:
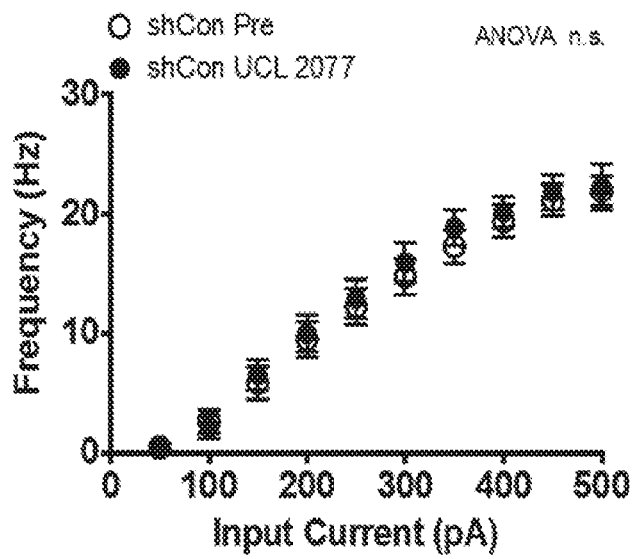
Figure 5N:
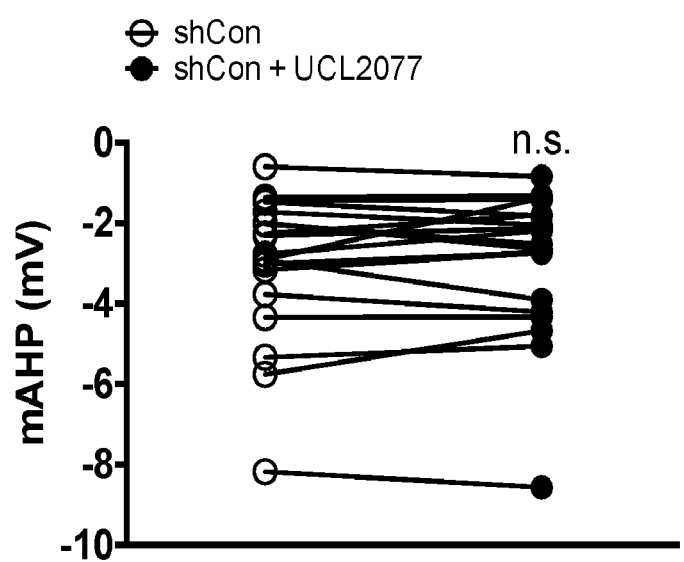
Figure 5A:
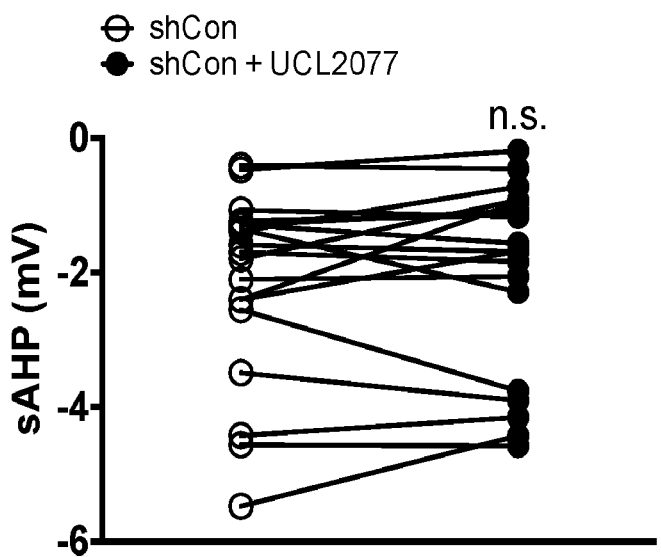
Figure 5N:
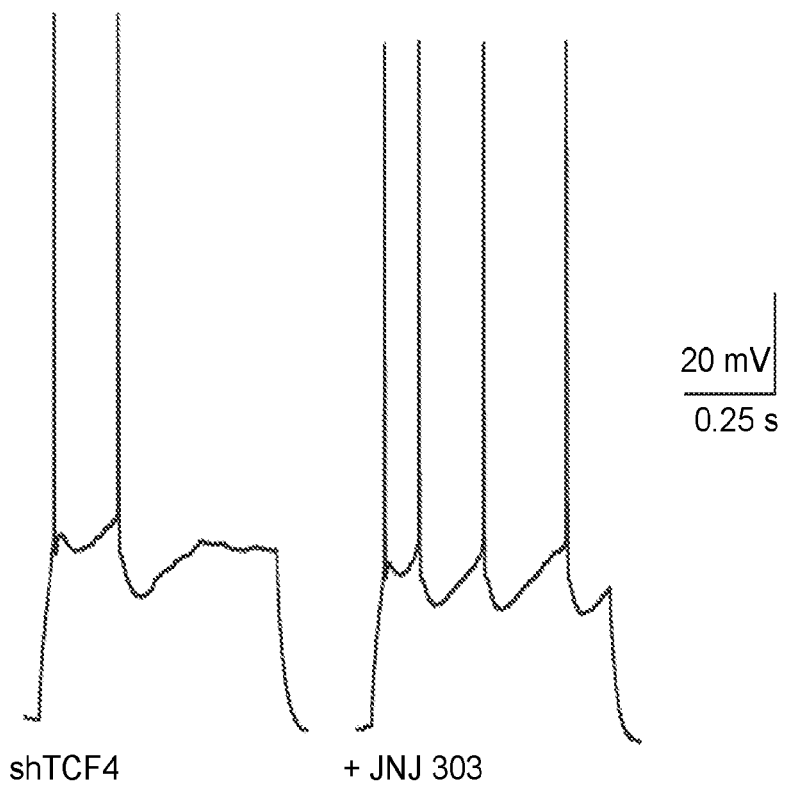
Figure 5A:
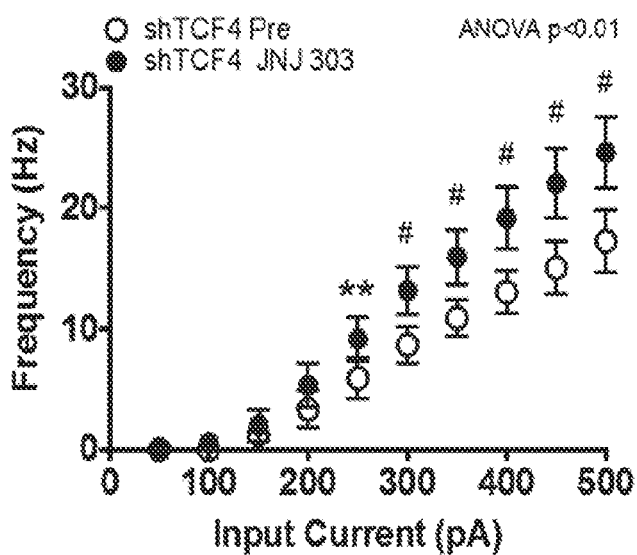
Figure 5N:
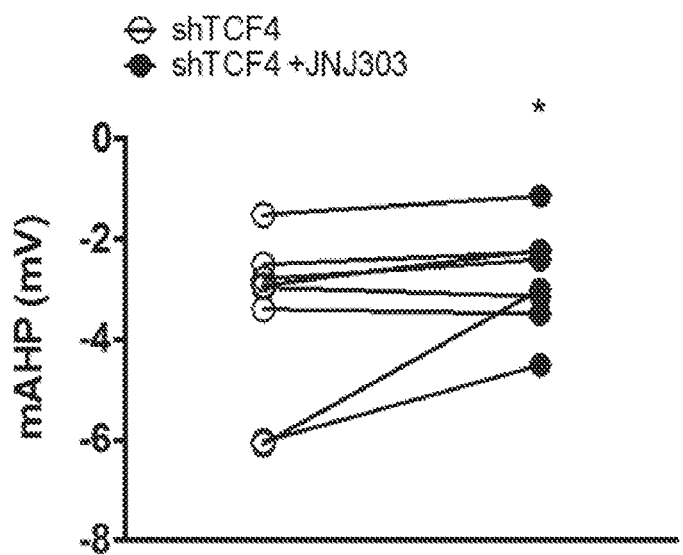
Figure 5A:
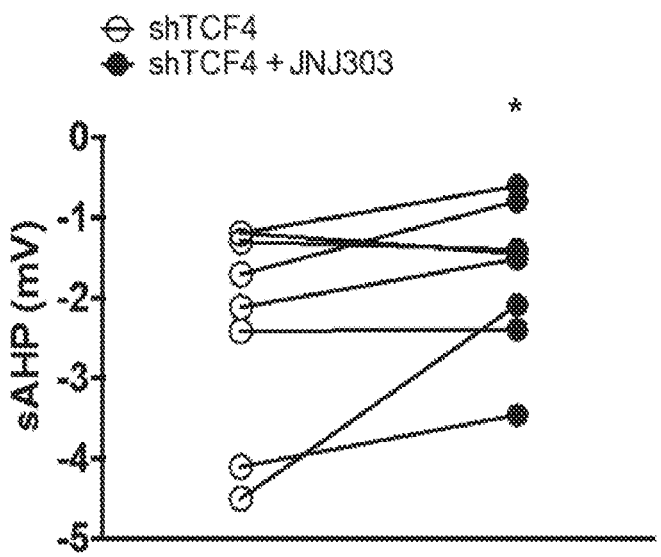
Figure 5N:
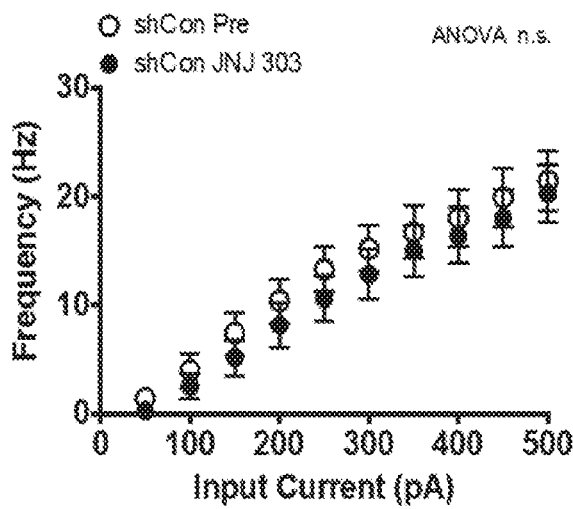
Figure 5A:
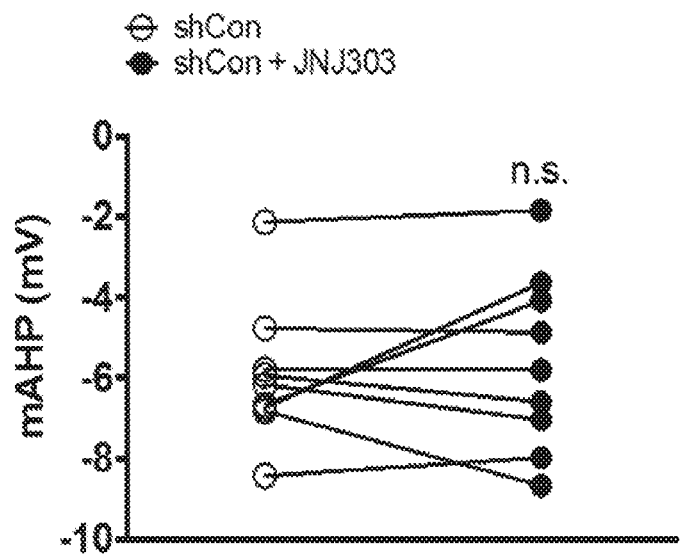
Figure 5N:
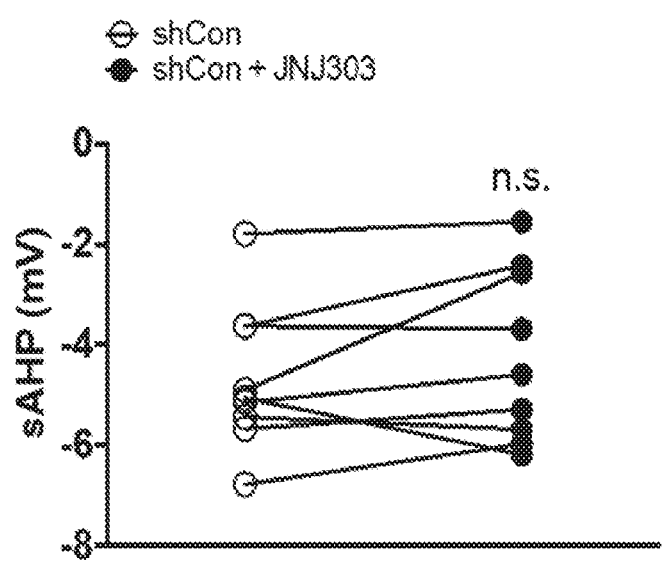

Molecular and Pharmacological Validation of SCN10a and KCNQ1 as Candidate Genes Associated with TCF4-Dependent Regulation of Intrinsic Excitability To validate the iTRAP experiment and to further understand the underlying molecular mechanism responsible for the TCF4-dependent effects on intrinsic excitability, both pharmacological and molecular methods were employed to rescue and phenocopy the observed shTCF4 phenotypes. Two competitive antagonists with selectivity for KCNQ potassium channels, UCL2077 and JNJ303, were used. (Soh and Tzingounis, 2010; Towart et al., 2009). UCL2077 is a KCNQ subtype-selective blocker that strongly inhibits KCNQ1 and KCNQ2, while JNJ303 is a potent KCNQ1 antagonist ($IC_{50}$=64 nM) with unknown subtype selectivity (Towart et al., 2009). These antagonists were assessed using a within neuron design. It was observed that both UCL2077 (p=0.0002; CrTCF4 p=0.045, FIGS. 13A-13D) and JNJ303 (p=0.0084) were effective at increasing the spiking frequency in shTCF4 neurons (FIGS. 5A-5N). Importantly, neither UCL2077 (p=0.35) nor JNJ303 (p=0.11) had an effect on spiking in shCon cells (FIGS. 5E-5G and 5L-5N); UCL2077 on crEmpty cells p=0.99, FIG. 13C). In addition, the amplitudes of the mAHP and sAHP were measured before and after application of UCL2077 or JNJ303. Consistent with increased Kcnq1 expression contributing to the AHP amplitude, UCL2077 and JNJ303 were both effective at reducing both the mAHP (UCL2077 p=0.003; JNJ303 p=0.044) and sAHP (UCL2077 p=0.039, JNJ303 p=0.041) amplitudes in shTCF4 neurons. Notably, and in keeping with spike frequency data, neither UCL2077 nor JNJ303 had any consistent effect on the amplitudes of the mAHP (UCL2077 p=0.89; JNJ303 p=0.40) or sAHP (UCL2077 p=0.91, JNJ303 p=0.20) in shCon cells. These pharmacological results suggest that reduced firing frequencies observed in shTCF4 neurons are associated with enhanced KCNQ1 expression that results in a subsequent increase in the amplitude of the AHP. Because neither UCL2077 nor JNJ303 is perfectly selective for KCNQ1, the possibility exists that other KCNQ isoforms may contribute to this pharmacological effect. For example, KCNQ2 and KCNQ3 are highly expressed in the cerebral cortex. To rule out other KCNQ isoforms, similar experiments were conducted with the muscarinic antagonist carbachol (FIGS. 14A-14H). Blockade of the M-current by carbachol was effective at increasing spike frequency and blocking the mAHP and sAHP in both shTCF4 and shCon cells, suggesting other KCNQ isoforms are present in these cells. This result acts as a positive control and indicates the pharmacological assay was sensitive enough to measure KCNQ1-specific effects on spike frequency and AHP amplitude. Therefore, the fact that UCL2077 and JNJ303 only adjust firing and AHP amplitudes in shTCF4 neurons and not in shCon neurons strongly suggests that these drugs are specifically acting on KCNQ1 and that TCF4 is indeed regulating the expression KCNQ1 in these neurons.

Figure 15A:
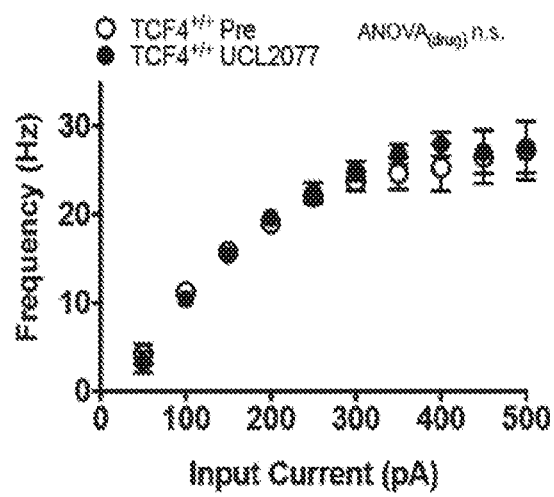
FIGS. 15A and 15B demonstrate that KCNQ1 and SCN10a antagonists have no effect on AP output in wildtype mice. (A) Summary data showing the KCNQ1 antagonist UCL2077 has no effect on action potential output in pre-frontal neurons from wildtype littermates (p=0.58, N=11). (B) Summary plot showing the SCN10a antagonist A-803467 has no effect on action potential output in pre-frontal neurons from wildtype littermates (p=0.06, N=5). These data support the use of antagonists of KCNQ1 and SCN10a activity targets in subjects having certain neurological diseases and disorders with minimal off target effects.
Figure 15B:
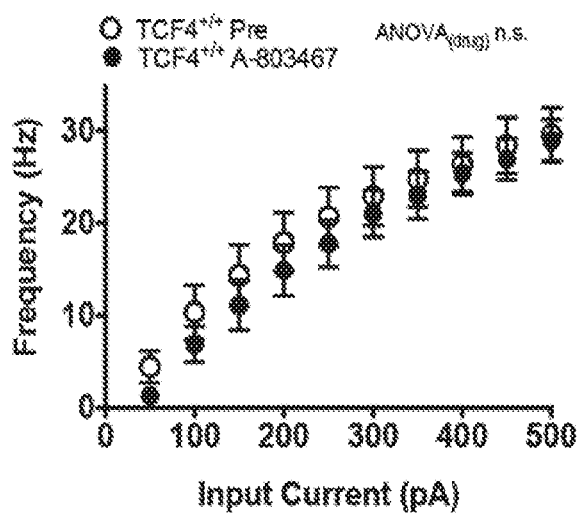

To validate SCN10a's involvement in pathophysiology, a recombinant Scn10a construct was overexpressed to phenocopy the knockdown of TCF4. IUE was used to co-transfect Scn10a+shCon, and this manipulation resulted in a consistent phenocopy of the intrinsic excitability deficits observed with TCF4 suppression. Scn10a+shCon expression produced a significant decrease in spiking frequency compared to shCon cells (FIG. 6B; p<0.0001) and also depolarized the RMP (p<0.0001) to a similar magnitude observed in TCF4 knockdown cells (FIG. 6C and FIGS. 10A-10C). In addition, bath application of a selective SCN10a antagonist (A-803467; 200 nM) was effective at increasing firing frequency in shTCF4 cells (FIG. 6D, p<0.05) and crTCF4 cells (FIGS. 15A and 15B, p=0.039). Importantly, A-803467 had no effect on firing frequency in shCon cells (p=0.14) or in crEmpty cells (p=0.15, FIG. 13D). The selective effect of A-803467 only on shTCF4 and crTCF4 cells, which strongly suggests that SCN10a is overexpressed in these neurons.

Figures 6A, 6B, 6C, 6D, 6E, 6F, 6G:
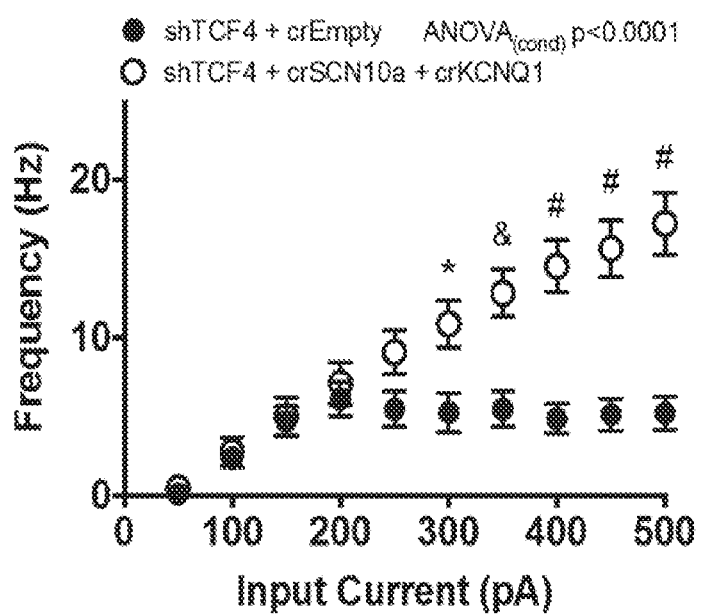
FIGS. 6A-6G depict molecular and pharmacological validation of the role of SCN10a underlying intrinsic excitability phenotypes in shTCF4 cells. (A) Sample current-clamp trace showing the effect of co-expressing SCN10a in an shCon cell on AP spiking. (B) Summary data of the effect of co-expressing SCN10a+shCon on the frequency of APs generated in response to increasing current injections. Post hoc analysis indicates that SCN10a expression significantly decreases firing for current pulses between 350 and 500 pA. (C) Summary plot showing the effect co-expression of SCN10a+shCon on the resting membrane potential (68.86±1.50 mV, N=29; post hoc p=0.0005). (D) Summary data of the effect of A-803467 (200 nM) application on the frequency of APs in shTCF4 cells generated in response to increasing current injections (N=11). Post hoc analysis indicates that A-803467 significantly increased firing for current pulses between 350 and 500 pA. (E) Summary data of the effect of A-803467 application on the frequency of APs in shCon cells generated in response to increasing current injections (N=7). For statistical comparisons in (B) and (C), shCon and shTCF4 data are the same datasets shown in FIG. 2 and FIG. 11. Values are presented as Tukey boxplots and statistical significance via Bonferoni post hoc analysis (* $p<0.05$, ** $p<0.01$, & $p<0.001$, #$p<0.0001$). (F) SURVEYOR assay showing CRISPR-Cas9 mediated mutation of Kcnq1 and Scn10a. (G) Summary data of the effect of co-expressing shTCF4+crSCN10a+crKCNQ1 on the frequency of APs generated in response to current injections. Post hoc analysis indicates that CRISPR-Cas9 mediated mutation of Scn10a and Kcnq1 significantly rescues AP firing for current pulses between 300 pA and 500 pA compared to co-expression of shTCF4+crEmpty.

To further rule out the potential of nonspecific pharmacology of antagonists to both KCNQ1 and SCN10a, CRISPR-Cas9 constructs that target both Kcnq1 and Scn10a were designed and validated (FIG. 6F). Co-expression of crKCNQ1, crSCN10a and shTCF4 resulted in complete rescue of AP spike output (FIG. 6G; p<0.0001). Together, these results robustly validate the described iTRAP method and indicate that under normal conditions, TCF4 represses the expression of KCNQ1 and SCN10a in layer 2/3 neurons of the rat prefrontal cortex.

Example 5

Phenocopy in a Mouse Model of PTHS

Figure 17:
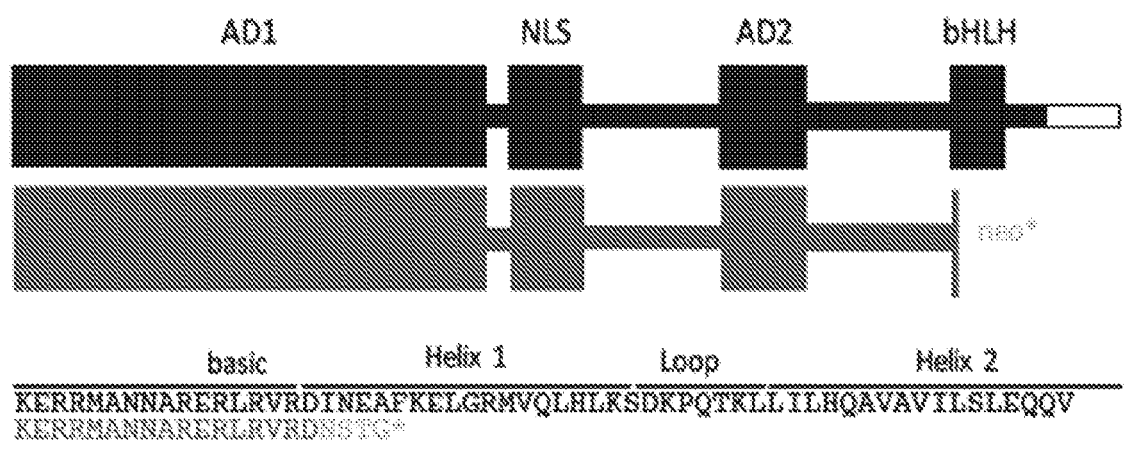
FIG. 17 presents a schematic diagram showing the C-terminal end of a full-length (top, black) and truncated (bottom, blue) TCF4 protein. The truncated protein contains two activation domains (AD1 and AD2), a nuclear localization sequence (NLS), but only a portion of the basic helix-loophelix (bHLH) domain. The amino acid sequence is shown below the truncated form (SEQ ID NO: 11).

To further validate the intrinsic excitability phenotypes that were observed in the cell-autonomous model of PTHS as described herein, input-output curves from mPFC neurons from a mouse model of PTHS (Grubisic et al., 2015; Sweatt, 2013) were measured. This mouse model was created by insertion of a neo cassette into EcoRV sites within the bHLH domain of TCF4 (FIG. 17), and was originally believed to result in a constitutive deletion of one allele of the TCF4 gene, thus modeling germline TCF4 haploinsufficiency (Flora et al., 2007).

Figures 7A, 7B, 7C, 7D, 7E, 7F, 7G, 7H, 7I:
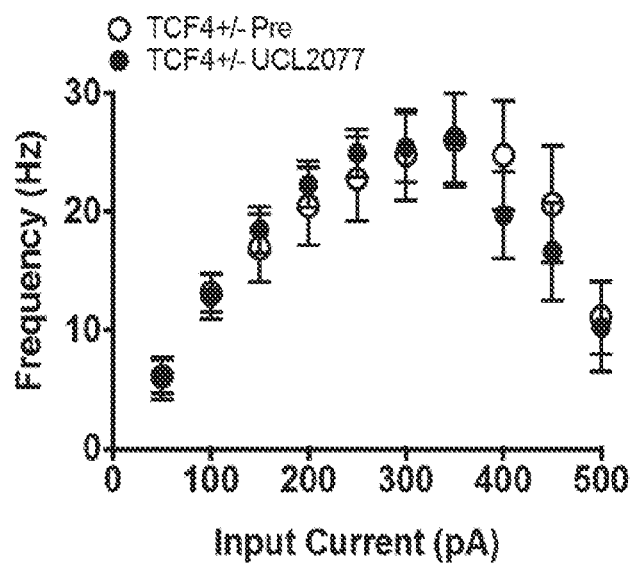
FIGS. 7A-7I demonstrate germline truncation of one allele of TCF4 phenocopies cell-autonomous knockdown of TCF4. Shown in (A) is a Western blot of TCF4 from E18 brain lysates. A single full-length TCF4 (TCF4fl) protein band is observed in lysates from wild-type (+/+) mouse brain and from expression of recombinant TCF4 (ox) in rat neuroblastoma cells. A truncated TCF4 (TCF4tr) protein is observed in lysates from heterozygous (+/−) and knockout (−/−) mouse brain. Shown in (B) are sample whole-cell current-clamp traces recorded from mPFC layer 2/3 neurons from a TCF4$^{+/tr}$ and a wild-type littermate (TCF4$^{+/+}$) in response to 600 ms current injections (+450 pA). (C) Summary data of the frequency of APs generated in response to current injections. Post hoc analysis indicated that TCF$^{+/tr}$ cells (N=46) between 300 and 500 pA produced significantly fewer spikes than TCF4$^{+/+}$ cells (N=35). (D) Summary data showing the resting membrane potential is significantly depolarized in TCF4$^{+/tr}$ neurons versus TCF4$^{+/+}$ neurons. (E) Representative current-clamp traces from a TCF4$^{+/tr}$ cell showing the effect of A-803467 on the frequency of AP spiking. (F) Summary data of the effect of A-803467 application on the frequency of APs in TCF4$^{+/tr}$ cells generated in response to current injections (N=8). Post hoc analysis indicates A-803467 significantly increased firing frequency for current pulses between 250 and 350 pA. (G) Summary qRT-PCR data showing increased expression of SCN10a and decreased expression of KCNQ1 in the frontal cortex of TCF4$^{+/tr}$ mice compare to TCF4$^{+/+}$ mice. (H) Representative current-clamp traces from a TCF4$^{+/tr}$ cell showing UCL2077 has no effect on the frequency of AP spiking. (I) Summary data of the effect of UCL2077 application on the frequency of APs in TCF4$^{+/tr}$ cells generated in response to current injections (N=8). Values are presented as mean±s.e.m. and statistical significance via Bonferroni post hoc analysis (* p<0.05, ** p<0.01, & p<0.001, # p<0.0001).

To validate this model at the protein level, Western blots from embryonic day 18 (E18) embryos were performed. A truncated protein band that was dependent on genotype (FIG. 7A) was observed, thus suggesting the presence of a potentially dominant-negative protein (Sepp et al., 2012). Of interest, whole-cell recordings in layer 2/3 neurons from $Tcf4^{+/tr}$ brain slices produced a severe and consistent reduction of spike output (FIGS. 7B and 7C; p<0.0001), and the maximum number of spikes elicited by any size current pulse for each cell was also significantly reduced compared to recordings from $Tcf4^{+/+}$ littermates ($TCF4^{+/tr}$ 24.4±1.1 Hz, N=27 vs. TCF4+/+ 29.9±1.1 Hz, N=24, p<0.007). In addition, $Tcf4^{+/tr}$ cells displayed a significantly depolarized RMP compared to $Tcf4^{+/+}$ littermates (FIG. 7D; p=0.0037). This result recapitulates the intrinsic excitability phenotypes observed in the above-described cell-autonomous model and strongly suggests that these phenotypes may represent a pathophysiological state in PTHS.

If the truncated TCF4 protein that is expressed in this mouse model were capable of binding to wild-type TCF4 protein in a dominant-negative fashion, then the molecular mechanism underlying the excitability phenotypes may be different. Therefore to evaluate this, total RNA from frontal cortex homogenates from $Tcf4^{+/tr}$ and $Tcf4^{+/+}$ littermates was measured. A significant increase in Scn10a (p=0.027) expression was observed in the $Tcf4^{+/tr}$ samples; however, a significant decrease in Kcnq1 (p=0.015) expression (FIG. 7G) was found. To further test the qRT-PCR result, the SCN10a antagonist A-803467 was used and was found to be effective at rescuing AP output in $TCF4^{+/tr}$ cells; however, the KCNQ1 antagonist UCL2077 had no effect (FIG. 7I). These results confirm a role of the SCN10a sodium ion channel in the intrinsic excitability phenotype in this PTHS mouse model.

Example 6

Experimental Procedures

A. Animals and in Utero Electroporation (IUE)
Pregnant Wistar rats were obtained from Charles River Laboratories, Inc., maintained by SoBran on a 12-hour light cycle and fed ad libitum. In utero electroporation was performed as previously described (Chen et al., 2014; Maher and Loturco, 2012a). Electroporation was performed on embryonic day 16 (E16) and gestation age was confirmed during surgery. All plasmids were used at a final concentration of 1.5 µg/µl, and the mPFC was targeted for transfection. Pregnant dams were returned to the same housing conditions after recovery from surgery, and after litters were born, transfected rats were used for experiments at days P18-24.

In the mouse model used for Pitt-Hopkins syndrome (Sweatt, 2013) mice are heterozygous for a deletion of the DNA-binding domain of the Transcription Factor 4 (B6; 129-TCF4tm1Zhu/J; stock number 013598, Jackson Laboratory, Bar Harbor, Me.) (Zhuang et al., 1996). Control mouse experiments were conducted with wild-type littermates. Mice were maintained by SoBran on a 12-hour light cycle and fed ad libitum.

B. qRT-pcr

To measure Tcf4 transcript expression across the lifespan in the rat, three cortical samples per age group, as well as cortical samples extracted from both genotypes of postnatal day 21 (p21) TCF4 mice to measure SCN10a and KCNQ1 expression, were separately flash frozen and homogenized in Trizol (Life Technologies). Aqueous phase was mixed with a 1:1 volume of 70% ethanol prior to purification using RNeasy mini columns treated with DNAse according to manufacturer's protocol (Qiagen). RNA samples were then reverse-transcribed to cDNA using the Quantscript Reverse Transcriptase kit (Qiagen). Amplification of cDNA was performed with iTaq SYBR Green Supermix (Bio-Rad) and TCF4, KCNQ1, and SCN10a primers were designed using with Primer 3 software (http://bioinfo.ut.ee/primer3-0.4.0/). End-point PCR followed by product sequencing, in addition to cDNA dilution series and melt curve analysis were used to verify primer design efficiency and specificity. Real time PCR was performed on the 7900HT Fast Real-Time PCR system (Applied Biosystems) and melt curve analysis was done for absolute quantification of primer efficiency. Data were expressed as fold change of gene of interest normalized to GAPDH expression using 2^delta delta Ct.

To quantify ion channel expression from iTRAP samples, RNA was incubated with a gDNA elimination buffer for 5 minutes at 42° C. cDNA was then synthesized using the RT2 First Strand kit (Qiagen) according to manufacturer's protocol. $RT^2$ SYBRgreen master mix was added to cDNA and RNase-free water and then 25 µL of reaction mixture was added to each well of the Neuronal Ion Channel $RT^2$ Profiler PCR array plate (Qiagen, PARN-036Z).

To compare iTRAP (bound) versus unbound RNA samples, 6.6 ng of RNA was amplified and reverse-transcribed into cDNA using the Ovation Pico WTA system V2 kit according to the manufacturer's protocol (NuGEN). iTaq SYBR Green Supermix (Bio-Rad) was added to cDNA and ultra-pure water with GFAP, GAD1, EGFP, and VGAT primers designed using Primer 3 software (http://bioinfo.ut.ee/primer3-0.4.0/).

C. Transfection and Selection for Validation of shRNA/CRISPR-Cas

Rat neuroblastoma cells (B104) were cultured in Dulbecco's modified Eagle medium (DMEM) (Thermo Fisher) supplemented with 10% FBS, 100 U-100 µg/ml Penicillin-Streptomycin, 2 mM L-Glutamine, and 100 µm non-essential amino acids and maintained at 37° C. with 5% $CO_2$. At a confluency of ~70%, cells were co-transfected in 6 well plates using Lipofectamine 3000 (Thermo Fisher) with 0.5 µg PBR-GFP, a puromycin selection plasmid, and 2 µg shRNA or 2 µg CRISPR-Cas9 plasmids according to the manufacturer's protocol. Cells were selected with 500 ng/mL puromycin for 24 hours and were allowed to recover in growth medium lacking penicillin-streptomycin for 48 hours.

D. Western Blot

Rat neuroblastoma cells were washed in cold PBS, scraped from plates and pelleted by centrifugation at 4000 rpm for 5 minutes at 4° C. Cell pellets were homogenized with 27 gauge syringe needles in RIPA lysis buffer (Sigma Aldrich) containing PMSF, incubated on a shaker for 20 minutes at 4° C., and then centrifuged at 14,000 rpm for 5 minutes at 4° C.

Embryonic mice cortexes were extracted, flash frozen on dry ice and homogenized with T10 basic ultra-turrax (IKA) in a 1:15 ratio of tissue (mg):RIPA buffer containing protease inhibitor cocktail (Amresco). Samples were sonicated for 20 cycles using Sonifier 250 (Branson Ultrasonics) set at an output control of 1.5, and duty cycle of 65%. Lysates were mixed with 20% SDS (Amresco) for a final concentration of 2% and resonicated. Lysates were then incubated on a rotator for 1 hour at 4° C. and centrifuged at 20,000 g for 5 minutes at 4° C. Supernatants were quantified using BCA kit (Pierce).

30 µg of total protein were used from each sample; protein was subjected to gel electrophoresis using a 4-12% gradient Novex Bis-Tris Bolt SDS-PAGE gel. Separated proteins were transferred to 0.45 µm nitrocellulose membranes. Membranes were incubated at room temperature for 1 hour in Odyssey PBS blocking buffer (Li-Cor) and probed with anti-ITF-2 (N-16) (1:500, Santa Cruz) and anti-GAPDH (1:1000, Abcam) primary antibodies in Odyssey PBS blocking buffer overnight at 4° C. Bound antibody was detected using IRdye donkey anti-goat 680 (1:10,000, Li-Cor) and IRdye donkey anti-rabbit 800 (1:10,000, Li-Cor). Antibody detection and quantification were carried out using the LI-COR Odyssey infrared system and software.

E. Histological Procedures and Microscopy

Animals (p18-p28) were transcardially perfused under deep anesthesia with 4% paraformaldehyde in PBS. Brains were removed and post-fixed 24 hours in the same fixative solution, prior to coronal sectioning (50 m) with a vibratome (Microm, HM650V). Photomicrographs were taken with a Zeiss 700 confocal microscope and Zeiss AxioImager 2 with Zeiss ApoTome2 module.

F. Preparation of Acute Brain Slices

Acute brain slices were obtained from rats and mice as described previously (Maher and Loturco, 2012b). Briefly, P18-24 male and female animals were deeply anesthetized with isoflurane and transcardially perfused with ice-cold oxygenated (95% O2 and 5% CO2) dissecting buffer containing (in mM): 83 NaCl, 2.5 KCl, 1 $NaH_2PO_4$, 26.2 $NaHCO_3$, 22 glucose, 72 sucrose, 0.5 $CaCl_2$, and 3.3 $MgCl_2$. Animals were humanly sacrificed and decapitated and the brains were rapidly removed and immersed in ice-cold oxygenated dissection buffer. Coronal slices (300 µm) were cut using a vibratome (Microm HM650V), incubated in dissection buffer for 30-45 minutes at 34° C., and then stored at room temperature. Slices were visualized using IR differential interference microscopy (DIC) (Olympus BX51WI) and a CCD camera (QICAM, QImaging). Individual layer 2/3 pyramidal cells expressing EGFP in rat brain slices were visualized with epifluorescent illumination and a 43x Olympus LUMPlanFLN (0.8 numerical aperture) objective.

G. Electrophysiology

For all experiments, artificial cerebrospinal fluid (ACSF) was oxygenated (95% O2 and 5% CO2) and contained in (in mM): 125 NaCl, 25 NaHCO$_3$, 1.25 NaH$_2$PO$_4$, 3 KCl, 25 dextrose, 1 MgCl$_2$, and 2 CaCl$_2$, pH 7.3. Patch pipettes were fabricated from borosilicate glass (N51A, King Precision Glass, Inc.) to a resistance of 2-5 MΩ. For current- and voltage-clamp measurements, pipettes were filled with (in mM): 125 potassium gluconate, 10 HEPES, 4 Mg-ATP, 0.3 Na-GTP, 0.1 EGTA, 10 phosophocreatine, 0.05% biocytin, adjusted to pH 7.3 with KOH. For all experiments GABAa receptors were blocked with SR-95531 (Gabazine, 5 µM, Ascent Scientific). For AHP current experiments, synaptic currents were blocked with DL-2-amino-5-phosphopentanoic acid (D,L-AP5, 100 µM, Ascent Scientific), 2,3, dioxo-6-nitro-1,2,3,4, tetrahydrobenzo-quinoxaline-7-sulfonamide (NBQX, 10 µM) and SR-95531 (Gabazine, 5 µM, Ascent Scientific). Ca$_2$+-activated currents were blocked with Tetraethylammonium chloride (TEA, 1 mM, Abcam), apamin (100 nM, Abcam), and carbachol (10 µM, Abcam). Current signals were recorded with either a Multiclamp 700A (Molecular Devices) or with an Axopatch 200B amplifier (Molecular Devices) and were filtered at 2 kHz using a built-in Bessel filter and digitized at 10 kHz. Voltage signals were filtered at 2 kHz and digitized at 10 kHz. Data were acquired using Axograph on a Dell PC. Data acquisition was terminated when series resistance was >15 MΩ. For voltage clamp recordings, pyramidal cells were held at −60 mV. No holding current was used for current-clamp recordings.

H. Dynamic Clamp

Simulated synaptic inputs were delivered using Spike timing dependent plasticity Clamp (StdpC) software (Nowotny et al., 2006) (Kemenes et al., 2011) running on a second PC and connected via National Instrument data acquisition board (National Instruments, Austin, Tex.). Six individual synapses were simulated with the following parameters: gSyn 20 nS, VSyn 0 mV, tauSyn 10 ms, Vthreshold −20 mV, VSlope 25 mV and a spike generator (Vspike 80 mV, Width 2 ms, Vrest −50 mV) produced 10 bursts over 50 ms (200 Hz), 100 ms (100 Hz), and 500 ms (20 Hz). Peak action potential waveforms amplitudes (0 mV threshold) were measured over a 5 s window, and the coefficient of variance was calculated for each condition and each stimulation frequency.

I. shRNA Constructs

Hairpin sequences were designed to target the 3' UTR of TCF4 (shTCF4_2; GTTTCAGCATTCCCAATTA (SEQ ID NO:1); nucleotide position 65507957 to 65507975; accession number NC_005117.4), and the open reading frame of TCF4 (shTCF4; AGAAACTAGACGACGACAA (SEQ ID NO:2); nucleotide position 65503088-65503106; accession number NC_005117.4). The control hairpin (shCon) was designed to target DsRed (AGTTCCAGTACGGCTCCAA), (SEQ ID NO:3), (Duan et al., 2007). Sense and anti-sense oligonucleotides were designed, annealed, and cloned into the BbsI and XbaI sites of the mU6pro vector, where expression of short hairpin RNA was under the control of mouse U6 promoter.

J. CRISPR-Cas9 sgRNA was designed for spCas9 PAM recognition elements in a common exon of TCF4 (guide G ATAACGCCCGTGAGCGCCTG (SEQ ID NO:4); nucleotide position 64692509 to 64692528), and off-target effects were minimized by using the online CRISPR-Cas9 design tool (http://CRISPR-Cas9.mit.edu/) with none predicted within any genes. A "G" was added to the sgRNA sequence for compatibility with U6 promoter. The annealed oligonucleotide was cloned into the BbsI site of the PX458 vector (Ran et al., 2013) (Addgene 48138) and sequenced for confirmation. The mis-match sensitive SURVEYOR nuclease assay was performed on genomic DNA extracted from neuroblastoma cells following manufacturer protocol (Transgenesis) at 48 hours post-transfection to confirm functional CRISPR-Cas9-mediated editing. pCAG-GFP plasmid was also used to verify transfection efficiency. To determine CRISPR-Cas9 generated mutations, purified DNA from transfected rat neuroblastoma cells was subjected to PCR amplification and TA cloning. Primers were designed using Primer3 software (http:/bioinfo.ut.ee/primer3-0.4.0/). Individual plasmid clones were purified and sequenced. In all experiments, a PX458 vector with no sgRNA guide (crEmpty) was used as a control.

K. iTRAP

TRAP was performed as previously described (Heiman et al., 2014) with the following additions described below. EGFP-L10a (C2-EGFP-L10a plasmid was generous gift from Dr. Nathaniel Heintz, The Rockefeller University) was cloned into the XmaI and NotI sites of the pCAG-GFP plasmid (Addgene 11150) where expression for in utero electroporation was under the control of the CAG promoter. Replicate tissue samples were prepared from three litters of 7-9 Wistar rats that had been transfected by in utero electroporation in the medial prefrontal cortex with the L10a-GFP plasmid and either TCF4 shRNA or Control shRNA. P22 rats were deeply anesthetized with isofluorane before transcardial perfusion with ice-cold buffer containing (in mM): 83 NaCl, 2.5 KCl, 1 NaH$_2$PO$_4$, 26.2 NaHCO$_3$, 22 glucose, 72 sucrose, 0.5 CaCl$_2$, and 3.3 MgCl$_2$ (oxygenated with 95% O$_2$ and 5% CO$_2$). The brains of humanely sacrificed rats were removed and placed into dissection buffer containing cycloheximide. The transfected prefrontal cortex of each brain was dissected and all brains from a replicate litter were pooled into a Teflon-glass homogenizer and homogenized at 900 rpm. Samples were cleared of nuclei and debris by centrifugation and were incubated with detergents NP-40 (30 mM) and DHPC (1%) for 5 minutes before a final 20,000 g centrifugation for 15 minutes. Supernatant from each sample was then incubated for 1 hour at 4° C. with protein-G coated magnetic beads (Invitrogen) conjugated to monoclonal anti-GFP antibodies (19C8 and 19F7, Rockefeller Univ.). Following conjugation, supernatant was taken from the unbound fraction as an unbound total RNA control sample. Trizol reagent RNA extraction from samples was performed following manufacturer protocol (Ambion). Samples were also purified by DNase treatment before concentration with RNeasy min-elute columns (Qiagen). RNA quantity was measured with an Invitrogen Qubit, and RNA quality was confirmed with an Agilent BioAnalyzer (RIN>8).

L. Data Analysis and Statistics

Axograph was used on a Macintosh computer for analysis. To measure spike frequency, EGFP-positive layer 2/3 neurons of the mPFC were injected with a 600 ms depolarizing current pulses ranging from 50 to 500 pA at 50 pA increments with an 10 s inter-trial interval. Each current pulse was measured in triplicate, and the number of resulting APs was averaged. For analysis of fAHP amplitude, the second and third current evoked spikes within the 600 ms pulse were measured. The fAHP potential was measured by subtracting the voltage at the peak of the fAHP from the threshold potential for spike initiation (slope of AP exceeds 50 mV/ms). The mAHP potential was measured at the peak of the AHP that followed the 600 ms current pulse. The sAHP potential was measured as the average potential during a 50 ms period beginning 280 ms after the end of the 600 ms current pulse (Sah and Louise Faber, 2002; Santini et al., 2008). For voltage-clamp measurements of AHP currents, EGFP-positive pyramidal cells were clamped at −60 mV and 100 ms voltage steps to +45 mV were applied. The resulting tail currents that followed the voltage step were integrated and total charge (mV*s) was normalized by the capacitance (pF) of the cell (Maher and Westbrook, 2005). For all experiments, the group data were tested for normality using D'Agostino-Pearson omnibus normality test. For normally distributed data, statistical significance was determined using standard t-tests or ANOVA with Bonferoni post-hoc test. For non-normal distributed data, Mann-Whitney or Kruskal-Wallis test were applied. For all electrophysiology experiments, N equals number of recorded cells from a minimum of 3 animals.

The ion channel qPCR data obtained from the iTRAP approach was analyzed using linear mixed effects modeling using the R statistical software package lme4 (http://cran.r-project.org/web/packages/lme4/citation.html). For each gene, the group/treatment variable was a fixed effect and each animal was a random effect across the biological replicates. P-values were estimated using the Satterthwaite approximation (Satterthwaite, 1946).

Statistical significance is indicated on the figures as $*p<0.05$, $**p<0.01$, $\&p<0.001$, and $\#p<0.0001$. Averaged data values are reported as mean±SEM.

M. ChIP-Seq Analysis

Two TCF4 ChIP-seq samples and two input samples in the human K562 cell line were downloaded from the ENCODE project: (ChIP: ENCFF001RUO', 'ENCFF001RUP', Input: ENCFF001RVN_1', 'ENCFF001RVP_1') (Consortium, 2012). These reads were aligned to the hg19 genome using bowtie2 (Langmead and Salzberg, 2012), and then peaks were called using CisGenome (Ji et al., 2011) using the default parameters incorporating biological replicates for both the ChIP and Input samples to obtain a single ranked list of TCF4 binding peaks with corresponding statistical significance (via the false discovery rate, FDR). ChIP-seq was then performed on an Illumina HiSeq2000 using rat neural progenitor cell lysates acquired from cultured embryonic day 11 cortices. Cells were cultured on poly-D-lysine (Sigma) and laminin (Sigma) coated 75 cm2 flasks in DMEM, high glucose, HEPES (Thermo Fisher) supplemented with 1× N2 supplement (Thermo Fisher), 1× B27 supplement (ThermoFisher), 100 U/mL-100 µg/mL Penicillin-Streptomycin, 2 mM L-Glutamine, 500 µM Sodium pyruvate (Sigma), 2 ng/mL bFGF (Thermo Fisher), and 2 ng/mL EGF (Thermo Fisher) and maintained at 37° C. with 5% $CO_2$.

Using a Magna ChIP G (Millipore) kit and following the manufacture's protocol, cell lysates were immunoprecipitated using anti-IgG (Santa Cruz), anti-ITF-2 [N-16] (Santa Cruz) and anti-ITF-2 [K-12] (Santa Cruz) primary antibodies. ChIP-seq libraries were prepared with NEBNext Ultra DNA Library Prep kit from Illumina (catalogue number E7370) according to the manufacturer's instructions. 5 ng of DNA prepared from chromatin immunoprecipitation or input was used for each library preparation. DNA fragments were treated with end repair mix and A-tailing mix respectively, to generate blunt ends and to add a single A nucleotide at 3' ends. The treated fragments were used for subsequent ligation with index adaptors. The ligation products were purified and amplified with index primers to produce indexed DNA libraries. After purification and validation with LabChip GX and QPCR for library size and concentration, libraries were submitted to the Johns Hopkins Next Generation Sequencing Center for a 50-cycle single read run on a HiSeq 2000. Sequencing reads were aligned to the rn4 rat genome again using bowtie2 (Langmead and Salzberg, 2012), and peaks were called using CisGenome (Ji et al., 2011) using the default parameters to obtain a ranked list of TCF4 binding peaks with corresponding statistical significance.

Discussion of Experimental Results

In accordance with the present invention, the biological function and the pathophysiological consequence of TCF4 haploinsufficiency and dominant negative isoforms associated with PTHS and the role of TCF4 as a susceptibility factor in other neurological and neurodevelopmental psychiatric disorders have been illuminated. To determine the role of TCF4, its downstream effects and target molecules in such disorders, a newly created in vivo cellular model that mimics aspects of TCF4 expression observed in PTHS was utilized. Isomorphic expression trajectories were demonstrated in the human DLPFC and in the rat cortex across the lifespan, identifying a peak of TCF4 expression during cortical development that subsides during the postnatal period. Based on this early expression pattern, a developmental cellular assay was established by using IUE to knockdown TCF4 expression just prior to the peak of TCF4 expression in the rat. This developmental cellular assay provides a cell autonomous model of PTHS.

Using this approach, a robust function of TCF4 in the regulation of intrinsic excitability of prefrontal cortical neurons was newly identified. In utero suppression of TCF4 was shown to significantly affect intrinsic excitability by depolarizing the RMP, increasing the magnitude of the AHP, and reducing AP output. To identify the molecular mechanisms for these phenotypes, a new molecular profiling technique, iTRAP, was developed. iTRAP provides access to the translatome of IUE transfected cortical neurons. In the past, experiments using IUE have been hampered by the mosaic expression pattern produced by electroporation and the inability to selectively isolate transfected cells for molecular or biochemical profiling. However, the use of iTRAP overcomes such technical problems and allows for future mechanistic studies on the function of genes associated with neuropsychiatric disorders. By comparing the translatome between shTCF4 and shCon neurons with iTRAP, significant upregulation of Kcnq1 and Scn10a translation was identified. Analysis of two independent TCF4 ChIP-seq data (Consortium, 2012) showed direct binding of TCF4 to genomic regions within the KCNQ1 and SCN10a genes, indicating direct regulation of these genes by TCF4.

KCNQ1 is a member of the KCNQ gene family, which encodes five voltage-gated, delayed rectifier K+ channels (KCNQ1 to KCNQ5; Kv7.1 to Kv7.5) known to be the molecular components of the M-current (Delmas and Brown, 2005). The KCNQ family appears to contribute to the sAHP (Soh and Tzingounis, 2010; Tzingounis and Nicoll, 2008; Tzingounis et al., 2007), which is consistent with the findings described herein. As described in the Examples above, the KCNQ1 antagonists UCL-2077 and JNJ-303 were effective at blocking the mAHP and sAHP, and this resulted in rescue of spike frequency in shTCF4 cells. Importantly, this effect was selective to shTCF4 cells and not shCon cells. While KCNQ1 selectivity of UCL2077 is known, the selectivity of JNJ-303 for KCNQ1 over other KCNQ subunits has not been reported; however, the present findings would indicate that the selectivity of JNJ-303 for KCNQ1 is similarly selective. It is known that KCNQ channels activate slowly upon depolarization (Jentsch, 2000). The RMP was observed to be depolarized when TCF4 is suppressed (FIG. 16), and this effect may be favorable to enhancing KCNQ1 currents. In addition, neuron modeling indicates the AHP amplitude is increased at depolarized RMPs (Gu et al., 2005). Together, these results validate the iTRAP molecular profiling experiments described herein and suggest that TCF4 is regulating the expression of KCNQ1 in L2/3 pyramidal cells.

SCN10a (NaV1.8) is a peripherally expressed, TTX-resistant, voltage-gated Na$^+$ channel that shows prominent slow inactivation (Vijayaragavan et al., 2001), which is shown to be responsible for spike-frequency adaptation in dorsal root ganglion neurons (Blair and Bean, 2003). TCF4 regulation of SCN10a was validated as described in the Examples herein by showing that Scn10a overexpression resulted in phenocopy of RMP and action potential output. In addition, a specific NaV1.8 antagonist (A-803467) showed selective rescue only in shTCF4 cells. The exact biophysical mechanism responsible for this phenocopy is not known. Wild-type SCN10a is not known to regulate the RMP; however, an SCN10a point mutant (I1706V) found in a patient with idiopathic small-fiber neuropathy lead to a depolarized RMP in dorsal root ganglion cells (Huang et al., 2013). It is therefore reasonable to infer that increasing the expression of a sodium channel would favor a more depolarized RMP. The effect of SCN10a on AP output likely involves slow inactivation of the channel during a train of APs (Blair and Bean, 2003). It is important to note that TTX resistant Na$^+$ currents are thought to be only expressed in the peripheral nervous system (Baker and Wood, 2001; McCleskey and Gold, 2003). Accordingly, the results provided herein are the first report of a role of expression of Scn10a in the central nervous system despite suggestions that SCN10a mRNA is present at low levels in the mouse and human neocortex (Hawrylycz et al., 2012; Lein et al., 2007).

As further validation of the intrinsic excitability phenotypes found in the cell-autonomous model of PTHS as described herein, similar deficits in AP output were observed in a mouse model of PTHS in which one allele of Tcf4 produces a truncated TCF4 protein. This mouse model, therefore, more closely matches the molecular biology of PTHS (Sweatt, 2013). Homozygous deletion of TCF4 is lethal at birth and defects in progenitor cell migration in the pontine nucleus are reported (Flora et al., 2007). Heterozygous mice, which model the genetic abnormality of PTHS in humans, exhibit abnormal gut function, which is the most common non-neurological symptom in PTHS patients (Grubisic et al., 2015). Thus, this mouse is validated as a model of at least some fundamental aspects of PTHS. Although intrinsic excitability phenotypes were consistent across the two model systems described herein, the underlying mechanism was only partially consistent. This discrepancy is likely due to model construction as shTCF4 and crTCF4 produce haploinsufficiency while expression of a truncated TCF4 protein is likely a dominant negative. The divergent expression of Kcnq1, yet similar expression of Scn10a, between these two models indicates that transcriptional control by TCF4 is different depending on the gene being regulated and is consistent with context-dependence of bHLH proteins (Powell and Jarman, 2008). The results suggest that TCF4 homodimers are important to the regulation Scn10a, but TCF4 heterodimers may regulate Kcnq1; this type of differential regulation may explain the varied symptomology observed in the PTHS patient population. The physiological abnormalities observed in the cortex of these mice implicate an abnormality of neuronal excitability as a possible mechanism of the cognitive disability also observed in this condition. Moreover, the consistency of the excitability phenotypes between the mouse model and the cell-autonomous model support the conclusion that TCF4 is a regulator of intrinsic neuronal excitability.

TCF4 is linked to several neuropsychiatric disorders including schizophrenia, PTHS, and 18q deletion syndrome. For schizophrenia, common variants, some within introns of TCF4, have reached genome-wide significance for association with diagnosis (Schizophrenia Psychiatric Genome-Wide Association Study (GWAS) Consortium, 2011). In addition, several TCF4 SNPs including some risk SNPs, are associated with SZ endophenotypes including cognition and sensorimotor gating (Quednow et al., 2011; Zhu et al., 2012). However, the molecular mechanism for these associations are not known, as none of these genetic variants have been shown to be associated with expression differences (Williams et al., 2011). Given that dominant negative TCF4 or TCF4 haploinsufficiency results in PTHS, a syndrome with much more profound neurodevelopmental deficits than those observed in schizophrenia, the mechanism of schizophrenia risk associated with TCF4 is presumably due to less extreme alterations in TCF4 expression at some unknown time point in development. Physiological phenotype related to cortical excitability may be a feature of the TCF4 risk factor associated with schizophrenia. As support for this, studies of cortical physiology in patients with schizophrenia and in their healthy siblings have implicated altered cortical excitability (Callicott, 2003).

PTHS syndrome is characterized by variable symptomatology presumably because of allelic heterogeneity represented in the deletions/mutations, producing both haploinsufficiency and/or dominant negative effects (Sepp et al., 2012). This expression deficiency may lead to intrinsic excitability defects in part due to altered expression of KCNQ1 and SCN10a. The pathological expression of these peripheral ion channels in the CNS may create a unique opportunity to target these channels with therapeutic agents without producing unwanted off-target effects on normal neuronal physiology. The description and experimental results herein support the notion that targeting these ion channels may ameliorate behavioral and cognitive deficits observed in PTHS, as well as other neurological disorders, such as schizophrenia.

It is known that learning can alter the intrinsic excitability of neurons by affecting voltage-gated and calcium-gated channels present in spines, dendrites, and cell bodies (Daoudal and Debanne, 2003; Disterhoft and Oh, 2006; Giese et al., 2001; Santini et al., 2008; Schulz, 2006; Zhang and Linden, 2003). Several learning paradigms in rodents, such as eyeblink conditioning, spatial learning, inhibitory avoidance, fear conditioning and odor discrimination, are correlated with modification in the intrinsic excitability of principal neurons (Faber and Sah, 2003; Oh and Disterhoft, 2014). Moreover, persistent firing in L3 cells of the prefrontal cortex is necessary for working memory tasks (Goldman-Rakic, 1995; Wang et al., 2013). The experimental data and results herein show that prefrontal neurons from two independent models of PTHS are incapable of maintaining sustained AP firing. Thus, this phenotype may underlie some aspects of the cognitive deficits observed in PTHS and in other neurological disorders, such as schizophrenia.

All patents, patent applications and publications referred to or cited herein are hereby incorporated by reference in their entireties for all purposes.

It is understood that the embodiments and examples described herein are for illustrative purposes and that various modifications or changes in light thereof will be suggested to persons skilled in the pertinent art and are to be included within the spirit and purview of this application and scope of the appended claims. It is to be understood that suitable methods and materials are described herein for the practice of the embodiments; however, methods and materials that are similar or equivalent to those described herein can be used in the practice or testing of the invention and described embodiments.

LIST OF REFERENCES

Abel, H. J. (2003). Relationships Between Intracellular Calcium and Afterhyperpolarizations in Neocortical Pyramidal Neurons. J Neurophysiol 91, 324-335.

Alvarez, V. A., Ridenour, D. A., and Sabatini, B. L. (2006). Retraction of synapses and dendritic spines induced by off-target effects of RNA interference. Journal of Neuroscience 26, 7820-7825.

Amiel, J., Rio, M., de Pontual, L., Redon, R., Malan, V., Boddaert, N., Plouin, P., Carter, N. P., Lyonnet, S., Munnich, A., et al. (2007). Mutations in TCF4, encoding a class I basic helix-loop-helix transcription factor, are responsible for Pitt-Hopkins syndrome, a severe epileptic encephalopathy associated with autonomic dysfunction. Am J Hum Genet 80, 988-993.

Baek, S. T., Kerjan, G., Bielas, S. L., Lee, J. E., Fenstermaker, A. G., Novarino, G., and Gleeson, J. G. (2014). Off-target effect of doublecortin family shRNA on neuronal migration associated with endogenous microRNA dysregulation. Neuron 82, 1255-1262.

Baker, M. D., and Wood, J. N. (2001). Involvement of Na+ channels in pain pathways. Trends in Pharmacological Sciences 22, 27-31.

Bean, B. P. (2007). The action potential in mammalian central neurons. Nat Rev Neurosci 8, 451-465.

Blair, N. T., and Bean, B. P. (2003). Role of tetrodotoxin-resistant Na+ current slow inactivation in adaptation of action potential firing in small-diameter dorsal root ganglion neurons. Journal of Neuroscience 23, 10338-10350.

Brockschmidt, A., Filippi, A., Charbel Issa, P., Nelles, M., Urbach, H., Eter, N., Driever, W., and Weber, R. G. (2011). Neurologic and ocular phenotype in Pitt-Hopkins syndrome and a zebrafish model. Hum Genet 130, 645-655.

Callicott, J. H. (2003). An expanded role for functional neuroimaging in schizophrenia. Curr Opin Neurobiol 13, 256-260.

Chen, F., Maher, B. J., and Loturco, J. J. (2014). PiggyBac Transposon-Mediated Cellular Transgenesis in Mammalian Forebrain by In Utero Electroporation. Cold Spring Harb Protoc 2014, pdb.prot073650-pdb.prot073650.

Consortium, T. E. P. (2012). An integrated encyclopedia of DNA elements in the human genome. Nature 489, 57-74.

Cooper, E. C., Aldape, K. D., Abosch, A., Barbaro, N. M., Berger, M. S., Peacock, W. S., Jan, Y. N., and Jan, L. Y. (2000). Colocalization and coassembly of two human brain M-type potassium channel subunits that are mutated in epilepsy. Proc Natl Acad Sci USA 97, 4914-4919.

Corneliussen, B., Thornell, A., Hallberg, B., and Grundstrom, T. (1991). Helix-loop-helix transcriptional activators bind to a sequence in glucocorticoid response elements of retrovirus enhancers. J. Virol. 65, 6084-6093.

Daoudal, G., and Debanne, D. (2003). Long-term plasticity of intrinsic excitability: learning rules and mechanisms. Learning & Memory 10, 456-465.

de Pontual, L. C., Mathieu, Y., Golzio, C., Rio, M. N., Malan, V. R., Boddaert, N., Soufflet, C., Picard, C., Durandy, A., Dobbie, A., et al. (2009). Mutational, functional, and expression studies of the TCF4 gene in Pitt-Hopkins syndrome. Hum. Mutat. 30, 669-676.

Delmas, P., and Brown, D. A. (2005). Pathways modulating neural KCNQ/M (Kv7) potassium channels. Nat Rev Neurosci 6, 850-862.

Disterhoft, J. F., and Oh, M. M. (2006). Learning, aging and intrinsic neuronal plasticity. Trends Neurosci 29, 587-599.

Duan, X., Chang, J. H., Ge, S., Faulkner, R. L., Kim, J. Y., Kitabatake, Y., Liu, X.-B., Yang, C.-H., Jordan, J. D., Ma, D. K., et al. (2007). Disrupted-In-Schizophrenia 1 regulates integration of newly generated neurons in the adult brain. Cell 130, 1146-1158.

Faber, E. S. L., and Sah, P. (2003). Calcium-Activated Potassium Channels: Multiple Contributions to Neuronal Function. Neuroscientist 9, 181-194.

Flora, A., Garcia, J. J., Thaller, C., and Zoghbi, H. Y. (2007). The E-protein Tcf4 interacts with Math1 to regulate differentiation of a specific subset of neuronal progenitors. Proc Natl Acad Sci USA 104, 15382-15387.

Forrest, M., Chapman, R. M., Doyle, M., Tinsley, C. L., Waite, A., and Blake, D. J. (2012). Functional analysis of TCF4 missense mutations that cause Pitt-Hopkins Syndrome. Hum. Mutat. n/a-n/a.

Giese, K. P., Peters, M., and Vernon, J. (2001). Modulation of excitability as a learning and memory mechanism: A molecular genetic perspective. Physiology & Behavior 73, 803-810.

Goldberg, T. E., and Weinberger, D. R. (1988). Probing prefrontal function in schizophrenia with neuropsychological paradigms. Schizophr Bull 14, 179-183.

Goldman-Rakic, P. S. (1994). Working memory dysfunction in schizophrenia. J Neuropsychiatry Clin Neurosci 6, 348-357.

Goldman-Rakic, P. S. (1995). Cellular basis of working memory. Neuron 14, 477-485.

Grubišić, V., Kennedy, A. J., Sweatt, J. D., and Parpura, V. (2015). Pitt-Hopkins Mouse Model has Altered Particular Gastrointestinal Transits In Vivo. Autism Res.

Gu, N., Vervaeke, K., Hu, H., and Storm, J. F. (2005). Kv7/KCNQ/M and HCN/h, but not KCa2/SK channels, contribute to the somatic medium after-hyperpolarization and excitability control in CA1 hippocampal pyramidal cells. The Journal of Physiology 566, 689-715.

Guillemot, F. (2007). Cell fate specification in the mammalian telencephalon. Prog. Neurobiol. 83, 37-52.

Hawrylycz, M. J., Lein, E. S., Guillozet-Bongaarts, A. L., Shen, E. H., Ng, L., Miller, J. A., van de Lagemaat, L. N., Smith, K. A., Ebbert, A., Riley, Z. L., et al. (2012). An anatomically comprehensive atlas of the adult human brain transcriptome. Nature 489, 391-399.

Heiman, M., Kulicke, R., Fenster, R. J., Greengard, P., and Heintz, N. (2014). Cell type-specific mRNA purification by translating ribosome affinity purification (TRAP). Nat Protoc 9, 1282-1291.

Heiman, M., Schaefer, A., Gong, S., Peterson, J. D., Day, M., Ramsey, K. E., Suárez-Fariñas, M., Schwarz, C., Stephan, D. A., Surmeier, D. J., et al. (2008). A Translational Profiling Approach for the Molecular Characterization of CNS Cell Types. Cell 135, 738-748.

Henthorn, P., Kiledjian, M., and Kadesch, T. (1990). Two distinct transcription factors that bind the immunoglobulin enhancer microE5/kappa 2 motif. Science 247, 467-470.

Hille, B. (2001). Ion channels of excitable membranes.

Huang, J., Yang, Y., Zhao, P., Gerrits, M. M., Hoeijmakers, J. G. J., Bekelaar, K., Merkies, I. S. J., Faber, C. G., Dib-Hajj, S. D., and Waxman, S. G. (2013). Small-Fiber Neuropathy Nav1.8 Mutation Shifts Activation to Hyperpolarized Potentials and Increases Excitability of Dorsal Root Ganglion Neurons. J Neurosci 33, 14087-14097.

Jentsch, T. J. (2000). Neuronal KCNQ potassium channels: physislogy and role in disease. Nat Rev Neurosci 1, 21-30.

Ji, H., Jiang, H., Ma, W., and Wong, W. H. (2011). Using CisGenome to Analyze ChIP-chip and ChIP-seq Data (John Wiley & Sons, Inc.).

Ji, H., Jiang, H., Ma, W., Johnson, D. S., Myers, R. M., and Wong, W. H. (2008). An integrated software system for analyzing ChIP-chip and ChIP-seq data. Nat Biotechnol 26, 1293-1300.

Kemenes, I., Marra, V., Crossley, M., Samu, D., Staras, K., Kemenes, G., and Nowotny, T. (2011). Dynamic clamp with StdpC software. Nat Protoc 6, 405-417.

Langevin, L. M., Mattar, P., Scardigli, R., Roussigne, M., Logan, C., Blader, P., and Schuurmans, C. (2007). Validating in utero electroporation for the rapid analysis of gene regulatory elements in the murine telencephalon. Dev. Dyn. 236, 1273-1286.

Langmead, B., and Salzberg, S. L. (2012). Fast gapped-read alignment with Bowtie 2. Nat Methods 9, 357-359.

Lein, E. S., Hawrylycz, M. J., Ao, N., Ayres, M., Bensinger, A., Bernard, A., Boe, A. F., Boguski, M. S., Brockway, K. S., Byrnes, E. J., et al. (2007). Genome-wide atlas of gene expression in the adult mouse brain. Nature 445, 168-176.

Lorenzon, N. M., and Foehring, R. C. (1995). Alterations in intracellular calcium chelation reproduce developmental differences in repetitive firing and afterhyperpolarizations in rat neocortical neurons. Developmental Brain Research 84, 192-203.

Maher, B. J., and Loturco, J. J. (2012a). In Utero Electroporation for Cellular Transgenesis in the Developing Mammalian Forebrain. In Neuromethods, A. Morozov, ed. (Totowa, N.J.: Humana Press), pp. 113-128.

Maher, B. J., and Loturco, J. J. (2012b). Disrupted-in-Schizophrenia (DISC1) Functions Presynaptically at Glutamatergic Synapses. PLoS ONE 7, e34053.

Maher, B. J., and Westbrook, G. L. (2005). SK channel regulation of dendritic excitability and dendrodendritic inhibition in the olfactory bulb. J Neurophysiol 94, 3743-3750.

Massari, M. E., and Murre, C. (2000). Helix-Loop-Helix Proteins: Regulators of Transcription in Eucaryotic Organisms. Mol Cell Biol 20, 429-440.

McCleskey, E. W., and Gold, M. S. (2003). ION CHANNELS OF NOCICEPTION. Http://Dx.Doi.org/10.1146/Annurev.Physiol.61.1.835 61, 835-856.

Nowotny, T., Szűcs, A., Pinto, R. D., and Selverston, A. I. (2006). StdpC: A modern dynamic clamp. J Neurosci Methods 158, 287-299.

Oh, M. M., and Disterhoft, J. F. (2014). Increased Excitability of Both Principal Neurons and Interneurons during Associative Learning. Neuroscientist 1073858414537382.

Powell, L. M., and Jarman, A. P. (2008). Context dependence of proneural bHLH proteins. Curr Opin Genet Dev 18, 411-417.

Quednow, B. B., Ettinger, U., Mossner, R., Rujescu, D., Giegling, I., Collier, D. A., Schmechtig, A., Kuhn, K.-U., Moller, H.-J., Maier, W., et al. (2011). The Schizophrenia Risk Allele C of the TCF4 rs9960767 Polymorphism Disrupts Sensorimotor Gating in Schizophrenia Spectrum and Healthy Volunteers. Journal of Neuroscience 31, 6684-6691.

Ran, F. A., Hsu, P. D., Lin, C.-Y., Gootenberg, J. S., Konermann, S., Trevino, A. E., Scott, D. A., Inoue, A., Matoba, S., Zhang, Y., et al. (2013). Double Nicking by RNA-Guided CRISPR Cas9 for Enhanced Genome Editing Specificity. Cell 154, 1380-1389.

Sah, P., and Louise Faber, E. S. (2002). Channels underlying neuronal calcium-activated potassium currents. Prog. Neurobiol. 66, 345-353.

Santini, E., Quirk, G. J., and Porter, J. T. (2008). Fear conditioning and extinction differentially modify the intrinsic excitability of infralimbic neurons. Journal of Neuroscience 28, 4028-4036.

Satterthwaite, F. E. (1946). An approximate distribution of estimates of variance components. Biometrics 2, 110-114.

Schizophrenia Psychiatric Genome-Wide Association Study (GWAS) Consortium (2011). Genome-wide association study identifies five new schizophrenia loci. Nat Genet 43, 969-976.

Schizophrenia Working Group of the Psychiatric Genomics Consortium (2014). Biological insights from 108 schizophrenia-associated genetic loci. Nature 511, 421-427.

Schulz, D. J. (2006). Plasticity and stability in neuronal output via changes in intrinsic excitability: it's what's inside that counts. J Exp Biol 209, 4821-4827.

Sepp, M., Pruunsild, P., and Timmusk, T. (2012). Pitt-Hopkins syndrome-associated mutations in TCF4 lead to variable impairment of the transcription factor function ranging from hypomorphic to dominant-negative effects. Hum Mol Genet.

Sepp, M., Kannike, K., Eesmaa, A., Urb, M., and Timmusk, T. (2011). Functional Diversity of Human Basic Helix-Loop-Helix Transcription Factor TCF4 Isoforms Generated by Alternative 5' Exon Usage and Splicing. PLoS ONE 6, e22138.

Soh, H., and Tzingounis, A. V. (2010). The specific slow afterhyperpolarization inhibitor UCL2077 is a subtype-selective blocker of the epilepsy associated KCNQ channels. Mol Pharmacol 78, 1088-1095.

Soileau, B., Hasi, M., Sebold, C., Hill, A., O'Donnell, L., Hale, D. E., and Cody, J. D. (2014). Adults with Chromosome 18 Abnormalities. J Genet Couns 1-12.

Sweatt, J. D. (2013). Pitt-Hopkins Syndrome: intellectual disability due to loss of TCF4-regulated gene transcription. Exp. Mol. Med. 45, e21.

Towart, R., Linders, J. T. M., Hermans, A. N., Rohrbacher, J., van der Linde, H. J., Ercken, M., Cik, M., Roevens, P., Teisman, A., and Gallacher, D. J. (2009). Blockade of the IKs potassium channel: An overlooked cardiovascular liability in drug safety screening? Journal of Pharmacological and Toxicological Methods 60, 1-10.

Tzingounis, A. V., and Nicoll, R. A. (2008). Contribution of KCNQ2 and KCNQ3 to the medium and slow afterhyperpolarization currents. Proceedings of the National Academy of Sciences 105, 19974-19979.

Tzingounis, A. V., Kobayashi, M., Takamatsu, K., and Nicoll, R. A. (2007). Hippocalcin Gates the Calcium Activation of the Slow Afterhyperpolarization in Hippocampal Pyramidal Cells. Neuron 53, 487-493.

Vijayaragavan, K., O'Leary, M. E., and Chahine, M. (2001). Gating properties of Na(v)1.7 and Na(v)1.8 peripheral nerve sodium channels. Journal of Neuroscience 21, 7909-7918.

Vogalis, F., Storm, J. F., and Lancaster, B. (2003). SK channels and the varieties of slow afterhyperpolarizations in neurons. Eur J Neurosci 18, 3155-3166.

Wang, M., Yang, Y., Wang, C.-J., Gamo, N. J., Jin, L. E., Mazer, J. A., Morrison, J. H., Wang, X.-J., and Arnsten, A. F. T. (2013). NMDA Receptors Subserve Persistent Neuronal Firing during Working Memory in Dorsolateral Prefrontal Cortex. Neuron 77, 736-749.

Whalen, S., Heron, D., Gaillon, T., Moldovan, O., Rossi, M., Devillard, F., Giuliano, F., Soares, G., Mathieu-Dramard, M., Afenjar, A., et al. (2012). Novel comprehensive diagnostic strategy in Pitt-Hopkins syndrome: clinical score and further delineation of the TCF4 mutational spectrum. Hum. Mutat. 33, 64-72.

Williams, H. J., Moskvina, V., Smith, R. L., Dwyer, S., Russo, G., Owen, M. J., and O'Donovan, M. C. (2011). Association between TCF4 and schizophrenia does not exert its effect by common nonsynonymous variation or by influencing cis-acting regulation of mRNA expression in adult human brain. Am. J. Med. Genet. 156, 781-784.

Zhang, W., and Linden, D. J. (2003). The other side of the engram: experience-driven changes in neuronal intrinsic excitability. Nat Rev Neurosci 4, 885-900.

Zhu, X., Gu, H., Liu, Z., Xu, Z., Chen, X., Sun, X., Zhai, J., Zhang, Q., Chen, M., Wang, K., et al. (2012). Associations between TCF4 Gene Polymorphism and Cognitive Functions in Schizophrenia Patients and Healthy Controls. Neuropsychopharmacology 38, 683-689.

Zhuang, Y., Cheng, P., and Weintraub, H. (1996). B-lymphocyte development is regulated by the combined dosage of three basic helix-loop-helix genes, E2A, E2-2, and HEB. Mol Cell Biol 16, 2898-2905.

Zweier, C., Sticht, H., Bijlsma, E. K., Clayton-Smith, J., Boonen, S. E., Fryer, A., Greally, M. T., Hoffmann, L., Hollander, den, N. S., Jongmans, M., et al. (2008). Further delineation of Pitt-Hopkins syndrome: phenotypic and genotypic description of 16 novel patients. J. Med. Genet. 45, 738-744.

What is claimed is:

1. A method of reducing at least one symptom of Pitt-Hopkins Syndrome (PTHS), said method comprising: administering to the subject a therapeutically effective amount of a SCN10a selective antagonist or a KCNQ1 selective antagonist or a combination of thereof to treat the disease or disorder, wherein the SCN10a selective antagonist is selected from the group consisting of A-803467, PF-01247324, PF-04885614, PF-04531083, PF-5157147, A-887826, ambroxol hydrochloride, APETX2, vinpocetine, PF-6305591, DSP-2230, 2-(4-fluoro-2-methoxyphenoxy)-N-(2-oxo-1,2-dihydropyridin-4-yl)-4-(trifluoromethyl)benzamide, VX-150, aryl-substituted nicotinamide derivatives of A-803467, PF-01247324, PF-04531083, PF-6305591, PF-04885614, PF-5157147, A-887826, Ambroxol hydrochloride, DSP-2230, vinpocetine, VX-150, or APETX2, and a salt or hydrate and wherein the KCNQ1 selective antagonist is selected from the group consisting of Chromanol 293B, MIR-1556, UCL2077, JNJ303, L-735821 (L-7), fenofibrate; and a salt or hydrate thereof.

2. The method according to claim 1, wherein the subject is administered a therapeutically effective amount of a SCN10a selective antagonist.

3. The method according to claim 2, wherein the SCN10a antagonist is PF-04531083.

4. The method according to claim 1, wherein the subject is administered a therapeutically effective amount of a SCN10a selective antagonist in combination with a therapeutically effective amount of a KCNQ1 antagonist.

5. The method according to claim 1, wherein the subject is administered a therapeutically effective amount of a KCNQ1 selective antagonist.

6. A method of reducing an aberrant excitability phenotype of CNS neuronal cells expressing SCN10a or KCNQ1 in a subject having a neurological or neurodevelopmental disorder associated with abnormal TCF4 expression and/or function and selected from Pitt-Hopkins Syndrome (PTHS), autism, autism spectrum disorder, 18q syndrome and schizophrenia, the method comprising administering to the subject a therapeutically effective amount of a selective antagonist of SCN10a or KCNQ1 to reduce the symptoms of the neurological or neurodevelopmental disorder in the subject, wherein the SCN10a selective antagonist is selected from the group consisting of A-803467, PF-01247324, PF-04885614, PF-04531083, PF-5157147, A-887826, ambroxol hydrochloride, APETX2, vinpocetine, PF-6305591, DSP-2230, 2-(4-fluoro-2-methoxyphenoxy)-N-(2-oxo-1,2-dihydropyridin-4-yl)-4-(trifluoromethyl)benzamide, VX-150, aryl-substituted nicotinamide derivatives of A-803467, PF-01247324, PF-04531083, PF-6305591, PF-04885614, PF-5157147, A-887826, Ambroxol hydrochloride, DSP-2230, vinpocetine, VX-150, or APETX2, and a salt or hydrate and wherein the KCNQ1 selective antagonist is selected from the group consisting of Chromanol 293B, MIR-1556, UCL2077, JNJ303, L-735821 (L-7), fenofibrate; and a salt or hydrate thereof.

7. The method according to claim 6, wherein the selective antagonist is SCN10a and the SCN10a antagonist is PF-04531083.

8. The method according to claim 6, wherein the neurological or neurodevelopmental disease or disorder is PTHS.

9. The method according to claim 6, wherein the neurological or neurodevelopmental disease or disorder is 18q syndrome.

10. The method according to claim 6, wherein the neurological or neurodevelopmental disease or disorder is schizophrenia.

11. The method according to claim 6, wherein the subject is administered a therapeutically effective amount of a SCN10a selective antagonist.

12. The method according to claim 11, wherein the SCN10a antagonist is PF-04531083.

13. The method according to claim 6, wherein the subject is administered a therapeutically effective amount of a KCNQ1 selective antagonist.

14. A method of inhibiting the activity of $Na_v$ 1.8 sodium channels or KCNQ1 potassium channels in a subject having a neurological or neurodevelopmental disorder associated with abnormal TCF4 expression and/or function and selected from Pitt-Hopkins Syndrome (PTHS), autism, autism spectrum disorder, 18q syndrome, and schizophrenia, the method comprising administering to the subject a therapeutically effective amount of a selective antagonist of SCN10a or KCNQ1 to reduce the symptoms of the neurological or neurodevelopmental disorder in the subject, wherein the SCN10a selective antagonist is selected from the group consisting of A-803467, PF-01247324, PF-04885614, PF-04531083, PF-5157147, A-887826, ambroxol hydrochloride, APETX2, vinpocetine, PF-6305591, DSP-2230, 2-(4-fluoro-2-methoxyphenoxy)-N-(2-oxo-1,2-dihydropyridin-4-yl)-4-(trifluoromethyl)benzamide, VX-150, aryl-substituted nicotinamide derivatives of A-803467, PF-01247324, PF-04531083, PF-6305591, PF-04885614, PF-5157147, A-887826, Ambroxol hydrochloride, DSP-2230, vinpocetine, VX-150, or APETX2, and a salt or hydrate and wherein the KCNQ1 selective antagonist is selected from the group consisting of Chromanol 293B, MIR-1556, UCL2077, JNJ303, L-735821 (L-7), fenofibrate; and a salt or hydrate thereof.

15. The method according to claim 14, wherein the neurological or neurodevelopmental disease or disorder is PTHS.

16. The method according to claim 14, wherein the neurological or neurodevelopmental disease or disorder is 18q syndrome.

17. The method according to claim 14, wherein the neurological or neurodevelopmental disease or disorder is schizophrenia.

18. The method according to claim 14, wherein the neurological or neurodevelopmental disease or disorder is autism or autism spectrum disorder.

19. The method according to claim 14, wherein the subject is administered a therapeutically effective amount of a SCN10a selective antagonist.

20. The method according to claim 14, wherein the subject is administered a therapeutically effective amount of a KCNQ1 selective antagonist.

* * * * *